United States Patent
Silverman

(10) Patent No.: US 11,241,488 B2
(45) Date of Patent: Feb. 8, 2022

(54) METHODS AND COMPOSITIONS FOR TREATING AND DIAGNOSING AUTOIMMUNE DISEASES

(71) Applicant: New York University, New York, NY (US)

(72) Inventor: Gregg Silverman, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 16/611,793

(22) PCT Filed: May 10, 2018

(86) PCT No.: PCT/US2018/032161
§ 371 (c)(1),
(2) Date: Nov. 7, 2019

(87) PCT Pub. No.: WO2018/209149
PCT Pub. Date: Nov. 15, 2018

(65) Prior Publication Data
US 2020/0061176 A1 Feb. 27, 2020

Related U.S. Application Data

(60) Provisional application No. 62/504,146, filed on May 10, 2017.

(51) Int. Cl.
| | |
|---|---|
| *A61K 39/02* | (2006.01) |
| *A61P 37/00* | (2006.01) |
| *A61P 31/04* | (2006.01) |
| *A61K 31/43* | (2006.01) |
| *A61K 31/4706* | (2006.01) |
| *A61K 31/573* | (2006.01) |
| *A61K 35/741* | (2015.01) |
| *A61K 38/17* | (2006.01) |
| *A61K 39/395* | (2006.01) |
| *C12Q 1/689* | (2018.01) |
| *G01N 33/564* | (2006.01) |

(52) U.S. Cl.
CPC .......... *A61K 39/0208* (2013.01); *A61K 31/43* (2013.01); *A61K 31/4706* (2013.01); *A61K 31/573* (2013.01); *A61K 35/741* (2013.01); *A61K 38/177* (2013.01); *A61K 39/39508* (2013.01); *A61P 31/04* (2018.01); *A61P 37/00* (2018.01); *C12Q 1/689* (2013.01); *G01N 33/564* (2013.01); *C12Q 2600/118* (2013.01); *G01N 2400/02* (2013.01); *G01N 2469/20* (2013.01); *G01N 2800/104* (2013.01); *G01N 2800/347* (2013.01); *G01N 2800/50* (2013.01)

(58) Field of Classification Search
None
See application file for complete search history.

(56) References Cited

U.S. PATENT DOCUMENTS

2016/0320406 A1 11/2016 Elledge et al.

OTHER PUBLICATIONS

Vaccines, 1986, Edited by Fred Brown: Cold Spring Harbor Laboratory) (Year: 1986).*
Communication (International Preliminary Report of Patentability) issued by the International Searching Authority in International Application No. PCT/US2018/32161 dated Nov. 12, 2019, 15 pages total.
Mu, Q., "SLE: Another Autoimmune Disorder Influenced by Microbes and Diet?" Frontiers in Immunology (2015) vol. 6, Article 608, 10 pages total.
Yurasov, S. et al., "Defective B Cell Tolerance Checkpoints in Systemic Lupus Erythematosus" The Journal of Experimental Medicine (2005) vol. 201, No. 5, pp. 703-711.
Communication (International Search Report) issued by the International Searching Authority in International Application No. PCT/US2018/32161 dated Oct. 1, 2018, 6 pages total.
Communication (Written Opinion) issued by the International Searching Authority in International Application No. PCT/US2018/32161 dated Oct. 1, 2018, 14 pages total.
Izui, S. et al., "Features of Systemic Lupus Erythematosus in Mice Injected with Bacterial Lipopolysaccharides: Identification of Circulating DNA and Renal Localization of DNA-Anti-DNA Complexes" The Journal of Experimental Medicine (1977) vol. 145, No. 5, pp. 1115-1130.
Koyama, A. et al., "*Staphylococcus aureus* Cell Envelope Antigen is a New Candidate for the Induction of IgA Nephropathy" Kidney International (2004) vol. 66, No. 1, pp. 121-132.
Landers, C.J. et al., "Selected Loss of Tolerance Evidence by Crohn's Disease-Associated Immune Responses to Auto- and Microbial Antigens" Gastroenterology (2002) vol. 123, pp. 689-699.
Katz-Agranov, N. et al., "The Microbiome and Systemic Lupus Erythematosus" Immunol Res (2017) vol. 65, pp. 432-437.
Johnson, B.M. et al., "Impact of Dietary Deviation on Disease Progression and Gut Microbiome Composition in Lupus-Prone SNF1 Mice" Clinical & Experimental Immunology (2015) vol. 181, No. 2, pp. 232-237.
Willing, B.P. et al., "A Pyrosequencing Study in Twins Shows that Gastrointestinal Microbial Profiles Vary with Inflammatory Bowel Disease Phenotypes" Gastroenterology (2010) vol. 139, No. 6, pp. 1844-1854.
NCBI Reference Sequence: NZ_AZJF00000000.1 Ruminococcus gnavus CC55_001C, whole genome shotgun sequencing project Apr. 10, 2017 [online], [Retrieved Aug. 22, 2018], 2 pages total.

(Continued)

*Primary Examiner* — Padmavathi Baskar
(74) *Attorney, Agent, or Firm* — Troutman Pepper Hamilton Sanders LLP

(57) ABSTRACT

The application relates to methods for the diagnosis, treatment, and prevention of autoimmune and/or inflammatory disease such as systemic lupus erythematosus (SLE), lupus nephritis, IgA nephropathy, other types of glomerulonephritis.

9 Claims, 26 Drawing Sheets
(12 of 26 Drawing Sheet(s) Filed in Color)

(56) References Cited

OTHER PUBLICATIONS

Graziani, F. et al., "Ruminococcus Gnabus E1 Modulates Mucin Expression and Intestinal Glycosylation" The Journal of Applied Microbiology (2016) vol. 210, No. 5, pp. 1403-1417.
Caporaso, J.G. et al., "QIIME Allows Analysis of High-Throughput Community Sequencing Data" Nat Methods (2010) vol. 7, No. 5, 4 pages total.

* cited by examiner

METHODS AND COMPOSITIONS FOR TREATING AND DIAGNOSING AUTOIMMUNE DISEASES

CROSS-REFERENCE TO RELATED APPLICATIONS

This application is a U.S. National Phase Application of International Application No. PCT/US18/32161, filed on May 10, 2018, which claims priority to U.S. Provisional Patent Application No. 62/504,146, filed on May 10, 2017, all of which are herein incorporated by reference in their entireties.

FIELD

The application relates to methods for the diagnosis, treatment, and prevention of autoimmune disease such as, but not limited to, systemic lupus erythematosus (SLE) incomplete lupus (ILE) syndrome, and lupus nephritis as well as inflammatory diseases such as, but not limited to, glomerulonephritis, and inflammatory bowel disease (IBD)

BACKGROUND

Systemic lupus erythematosus (SLE) is an autoimmune disease in which the immune system makes antibodies to cells and molecules in the body, leading to widespread inflammation and tissue damage. The causes of SLE are believed linked to genetic and to hormonal factors, as well as environmental factors that remain poorly understood.

Although most epidemiologic studies have focused on genetic factors, environmental influences may be inferred in results from a recent large survey of over 23 million individuals, representing nearly the entire population of Taiwan (1). As expected, homozygotic twins showed a relative risk (RR) of over 300 for disease concordance, while those with an affected first-degree relative (FDR) had an overall RR of Lupus over 17-fold. Strikingly, spouses "without genetic similarity" had a 4-fold RR (2.38-8.30). By contrast, individual disease-associated SNPs and genetic intervals generally convey a less than 1.4-fold RR (2).

SLE family members, including spouses, are reported to more commonly have serum Lupus autoantibodies (3, 4). Laboratory workers that handle blood from SLE patients are reported to also have significantly higher rates of serum anti-DNA antibodies (5). Notably, family members are known to more commonly share many of the taxa in their intestinal microbiomes (6, 7). Together, this suggests a new hypothesis regarding a different type of candidate transmissible agent(s) in Lupus pathogenesis.

The disease concordance in genetically dissimilar spouses implicates shared close personal environmental exposures. It is postulated that the community of bacterial commensals that we all carry within us may provide the largest environmental exposure. In health, this microbiome may include species that can be major determinants of host immune activation thresholds. In susceptible hosts, some of these commensals may also contribute to autoimmune pathogenesis.

Accelerating advances are illuminating how intestinal microbial communities prime our immune systems and then set overall activation levels (11). Intestinal colonization is required for B-cell development, and the secretion of IgA into the gut lumen (12). In turn this secretory IgA affects the properties and even representation of specific gut bacterial taxa. Notably, some commensal species have been implicated in the pathogenesis of inflammatory and autoimmune diseases, and been termed pathogenic symbionts or pathobionts. In the mouse, Segmented Filamentous Bacteria (SFB) represents the archetypic example of a common colonizer of the small intestine that aids physiologic immune maturation and development of host immune defenses to pathogens (13, 14). However, in predisposed murine strains, SFB colonization can trigger the onset of a range of autoimmune diseases (11). In humans, GI tract colonization with *Helicobacter pylori* is generally innocuous, and it may protect from esophageal cancer (15). Yet this common commensal species can cause peptic ulcer disease, which at one time was the most common indication for abdominal surgery. *H. pylori* infections also contributes to the development of some cases of marginal zone lymphoma (16), which remits with antibiotic treatment.

Advances in culture-independent surveys now enable massive high-throughput 16S ribosomal gene sequence determinations (17, 18). Studies in inflammatory bowel disease (IBD) patients have detected lower microbial diversity and greater temporal instability compared to controls (19), which reflects imbalances (or dysbioses) in their gut microbiomes (20), but this might be expected as the bowel itself is diseased.

In clinical rheumatology, intestinal blooms of the anaerobe, *Prevotella copri*, have been reported at onset of symptomatic seropositive rheumatoid arthritis (RA) (21). There is, however, sparse literature on the microbiome in human Lupus. Although, there are reports on a cohort of 20 female SLE patients (22), but these women were without active disease at the time of sampling. Thus, conceptually, this may be like looking for a disease-associated microbiome in a twin who has never had SLE disease.

SLE affects an estimated 1.5 million Americans (80). Yet all too often treatment options are inadequate to arrest disease progression, and, in general these treatments are highly immunosuppressive and are responsible for high frequencies of serious and often fatal infections (81). Moreover, SLE can lead to complications such as lupus nephritis, which is an immune mediated inflammatory disease of the kidneys. Lupus nephritis can be life-threatening and/or result in renal failure. Definitive diagnosis may require a renal biopsy, which is expensive and associated with defined morbidity and complications. Moreover, delays in Lupus nephritis diagnosis puts the patient at further risk for progression of renal disease, and the associated morbidity, complicating illnesses and premature mortality. There are financial costs that are associated with this increased morbidity, disability, and premature death. These affect individuals, families, communities, and our society in general. Thus, there remains a need for methods for earlier and more accurate diagnosing, treating, and preventing conditions such as SLE and/or lupus nephritis, such as methods and treatments based on or related to the gut microbiome, including associated antigens.

SUMMARY OF THE INVENTION

In one aspect, the invention provides a method for determining whether a subject diagnosed with systemic lupus erythematosus (SLE) or incomplete lupus (ILE) is at an increased risk for developing lupus nephritis, progression of SLE, and/or complications of lupus comprising:

(a) determining in a bodily fluid sample collected from the subject a level of antibodies which recognize a bacterial lipoglycan-containing antigen or a derivative thereof, (b) comparing the level of the antibodies determined in step (a) to a control level of said antibodies, and (c) determining that the subject is at an increased risk for developing lupus nephritis, progression of SLE, and/or complications of lupus if the level of the antibodies determined in step (a) is statistically significantly higher than the control level.

In one embodiment of the above method, the subject has been diagnosed with systemic lupus erythematosus (SLE) or incomplete lupus (ILE) by determining a level of antibodies which recognize an antigen selected from double-stranded DNA (dsDNA), C1q, glomerular extract, nucleosomes, Smith Antibody (Sm), U1RNP, Ro/SSA, La/SSB, and histone(s). In one embodiment of the above method, the subject has been diagnosed with systemic lupus erythematosus (SLE) or incomplete lupus (ILE) by determining a serum level of one or more complement components (e.g., C1q, C3, C4, CH50, or C-reactive protein (CRP)). In one embodiment of the above method, the subject has been diagnosed with systemic lupus erythematosus (SLE) or incomplete lupus (ILE) by determining erythrocyte sedimentation rate (ESR). In one embodiment of the above method, the subject has been diagnosed with systemic lupus erythematosus (SLE) or incomplete lupus (ILE) using an assessment selected from SLE Disease Activity Index (SLEDAI), SLEDAI modified by the Safety of Estrogens in Lupus Erythematosus National Assessment trial (SELENA-SLEDAI), British Isles Lupus Activity Group (BILAG) assessment, the SLAM index, American College of Rheumatology (ACR) SLE classification criteria, and Systemic Lupus Collaborating Clinics (SLICC) criteria.

In another aspect, the invention provides a method for determining whether a subject has systemic lupus erythematosus (SLE) and/or lupus nephritis comprising:

(a) determining in a bodily fluid sample collected from the subject a level of antibodies which recognize a bacterial lipoglycan-containing antigen or a derivative thereof, (b) comparing the level of the antibodies determined in step (a) to a control level of said antibodies, and (c) determining that the subject has SLE and/or lupus nephritis if the level of the antibodies determined in step (a) is statistically significantly higher than the control level.

In a further aspect, the invention provides a method for determining whether a subject has IgA nephropathy or a related renal condition (e.g., Henoch Schonlein Purpura (HSP)) comprising:

(a) determining in a bodily fluid sample collected from the subject a level of antibodies which recognize a bacterial lipoglycan-containing antigen or a derivative thereof, (b) comparing the level of the antibodies determined in step (a) to a control level of said antibodies, and (c) determining that the subject has IgA nephropathy or a related renal condition if the level of the antibodies determined in step (a) is statistically significantly higher than the control level.

In yet another aspect, the invention provides a method for determining whether a subject has a glomerulonephritis or is at an increased risk for developing a glomerulonephritis comprising:

(a) determining in a bodily fluid sample collected from the subject a level of antibodies which recognize a bacterial lipoglycan-containing antigen or a derivative thereof, (b) comparing the level of the antibodies determined in step (a) to a control level of said antibodies, and (c) determining that the subject has a glomerulonephritis or is at an increased risk for developing a glomerulonephritis if the level of the antibodies determined in step (a) is statistically significantly higher than the control level.

In one embodiment of any of the above methods, the subject has proteinuria.

In another aspect, the invention provides a method for determining whether a subject has an inflammatory bowel disease (IBD) comprising:

(a) determining in a bodily fluid sample collected from the subject a level of antibodies which recognize a bacterial lipoglycan-containing antigen or a derivative thereof, (b) comparing the level of the antibodies determined in step (a) to a control level of said antibodies, and (c) determining that the subject has IBD if the level of the antibodies determined in step (a) is statistically significantly higher than the control level.

In one embodiment of the above method, the inflammatory bowel disease (IBD) is ulcerative colitis or Crohn's disease.

In a further aspect, the invention provides a method for monitoring changes in development of a disorder in a subject, which method comprises:

(a) determining in two or more bodily fluid samples collected from the subject at spaced apart time points a level of antibodies which recognize a bacterial lipoglycan-containing antigen or a derivative thereof, (b) comparing the level of the antibodies determined in step (a) between the earlier collected and later collected sample(s), and (c) (i) determining that the disorder in the subject has progressed if the level of the antibodies determined in step (a) is increased in the later collected sample(s) as compared to the earlier collected sample(s), or (ii) determining that the disorder in the subject has not progressed if the level of the antibodies determined in step (a) is not increased in the later collected bodily fluid sample(s) as compared to the earlier collected sample(s).

In another aspect, the invention provides a method for monitoring the effect of a treatment on development of a disorder in a subject, which method comprises:

(a) determining in a bodily fluid sample collected from the subject prior to initiation of the treatment a level of antibodies which recognize a bacterial lipoglycan-containing antigen or a derivative thereof, (b) determining a level of said antibodies in a bodily sample collected from the subject in the course of or following the treatment, (c) comparing the level of the antibodies determined in steps (a) and (b), and (d) (i) determining that the treatment is effective for said disorder if the level of the antibodies determined in step (b) is not higher than the level of the antibodies determined in step (a), or (ii) determining that the treatment is not effective for said disorder if the level of the antibodies determined in step (b) is higher than the level of the antibodies determined in step (a).

In one embodiment of the above two methods, the disorder is selected from an inflammatory bowel disease (IBD) (e.g., ulcerative colitis or Crohn's disease), systemic lupus erythematosus (SLE), incomplete lupus (ILE), lupus nephritis, complications of SLE, IgA nephropathy, Henoch Schonlein Purpura (HSP), and other types of glomerulonephritis.

In one embodiment of any of the above methods, the lipoglycan derivative is a fragment thereof.

In one embodiment of any of the above methods, the lipoglycan-containing antigen or derivative thereof comprises glycerol phosphate.

In one embodiment of any of the above methods, the lipoglycan-containing antigen or derivative thereof is associated with a strain of *Ruminococcus gnavus*. In one specific embodiment, the strain of *Ruminococcus gnavus* is *Ruminococcus gnavus* strain CC55_001C, HM-1056 (Human Microbiome Project (HMP) ID 1201; GenBank: AZJF00000000). In another specific embodiment, the strain of *Ruminococcus gnavus* has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA.

In a further aspect, the invention provides a method for determining whether a subject diagnosed with systemic lupus erythematosus (SLE) or incomplete lupus (ILE) is at an increased risk for developing lupus nephritis, progression of SLE, and/or complications of lupus comprising:

(a) determining in a bodily fluid sample collected from the subject a level of antibodies which recognize a bacterial antigen from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000), (b) comparing the level of the antibodies determined in step (a) to a control level of said antibodies, and (c) determining that the subject is at an increased risk for developing lupus nephritis, progression of SLE, and/or complications of lupus if the level of the antibodies determined in step (a) is statistically significantly higher than the control level.

In one embodiment of the above method, the subject has been diagnosed with systemic lupus erythematosus (SLE) or incomplete lupus (ILE) by determining a level of antibodies which recognize an antigen selected from double-stranded DNA (dsDNA), C1q, glomerular extract, nucleosomes, Smith Antibody (Sm), U1RNP, Ro/SSA, La/SSB, and histone(s). In one embodiment of the above method, the subject has been diagnosed with systemic lupus erythematosus (SLE) or incomplete lupus (ILE) by determining a serum level of one or more complement components (e.g., C1q, C3, C4, CH50, or C-reactive protein (CRP)). In one embodiment of the above method, the subject has been diagnosed with systemic lupus erythematosus (SLE) or incomplete lupus (ILE) by determining erythrocyte sedimentation rate (ESR). In one embodiment of the above method, the subject has been diagnosed with systemic lupus erythematosus (SLE) or incomplete lupus (ILE) using an assessment selected from SLE Disease Activity Index (SLEDAI), SLE-DAI modified by the Safety of Estrogens in Lupus Erythematosus National Assessment trial (SELENA-SLEDAI), British Isles Lupus Activity Group (BILAG) assessment, the SLAM index, American College of Rheumatology (ACR) SLE classification criteria, and Systemic Lupus Collaborating Clinics (SLICC) criteria.

In another aspect, the invention provides a method for determining whether a subject has systemic lupus erythematosus (SLE) and/or lupus nephritis comprising:

(a) determining in a bodily fluid sample collected from the subject a level of antibodies which recognize a bacterial antigen from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000), (b) comparing the level of the antibodies determined in step (a) to a control level of said antibodies, and (c) determining that the subject has SLE and/or lupus nephritis if the level of the antibodies determined in step (a) is statistically significantly higher than the control level.

In yet another aspect, the invention provides a method for determining whether a subject has IgA nephropathy or a related renal condition (e.g., Henoch Schonlein Purpura (HSP)) comprising:

(a) determining in a bodily fluid sample collected from the subject a level of antibodies which recognize a bacterial antigen from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000), (b) comparing the level of the antibodies determined in step (a) to a control level of said antibodies, and (c) determining that the subject has IgA nephropathy or a related renal condition if the level of the antibodies determined in step (a) is statistically significantly higher than the control level.

In a further aspect, the invention provides a method for determining whether a subject has a glomerulonephritis or is at an increased risk for developing a glomerulonephritis comprising:

(a) determining in a bodily fluid sample collected from the subject a level of antibodies which recognize a bacterial antigen from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000), (b) comparing the level of the antibodies determined in step (a) to a control level of said antibodies, and (c) determining that the subject has a glomerulonephritis or is at an increased risk for developing a glomerulonephritis if the level of antibodies determined in step (a) is statistically significantly higher than the control level.

In one embodiment of any of the above methods the subject has proteinuria.

In another aspect, the invention provides a method for determining whether a subject has an inflammatory bowel disease (IBD) comprising:

(a) determining a level of antibodies which recognize a bacterial antigen from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000), in a bodily fluid sample collected from the subject, (b) comparing the level of the antibodies determined in step (a) to a control level of said antibodies, and (c) determining that the subject has IBD if the level of the antibodies determined in step (a) is statistically significantly higher than the control level.

In one embodiment of the above method, the inflammatory bowel disease (IBD) is ulcerative colitis or Crohn's disease.

In another aspect, the invention provides a method for monitoring changes in development of a disorder in a subject, which method comprises:

(a) determining in two or more bodily fluid samples collected from the subject at spaced apart time points a level of antibodies which recognize a bacterial antigen from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000), (b) comparing the level of the antibodies determined in step (a) between the earlier collected and later collected sample(s), and (c) (i) determining that the disorder in the subject has progressed if the level of the antibodies determined in step (a) is increased in the later collected sample(s) as compared to the earlier collected sample(s), or (ii) determining that the disorder in the subject has not progressed if the level of the antibodies determined in step (a) is not increased in the later collected bodily fluid sample(s) as compared to the earlier collected sample(s).

In yet another aspect, the invention provides a method for monitoring the effect of a treatment on development of a disorder in a subject, which method comprises:

(a) determining in a bodily fluid sample collected from the subject prior to initiation of the treatment a level of antibodies which recognize a bacterial antigen from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000), (b) determining in a bodily fluid sample collected from the subject in the course of or following the treatment a level of antibodies which recognize a bacterial antigen from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000), (c) comparing the level of the antibodies determined in steps (a) and (b), and (d) (i) determining that the treatment is effective for said disorder if the level of the antibodies determined in step (b) is not higher than the level of the antibodies determined in step (a), or (ii) determining that the treatment is not effective for said disorder if the level of the antibodies determined in step (b) is higher than the level of the antibodies determined in step (a).

In one embodiment of the above two methods, the disorder is selected from an inflammatory bowel disease (IBD), systemic lupus erythematosus (SLE), incomplete lupus (ILE) lupus nephritis, complications of SLE, IgA nephropathy, Henoch Schonlein Purpura (HSP), and other types of glomerulonephritis.

In one embodiment of any of the above methods involving the bacterial antigen, the bacterial antigen is a non-protein non-nucleic acid antigen. In one embodiment, the non-protein non-nucleic acid bacterial antigen is obtained by treating a culture of said bacteria with a lysozyme, a nuclease, and a protease. In one specific embodiment, the non-protein non-nucleic acid bacterial antigen is obtained using the steps of:

(a) culturing *Ruminococcus gnavus* strain CC55_001C, HM-1056 (Human Microbiome Project (HMP) ID 1201; GenBank: AZJF00000000) at 37° C. under anaerobic conditions for 2-7 days, and (b) producing bacterial extract in the presence of lysozyme, *Serratia marcescens* endonuclease, Proteinase K, and a detergent under non-denaturing conditions.

In one specific embodiment, the non-protein non-nucleic acid bacterial antigen is obtained using the steps of:

(a) culturing *Ruminococcus gnavus* strain CC55_001C, HM-1056 (Human Microbiome Project (HMP) ID 1201; GenBank: AZJF00000000) in rich nutrient media at 37° C. under anaerobic conditions (75% $N_2$, 20% $CO_2$, and 5% $H_2$) for 2-7 days;

(b) pelleting bacteria by centrifugation;

(c) producing bacterial extract in a protein extraction buffer in the presence of lysozyme, *Serratia marcescens* endonuclease, and a detergent under non-denaturing conditions;

(d) treating the extract obtained in step (c) with Proteinase K;

(e) incubating the mixture at 55° C. for about 10 minutes;

(f) removing cell debris by centrifugation, and (g) using the supernatant as the antigen preparation.

In one embodiment of any of the above methods involving the bacterial antigen, the bacterial antigen is obtained using the steps of:

(a) cell disruption with a French press, (b) ultracentrifugation to remove the precipitate, (c) subjecting ultracentrifugation supernatant obtained in step (b) to butanol-water extraction and isolating the aqueous phase, (d) applying the aqueous phase from step (c) to a hydrophobic interaction chromatography matrix (e.g., Octyl-Sepharose CL-4B), and (e) isolating lipoglycan-containing fractions.

In one embodiment of any of the above methods involving the bacterial antigen, the bacterial antigen is a bacterial cell wall antigen.

In one embodiment of any of the above methods, the antibodies are IgG antibodies.

In one embodiment of any of the above methods, the antibodies are IgA antibodies.

In one embodiment of any of the above methods, the level of antibodies is determined using an assay selected from a bead-based assay, an enzyme-linked immunosorbent assay (ELISA), a radioimmunoassay, and Western blotting. In one specific embodiment, the lipoglycan-containing antigen or derivative thereof or the bacterial antigen is coated onto a bead or onto the surface of an ELISA plate or another solid phase used for detection.

In one embodiment of any of the above methods, the bodily fluid is selected from whole blood, plasma, serum, urine, and saliva. In one specific embodiment, the bodily fluid is plasma or serum.

In one embodiment of any of the above methods, the control level of antibodies is selected from (i) a predetermined standard, (ii) the level in a similarly prepared sample obtained from the same subject in the past, and (iii) the level in a similarly prepared sample obtained from a healthy unaffected subject or a mean value of several unaffected healthy subjects. In one specific embodiment, the predetermined standard is a value which represents a statistically validated threshold ratio of the levels of said antibodies equal to the mean value within the range of corresponding values in a large cohort of healthy unaffected subjects.

In one embodiment of any of the above methods, in step (c), the level of the antibodies is determined to be statistically significantly higher than the control level if said level is higher than the mean value calculated for at least 40 unaffected healthy subjects plus three standard deviations.

In another aspect, the invention provides a method for determining whether a subject diagnosed with systemic lupus erythematosus (SLE) or incomplete lupus (ILE) is at an increased risk for developing lupus nephritis, progression of SLE, and/or complications of lupus comprising:

(a) determining in the gastrointestinal (GI) microbiota sample collected from the subject an abundance of bacteria from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000), or another bacterial strain that produces a lipoglycan-containing antigen or a derivative thereof and shares one or more antigenic determinants with *Ruminococcus gnavus* strain CC55_001C, HM-1056, (b) comparing the abundance of bacteria determined in step (a) to a control abundance of said bacteria, and (c) determining that the subject is at an increased risk for developing lupus nephritis, progression of SLE, and/or complications of lupus if the abundance of bacteria determined in step (a) is statistically significantly higher than the control abundance.

In one embodiment of the above method, the subject has been diagnosed with systemic lupus erythematosus (SLE) or incomplete lupus (ILE) by determining a level of antibodies which recognize an antigen selected from double-stranded DNA (dsDNA), C1q, glomerular extract, nucleosomes, Smith Antibody (Sm), U1RNP, Ro/SSA, La/SSB, and histone(s). In one embodiment of the above method, the subject has been diagnosed with systemic lupus erythematosus (SLE) or incomplete lupus (ILE) by determining a serum level of one or more complement components (e.g., C1q, C3, C4, CH50, or C-reactive protein (CRP)). In one embodiment of the above method, the subject has been diagnosed with systemic lupus erythematosus (SLE) or incomplete lupus (ILE) by determining erythrocyte sedimentation rate (ESR). In one embodiment of the above method, the subject has been diagnosed with systemic lupus erythematosus (SLE) or incomplete lupus (ILE) using an assessment selected from SLE Disease Activity Index (SLEDAI), SLE-DAI modified by the Safety of Estrogens in Lupus Erythematosus National Assessment trial (SELENA-SLEDAI), British Isles Lupus Activity Group (BILAG) assessment, the SLAM index, American College of Rheumatology (ACR) SLE classification criteria, and Systemic Lupus Collaborating Clinics (SLICC) criteria.

In yet another aspect, the invention provides a method for determining whether a subject has systemic lupus erythematosus (SLE) and/or lupus nephritis comprising:

(a) determining in the gastrointestinal (GI) microbiota sample collected from the subject an of bacteria from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000), or another bacterial strain that produces a lipoglycan-containing antigen or a derivative thereof and shares one or more antigenic determinants with *Ruminococcus gnavus* strain CC55_001C, HM-1056, (b) comparing the abundance of bacteria determined in step (a) to a contorl abundance of said bacteria, and (c) determining that the subject has SLE and/or lupus nephritis if the abundance of bacteria determined in step (a) is higher than the control abundance.

In another aspect, the invention provides a method for determining whether a subject has IgA nephropathy or a related renal condition (e.g., Henoch Schonlein Purpura (HSP)) comprising:

(a) determining in the gastrointestinal (GI) microbiota sample collected from the subject an abundance of bacteria from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000), or another bacterial strain that produces a lipoglycan-containing antigen or a derivative thereof and shares one or more antigenic determinants with *Ruminococcus gnavus* strain CC55_001C, HM-1056, (b) comparing the abundance of bacteria determined in step (a) to a control abundance, and (c) determining that the subject has an IgA nephropathy or a related renal condition if the abundance of bacteria determined in step (a) is statistically significantly higher than the control abundance.

In a further aspect, the invention provides a method for determining whether a subject has a glomerulonephritis or is at an increased risk for developing a glomerulonephritis comprising:

(a) determining in the gastrointestinal (GI) microbiota sample collected from the subject an abundance of bacteria from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000), or another bacterial strain that produces a lipoglycan-containing antigen or a derivative thereof and shares one or more antigenic determinants with *Ruminococcus gnavus* strain CC55_001C, HM-1056, (b) comparing the abundance of bacteria determined in step (a) to a control abundance of said bacteria, and (c) determining that the subject has a glomerulonephritis or is at an increased risk for developing a glomerulonephritis if the abundance of bacteria determined in step (a) is statistically significantly higher than the control abundance.

In one embodiment of any of the above methods, the control abundance of bacteria is selected from (i) a predetermined standard, (ii) the abundance in a similarly prepared sample obtained from the same subject in the past, and (iii) the abundance in a similarly prepared sample obtained from a matched healthy subject or an average of several matched healthy subjects. In one specific embodiment, the predetermined standard is a value which represents a statistically validated threshold ratio of the abundance of said bacteria equal to the mean value within the range of corresponding values in a large cohort of healthy unaffected subjects.

In one embodiment of any of the above methods, in step (c), the abundance of said bacteria is determined to be statistically significantly higher than the control abundance if said abundance is higher than the mean value calculated for at least 40 unaffected healthy subjects plus three standard deviations.

In a further aspect, the invention provides a method for monitoring changes in development of a disorder in a subject, which method comprises:

(a) determining in two or more gastrointestinal (GI) microbiota samples collected from the subject at spaced apart time points an abundance of bacteria from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA DNA sequence with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000), or another bacterial strain that produces a lipoglycan-containing antigen or a derivative thereof and shares one or more antigenic determinants with *Ruminococcus gnavus* strain CC55_001C, HM-1056, (b) comparing the abundance of bacteria determined in step (a) between the earlier collected and later collected sample(s), and (c) (i) determining that the disorder in the subject has progressed if the abundance of bacteria determined in step (a) is increased in the later collected sample(s) as compared to the earlier collected sample(s), or (ii) determining that the disorder in the subject has not progressed if the abundance of bacteria determined in step (a) is not increased in the later collected bodily fluid sample(s) as compared to the earlier collected sample(s).

In another aspect, the invention provides a method for monitoring the effect of a treatment on development of a disorder in a subject, which method comprises:

(a) determining in the gastrointestinal (GI) microbiota sample collected from the subject prior to initiation of the treatment an abundance of bacteria from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000), or another bacterial strain that produces a lipoglycan-containing antigen or a derivative thereof and shares one or more antigenic determinants with *Ruminococcus gnavus* strain CC55_001C, HM-1056, (b) determining in the gastrointestinal (GI) microbiota sample collected from the subject in the course of or following the treatment an abundance of the same bacteria, comparing the abundance of bacteria determined in steps (a) and (b), and (c) (i) determining that the treatment is effective for said disorder if the abundance of bacteria determined in step (b) is not higher than the abundance of bacteria determined in step (a), or (ii) determining that the treatment is not effective for said disorder if the abundance of bacteria determined in step (b) is higher than the abundance of bacteria determined in step (a).

In one embodiment of the above two methods, the disorder is selected from systemic lupus erythematosus (SLE), lupus nephritis, IgA nephropathy, complications of SLE, Henoch Schonlein Purpura (HSP), and other types of glomerulonephritis.

In one embodiment of any of the above methods, the abundance of the bacterial strain is identified by a DNA sequencing, RNA sequencing, PCR-based method, microscopy, flow cytometry. In one specific embodiment, the sequencing is high-throughput sequencing of one or more genes selected from 16S rDNA, LtaS, TagB, TagF, TagE, TagG, TagH, TagH, RumA, and RumC to identify the abundance of the strain-specific nucleic acid sequence(s).

In one embodiment of any of the above methods, the GI microbiota is cecal, ileal, colonic, or fecal microbiota. In one specific embodiment, the GI microbiota is fecal microbiota.

In one embodiment of any of the above methods, the V region of 16S rDNA is the V4 region.

In one embodiment of any of the above methods, the lupus nephritis is proliferative lupus nephritis, membranous lupus nephritis, membranoproliferative lupus nephritis, or mesangial glomerulonephritis.

In one embodiment of any of the above methods, the glomerulonephritis is active glomerulonephritis.

In one embodiment of any of the above methods, the level of antibodies or abundance of bacteria in step (a) is determined in two or more samples obtained from the subject at about the same time and a mean level or abundance is determined and compared to the control. In one embodiment of any of the above methods, the level of antibodies or abundance of bacteria is determined in two or more samples obtained from the subject for each of the time points and a mean level or abundance for each time point is determined and compared. In one embodiment of any of the above methods, the method further comprises determining in a bodily fluid sample collected from the subject a level of antibodies which recognize an antigen selected from double-stranded DNA (dsDNA), C1q, glomerular extract, nucleosomes, Smith Antibody (Sm), U1RNP, Ro/SSA, La/SSB, and histone(s). In one specific embodiment, the level of antibodies is determined using a method selected from enzyme-linked immunosorbent assay (ELISA), *Crithidia luciliae* immunofluorescence test, radioimmunoassay, counterimmunoelectrophoreses (CIE), immunodiffusion, Western blotting, bead based assays, and hemagglutination. In one specific embodiment, the level of the antibodies which recognize said additional antigen is determined in the same sample as the level of the antibodies which recognize lipoglycan-containing antigen or derivative thereof or the bacterial antigen.

In one embodiment of any of the above methods, the method further comprises determining serum level(s) of one or more complement components. In one specific embodiment, the complement component is selected from C1q, C3, C4, CH50 and C-reactive protein (CRP).

In one embodiment of any of the above methods, the method further comprises determining erythrocyte sedimentation rate (ESR).

In one embodiment of any of the above methods, the method further comprises conducting an assessment of the subject by determining one or more parameters selected from gut permeability, SLE Disease Activity Index (SLEDAI), SLEDAI modified by the Safety of Estrogens in Lupus Erythematosus National Assessment trial (SELENA-SLEDAI), British Isles Lupus Activity Group (BILAG) assessment, the SLAM index, American College of Rheumatology (ACR) SLE classification criteria, and Systemic Lupus Collaborating Clinics (SLICC) criteria.

In one embodiment of any of the above methods, the method further comprises a kidney assessment. In one specific embodiment, the kidney assessment comprises urinalysis. In one specific embodiment, the urinalysis comprises determining the level of protein and/or red blood cells in the urine, and wherein the increased level of protein or red blood cells as compared to a relevant control is indicative of a kidney disease.

In one embodiment of any of the above methods, the method further comprises recruiting the subject in a clinical trial.

In one embodiment of any of the above methods, the method further comprises administering a therapeutic or preventive treatment to the subject. In one specific embodiment, the treatment results in a decrease in the level of the antibodies which recognize said lipoglycan-containing antigen or derivative thereof or said bacterial antigen.

In a further aspect, the invention provides a method of treating a disorder in a subject in need thereof, wherein the disorder is selected from inflammatory bowel disease (IBD), systemic lupus erythematosus (SLE), incomplete lupus (ILE) lupus nephritis, IgA nephropathy, Henoch Schonlein Purpura (HSP), and other types of glomerulonephritis, said method comprising administering to the subject an effective amount of a compound or composition which promotes a decrease in the level of antibodies which recognize a bacterial lipoglycan-containing antigen or a derivative thereof in a bodily fluid of said subject.

In one embodiment of the above method, the lipoglycan derivative is a fragment thereof.

In one embodiment of the above method, the lipoglycan-containing antigen or derivative thereof comprises glycerol phosphate.

In one embodiment of the above method, the lipoglycan-containing antigen or derivative thereof is associated with a strain of *Ruminococcus gnavus*. In one specific embodiment, the strain of *Ruminococcus gnavus* is *Ruminococcus gnavus* strain CC55_001C, HM-1056 (Human Microbiome Project (HMP) ID 1201; GenBank: AZJF00000000). In one specific embodiment, the strain of *Ruminococcus gnavus* has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA.

In another aspect, the invention provides a method of treating a disorder in a subject in need thereof, wherein the disorder is selected from inflammatory bowel disease (IBD), systemic lupus erythematosus (SLE), incomplete lupus (ILE), lupus nephritis, IgA nephropathy, Henoch Schonlein Purpura (HSP), and other types of glomerulonephritis, said method comprising administering to the subject an effective amount of a compound or composition which promotes a decrease in the level of antibodies in a bodily fluid of said subject, wherein said antibodies recognize a bacterial antigen from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000).

In one embodiment of the above method, the bacterial antigen is a non-protein non-nucleic acid bacterial antigen. In one embodiment, the non-protein non-nucleic acid bacterial antigen is obtained by treating a culture of said bacteria with a lysozyme, a nuclease, and a protease. In one specific embodiment, the non-protein non-nucleic acid bacterial antigen is obtained using the steps of:

(a) culturing *Ruminococcus gnavus* strain CC55_001C, HM-1056 (Human Microbiome Project (HMP) ID 1201; GenBank: AZJF00000000) at 37° C. under anaerobic conditions for 2-7 days, and (b) producing bacterial extract in the presence of lysozyme, *Serratia marcescens* endonuclease, Proteinase K, and a detergent under non-denaturing conditions.

In one specific embodiment, said non-protein non-nucleic acid bacterial antigen is obtained using the steps of:

(a) culturing *Ruminococcus gnavus* strain CC55_001C, HM-1056 (Human Microbiome Project (HMP) ID 1201; GenBank: AZJF00000000) in rich nutrient media at 37° C. under anaerobic conditions (75% $N_2$, 20% $CO_2$, and 5% $H_2$) for 2-7 days;

(b) pelleting bacteria by centrifugation;

(c) producing bacterial extract in a protein extraction buffer in the presence of lysozyme, *Serratia marcescens* endonuclease, and a detergent under non-denaturing conditions;

(d) treating the extract obtained in step (c) with Proteinase K;

(e) incubating the mixture at 55° C. for about 10 minutes;

(f) removing cell debris by centrifugation, and (g) using the supernatant as the antigen preparation.

In one embodiment of the above method, the bacterial antigen is obtained using the steps of:

(a) cell disruption with a French press, (b) ultracentrifugation to remove the precipitate, (c) subjecting ultracentrifugation supernatant obtained in step (b) to butanol-water extraction and isolating the aqueous phase, (d) applying the aqueous phase from step (c) to a hydrophobic interaction chromatography matrix (e.g., Octyl-Sepharose CL-4B), and (e) isolating lipoglycan-containing fractions.

In one embodiment of the above method, the bacterial antigen is a bacterial cell wall antigen.

In one embodiment of the above method, said treatment comprises administering to the subject an effective amount of a compound that binds and neutralizes said lipoglycan-containing antigen or derivative thereof or said bacterial antigen or aids the clearance thereof from the gastrointestinal (GI) tract. In one specific embodiment, the compound is an antibody or a functional fragment thereof (e.g., an IgA antibody produced by a diary animal). In one embodiment, said compound or antibody is administered orally or per rectum.

In one embodiment of the above method, said treatment comprises mucosal immunization with said lipoglycan-containing antigen or derivative thereof or said bacterial antigen.

In one embodiment of the above method, said treatment comprises administering to the subject an effective amount of one or more compounds selected from a macrophage scavenger receptor protein (MSRP); a fragment of MSRP, wherein said fragment is capable of binding to said lipoglycan-containing antigen or derivative thereof; gelsolin; a peptide comprising the amino acid sequence of the C-terminal helix of apolipoprotein CI (apoCI); daptomycin; activated charcoal; kaolinite; kaopectate; a cationic peptide; a phospholipid; a polysulphate; an endogenous binding protein; and a functional domain of a ficolin protein.

In one embodiment of the above method, said treatment comprises administering to the subject an effective amount of a compound that inhibits biosynthesis of said lipoglycan-containing antigen or derivative thereof or of said bacterial antigen.

In one embodiment of the above method, the treatment results in a decrease in the GI microbiota of the subject of the abundance of bacteria from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000).

In a further aspect, the invention provides a method of treating a disorder in a subject in need thereof, wherein the disorder is selected from systemic lupus erythematosus (SLE), incomplete lupus (ILE) lupus nephritis, IgA nephropathy, Henoch Schonlein Purpura (HSP), and other types of glomerulonephritis, said method comprising administering to the subject an effective amount of a compound or composition which promotes a decrease in the GI microbiota of the subject of the abundance of bacteria from *Ruminococcus gnavus* strain CC55_001C, HM-1056 (Human Microbiome Project (HMP) ID 1201; GenBank: AZJF00000000) or a strain from Lachnospiraceae family, wherein said strain has 16S rDNA with at least 95% sequence identity to the 16S rDNA of *Ruminococcus gnavus* strain CC55_001C, HM-1056 (Human Microbiome Project (HMP) ID 1201; GenBank: AZJF00000000) over its entire length or at least 99% sequence identity to any single V region of the 16S rDNA of *Ruminococcus gnavus* strain CC55_001C, HM-1056 (Human Microbiome Project (HMP) ID 1201; GenBank: AZJF00000000).

In one embodiment, the treatment comprises administering to the subject an effective amount of an antibiotic which inhibits growth or activity of said bacteria in the GI microbiota of said subject. In one specific embodiment, the antibiotic is penicillin.

In one embodiment, the treatment comprises administering an effective amount of a probiotic and/or prebiotic composition which inhibits growth or activity of said bacteria in the GI microbiota of said subject. In one specific embodiment, said probiotic composition comprises a preparation transplant of the GI microbiota of a healthy subject. In one specific embodiment, said probiotic composition comprises a consortium of commensal bacteria. In one specific embodiment, said probiotic and/or prebiotic composition stimulates growth and/or activity of one or more strains of bacteria from the species *Faecalibacterium prausnitzii* and/or species *Bacteroides uniformis* and/or genus *Akkermansia* and/or genus *Lactobacillus* in the GI microbiota of the subject. In one specific embodiment, the method comprises administering to the subject one or more strains from the species *Faecalibacterium prausnitzii* and/or species *Bacteroides uniformis* and/or genus *Akkermansia* and/or genus *Lactobacillus*. In one specific embodiment, said probiotic composition comprises one or more components selected from live bacterial cells, spores, conditionally lethal bacterial cells, inactivated bacterial cells, killed bacterial cells, recombinant carrier strains, cell extract, and bacterially-derived products. In one specific embodiment, said probiotic and/or prebiotic composition is administered by a route selected from oral, rectal, and via naso/oro-gastric gavage.

In one embodiment of the above treatment methods, the inflammatory bowel disease (IBD) is ulcerative colitis or Crohn's disease.

In one embodiment of the above treatment methods, the method further comprises administering to the subject an additional treatment. In one specific embodiment, the disorder is systemic lupus erythematosus (SLE) incomplete lupus (ILE), or lupus nephritis and the additional treatment comprises administering an effective amount of one or more compounds selected from anti-inflammatory drugs (NSAIDs), antimalarial agents (e.g., hydroxychloroquine), corticosteroids (e.g., prednisone, hydrocortisone, prednisolone, or dexamethasone), azathioprine, mycophenolate, methotrexate, leflunomide, belimumab, and Vitamin D.

In one embodiment of any of the above methods, the bodily fluid is selected from whole blood, plasma, serum, urine, and saliva.

In one embodiment of any of the above methods, the subject is human.

In one embodiment of any of the above methods, the subject is a veterinary animal.

In one embodiment of any of the above methods, the complication of lupus involves the pulmonary system, central nervous system, cardiovascular system, skin disease, joint disease, musculoskeletal disease, depressed red cell levels, depressed white cell levels, depressed platelets, immunosuppression, severe infection, or any combination thereof.

These and other aspects of the present invention will be apparent to those of ordinary skill in the art in the following description, claims and drawings.

BRIEF DESCRIPTION OF THE DRAWINGS

This patent application file contains at least one drawing executed in color. Copies of this patent application with color drawing(s) will be provided by the Office upon request and payment of the necessary fee.

DETAILED DESCRIPTION

Figure 1:
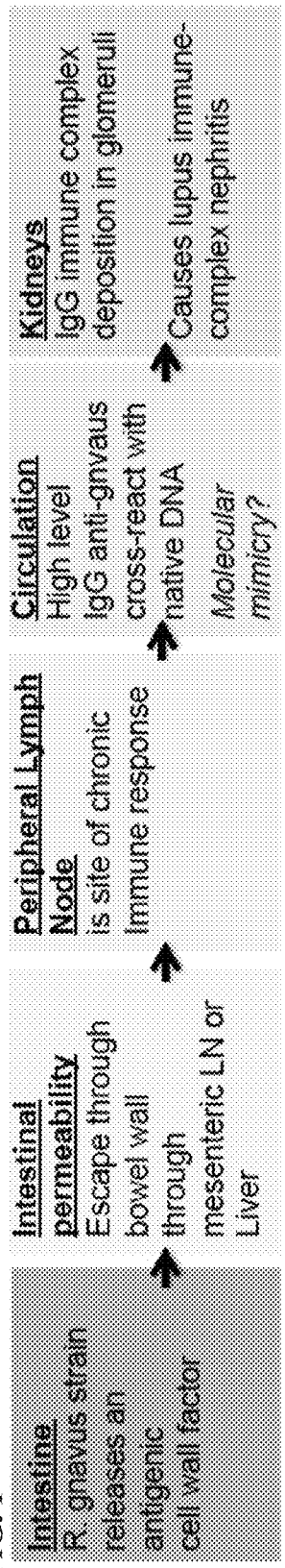
FIG. 1. Mechanistic model for renal disease in Lupus patients induced by HM-1056, also termed CC55_001C, strain of R. gnavus of the Lachnospiraceae family of commensal gram-positive anaerobe.

The present invention provides methods and compositions for diagnosing and treating (including preventing) autoimmune and/or inflammatory disease such as systemic lupus erythematosus (SLE), incomplete lupus (ILE) syndrome, lupus nephritis, glomerulonephritis (e.g., IgA nephropathy) and inflammatory bowel disease (IBD) (e.g., ulcerative colitis and Crohn's disease). Therapeutic methods of the invention involve the use of compounds or compositions, including probiotic and prebiotic compositions.

SLE is a chronic inflammatory autoimmune disease with hallmarks of B-cell abnormalities and clonal expansions, in which circulating autoantibodies and immune-complexes mediate tissue injury. SLE can lead to complications such as lupus nephritis, which is an inflammation of the kidneys. Lupus nephritis can be life-threatening and/or result in renal failure. Before the present invention, a diagnosis of lupus nephritis may require a renal biopsy, which is expensive and associated with the possibility of morbidity and complications.

The present invention is based on the surprising discovery that SLE patients have recurrent patterns of dysbioses in their intestinal microbiomes. For example, patients in remission off medications (and low SLEDAI scores) (see FIG. 2A), have intestinal communities that can be similar to a healthy gender/age-matched individual (see FIG. 2B). In contrast, in patients with greater disease severity these imbalances are generally more severe.

Based on subsetting by disease activity, it was found that a patient with higher disease activity generally displayed progressive increases in the representation of an anaerobic Gram-positive cocci species (based on 16S rDNA gene sequence) that was identified as a taxon termed *Ruminococcus gnavus*, which has been reassigned from the Ruminococcaceae family to the Lachnospiraceae family due in part to its active fermentative ability. *R. gnavus*, however, has retained its name. This species is a common commensal, and up to 90% of healthy adults have detectable *R. gnavus* (25); it was found that the relative abundance of this species is increased in SLE patients with high disease activity.

As lupus nephritis is a major source of early mortality and overall morbidity, a blood test that provides a substantial increase in confidence in the diagnosis of Lupus nephritis would therefore be predicted to provide both medical and economic advantages. Performing the blood test herein described would in itself have only very minor medical risks associated with peripheral blood draw.

At present it is not certain about whether patients develop the autoimmune disease, SLE, and then may become colonized with a nephritogenic strain of R. gnavus that then contributes to pathogenesis. Renal effects might then be lessened or avoided entirely if this is the natural sequence in the progression of Lupus, and we could remove this bacterial strain and its pathogenic influence on the course of this disease. Alternatively, it may be that gut colonization with this nephritogenic strain may lead to a diagnosis of SLE, and concurrent or subsequent glomerulonephritis. Thus, treatment in advance for those at risk of developing SLE or Lupus nephritis would be beneficial.

The methods and treatments herein can also be useful in diagnosing and/or treating inflammatory diseases, such as, but not limited to, glomerulonephritis (e.g., IgA nephropathy) and inflammatory bowel disease (IBD) (e.g., ulcerative colitis and Crohn's disease).

IgA nephropathy is a specific pathologic diagnosis that is established at renal biopsy. In certain embodiments, the IgA nephropathy is Henoch Schonlein Purpura (HSP). IgA nephropathy and HSP are no different in the renal biopsy, although the former is more common in adults and the latter in children, teens and young adults. HSP patients do have other diagnostic features outside of the kidneys. Patients with liver disease may have IgA deposits in their kidneys similar or indistinguishable from IgA nephropathy. IgA nephropathy may progress to chronic kidney failure in a subset of cases during a period of 20 years. In part it may be important to make this diagnosis to also rule out other diagnoses with even worse prognoses.

There is no accepted blood test that supports the diagnosis of IgA nephropathy, and there is no accepted blood test that raises the index of suspicion. As a renal biopsy is required to establish the IgA nephropathy diagnosis, diagnosis is often delayed and hence definitive treatment is then delayed and damage to the kidney may accumulate over time. The true incidence of this disease is therefore currently uncertain. Thus, a more accurate and earlier diagnosis of a defined type of glomerulonephritis can facilitate earlier and more specific treatment.

Taken together, the Examples demonstrate a previously unsuspected pathogenetic sequence in which a gut gram-positive commensal may release cell wall components. This can, for example, contribute to SLE immune complex disease (FIG. 1) as well as other autoimmune and/or inflammatory diseases. As further demonstrated herein, a subset of SLE patients have increased gut permeability ("leaky" gut) which, without wishing to be bound by any theory, is postulated to further contribute to this effect due to translocation of bacteria and bacterial components that results in exposure to the systemic immune system. Immunoblot analysis showed Lupus serum IgG recognizes a repetitive oligomeric set of bands visualized at ~22-25 kDa (see FIG. 3). This antigen is also eluted from the bacteria by simple incubation in dH$_2$0, an indicator of cell wall localization. IgG immunoreactivity with this antigenic band complex was unaffected by DNAse, lysozyme, or protease treatment, suggesting that it is a non-protein, non-nucleic acid molecule. It is hypothesized herein that this non-protein, non-nucleic acid antigen comprises a highly immunogenic lipoglycan. The lipoglycan is highly immunogenic and can interact with circulating antibodies to activate the complement cascade and trigger the release from neutrophils and macrophages of reactive oxygen and nitrogen species, and other factors that may act in synergy to amplify cell damage. As demonstrated in the Examples section, this lipoglycan-containing antigen of R. gnavus strain CC55 001C is recognized by a high level of IgG antibodies in many patients with active Lupus nephritis.

It is also possible that bacterial strains may transfer their genetic factors to other strains of the same bacterial species or to related species or even different species. Thus, it is possible the gene set responsible for bacterial production of the renal disease-associated antigen can be transferred to another bacterial species.

The invention disclosed herein will enable earlier diagnosis of and/or therapeutic intervention for patients suffering from one of the most serious aspects of autoimmune diseases such as, but not limited to, SLE and Lupus associated diseases such as Lupus nephritis, and may now lead to specific therapy that should be much safer than modalities that result in therapeutic broad immunosuppression.

The invention disclosed herein will also enable earlier diagnosis of and/or therapeutic intervention for patients suffering from one of the most serious aspects of inflammatory diseases such as, but not limited to, glomerulonephritis (e.g., IgA nephropathy) and inflammatory bowel disease (IBD) (e.g., ulcerative colitis and Crohn's disease), and may lead to specific therapy that should be much safer than broad inflammatory treatment.

Moreover, as disclosed herein, the microbiome can also be used as a biomarker and therapeutic target in autoimmune and inflammatory diseases.

Definitions

As used herein, the terms "microbe" or "microorganism" encompass both prokaryotic organisms including bacteria and archaea, and eukaryotic organisms, including fungi, present as components of the mammalian microbiota, and viruses.

The terms "gastrointestinal microbiota", "GI microbiota", "intestinal microbiota", "intestinal flora", and "intestinal microbiome" are used interchangeably and refer to the microorganisms that colonize the intestines.

As used herein, the term "dysbiosis" refers to a microbial imbalance on or inside the body. Dysbiosis can result from, e.g., antibiotic exposure as well as other causes, e.g., infections with pathogens including viruses, bacteria and eukaryotic parasites.

Specific taxa and changes in GI microbiota discussed herein can be detected using various methods, including without limitation quantitative PCR or high-throughput sequencing methods which detect over- and under-represented genes in the total bacterial population (e.g., sequencing for microbial community analysis (e.g., using a 454 machine or other related devices); screening of microbial 16S ribosomal RNAs (16S rRNA) or microbial 16s ribosomal DNA (16s rDNA), next generation sequencing (NGS) etc.), or transcriptomic or proteomic studies that identify lost (or under-represented) or gained microbial transcripts or proteins within total bacterial populations. See, e.g., U.S. Patent Publication No. 2010/0074872; Eckburg et al., Science, 2005, 308:1635-8; Costello et al., Science, 2009, 326:1694-7; Grice et al., Science, 2009, 324:1190-2; Li et al., Nature, 2010, 464: 59-65; Bjursell et al., Journal of Biological Chemistry, 2006, 281:36269-36279; Mahowald et al., PNAS, 2009, 14:5859-5864; Wikoff et al., PNAS, 2009, 10:3698-3703.

As used herein, the term "16S rDNA sequencing" refers to the sequencing of 16S ribosomal DNA (rDNA) or 16S ribosomal RNA (rRNA) gene sequences by using primers such as universal primers and/or species-specific primers to identify the bacteria present in a sample. rDNA and rRNA genes contain both highly conserved sites and hypervariable regions that can provide species-specific signature sequences useful for identification of bacteria. Such universal primers are well known in the art.

As used herein, the term "operational taxonomic unit" or "OTU" refers to group of bacterial sequences that differ among each other as each shares <97% identity. A "type" or a plurality of "types" of bacteria includes an OTU or a plurality of different OTUs, and also encompasses differences in species, genus, family or order of bacteria. The specific genetic sequence may be the 16S rDNA or rRNA sequence or a portion of the 16S rDNA or rRNA sequence or it may be a functionally conserved housekeeping gene found broadly across the eubacterial kingdom.

As used herein, the term "abundance" refers to how common or rare a particular organism (e.g., bacterial species) is relative to other organisms of the same type (e.g., other bacterial species) in a defined community. In certain embodiments, abundance is the percent composition of a particular organism (e.g., bacterial species) to the total amount of organisms in the sample. In certain embodiments, abundance refers to the total level of organism in a sample. In certain embodiments, abundances are described for a single trophic level.

As used herein, the term "probiotic" refers to a substantially pure bacteria (i.e., a single isolate, of, e.g., live bacterial cells, conditionally lethal bacterial cells, inactivated bacterial cells, killed bacterial cells, spores, recombinant carrier strains), or a mixture of desired bacteria, bacteria components or bacterial extract, or bacterially-derived products (natural or synthetic bacterially-derived products such as, e.g., bacterial antigens or metabolic products) and may also include any additional components that can be administered to a mammal. Such compositions are also referred to herein as bacterial inoculants" or "microbiota inoculants". Probiotics or bacterial inoculant compositions of the invention may be administered with a buffering agent to allow the bacteria to survive in the acidic environment of the stomach, i.e., to resist low pH and to grow in the intestinal environment. Such buffering agents include sodium bicarbonate, juice, milk, yogurt, infant formula, and other dairy products.

As used herein, the term "prebiotic" refers to an agent that increases the number and/or activity of one or more desired bacteria, enhancing their growth. Non-limiting examples of prebiotics useful in the methods of the present invention include fructooligosaccharides (e.g., oligofructose, inulin, inulin-type fructans), galactooligosaccharides, human milk oligosaccharides (HMO), Lacto-N-neotetraose, D-Tagatose, xylo-oligosaccharides (XOS), arabinoxylan-oligosaccharides (AXOS), N-acetylglucosamine, N-acetylgalactosamine, glucose, other five- and six-carbon sugars (such as arabinose, maltose, lactose, sucrose, cellobiose, etc.), amino acids, alcohols, resistant starch (RS), water-soluble cellulose derivatives (most preferably, methylcellulose, methyl ethyl cellulose, hydroxyethyl cellulose, ethyl hydroxyethyl cellulose, cationic hydroxyethyl cellulose, hydroxypropyl cellulose, hydroxyethyl methylcellulose, hydroxypropyl methylcellulose, and carboxymethyl cellulose), water-insoluble cellulose derivatives (most preferably, ethyl cellulose), and mixtures thereof. See, e.g., Ramirez-Farias et al., Br J Nutr (2008) 4:1-10; Pool-Zobel and Sauer, J Nutr (2007), 137: 2580S-2584S.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein, the term "therapeutically effective amount" refers to the amount of a bacterial inoculant, a compound, or a composition, including a prebiotic or a probiotic, that, when administered to a subject for treating (e.g., preventing or ameliorating) a state, disorder or condition, is sufficient to effect such treatment. The "therapeutically effective amount" will vary depending, e.g., on the compound, composition, bacteria or analogues administered as well as the disease, its severity, and physical conditions and responsiveness of the subject to be treated.

As used herein, the phrase "pharmaceutically acceptable" refers to molecular entities and compositions that are generally regarded as physiologically tolerable.

As used herein, the term "combination" of a compound, composition, bacterial inoculant, probiotic, analogue, or prebiotic and at least a second pharmaceutically active ingredient means at least two, but any desired combination of compound, composition, bacterial inoculant, probiotic, analogue, or prebiotic can be delivered simultaneously or sequentially (e.g., within a 24 hour period).

Within the meaning of the present invention, the term "conjoint biotic administration" is used to refer to administration of a probiotic and a prebiotic simultaneously in one composition, or simultaneously in different compositions, or sequentially (preferably, within a 24 hour period).

The terms "patient", "individual", "subject", and "animal" are used interchangeably herein and refer to mammals, including, without limitation, human and veterinary animals (e.g., cats, dogs, cows, horses, goats, sheep, pigs, etc.) and experimental animal models. In a preferred embodiment, the subject is a human.

As used herein, the term "healthy subject" refers to a subject that is without known infections or autoimmune disorders by using conventional diagnostic methods. In certain embodiments, a healthy subject is a subject without a known first degree relative with an autoimmune disorder. In certain embodiments, a matched healthy subject is matched by age, gender, and/or ethnicity.

As used herein, the term "stimulate" when used in connection with growth and/or activity of bacteria encompasses the term "enhance".

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The terms "a," "an," and "the" do not denote a limitation of quantity, but rather denote the presence of "at least one" of the referenced item.

The practice of the present invention employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J. Additional techniques are explained, e.g., in U.S. Pat. No. 7,912,698 and U.S. Patent Appl. Pub. Nos. 2011/0202322 and 2011/0307437.

Diagnostic and Monitoring Methods of the Invention

As specified in the Background section above, there is a great need in the art for diagnosing autoimmune disease such as, but not limited to, systemic lupus erythematosus (SLE), incomplete lupus (ILE) syndrome, and lupus nephritis. There also exists a need in the art for diagnosing inflammatory diseases such as, but not limited to, glomerulonephritis (e.g., IgA nephropathy) and inflammatory bowel disease (IBD) (e.g., ulcerative colitis and Crohn's disease).

Moreover, there exists a need to monitor changes in the development or treatment of autoimmune and/or inflammatory disorders. In certain embodiments, the disorder can be SLE, ILE, lupus nephritis, IgA nephropathy, glomerulonephritis, or inflammatory bowel disease. The different forms of nephropathy/nephritis that may be addressed by the methods disclosed herein are further disclosed in Renal disease: classification and atlas of glomerular diseases/Jacob Churg, Jay Bernstein, Richard J. Glassock. 1995, English, Book, Illustrated edition: 2nd ed. Published New York: Igaku-Shoin, c1995, which is incorporated herein by reference in its entirety and for all purposes as if fully set forth herein.

In certain embodiments, lupus nephritis is proliferative lupus nephritis or membranous lupus nephritis. In certain embodiments, lupus nephritis is membranoproliferative Lupus nephritis. In certain embodiments, lupus nephritis is mesangial glomerulonephritis.

In certain embodiments, the methods involve diagnosis and/or treating or preventing complications involved with lupus. Complication of lupus involves, for example but not limitation, the pulmonary system, central nervous system, cardiovascular system, skin disease, joint disease, musculoskeletal disease, depressed red cell levels, depressed white cell levels, depressed platelets, immunosuppression, severe infection, or any combination thereof.

Glomerulonephritis is a group of diseases that injure the part of the kidney that filters blood (called glomeruli). In certain embodiments, glomerulonephritis can be acute or chronic. The range of glomerulonephritis is disclosed in ICD-10. International Statistical Classification of Diseases and Related Health Problems Tenth Revision. Second Edition, which is incorporated herein by reference in its entirety and for all purposes as if fully set forth herein. In certain embodiments, glomerulonephritis entails an inflammation of either the glomeruli or the small blood vessels of the kidneys. In certain embodiments, glomerulonephritis does not entail inflammation. In certain embodiments, the glomerulonephritis disorder can be caused by certain infections (e.g., bacterial, viral or parasitic pathogens), drugs, systemic disorders (e.g., SLE, vasculitis), or diabetes. In certain embodiments, glomerulonephritis can be IgA nephropathy.

In certain embodiments, the glomerulonephritis is associated with Lupus. The current classification scheme for glomerulonephritis in SLE patients reflects the understanding of the pathogenesis of the various forms of Lupus nephritis, but clinicopathologic studies have revealed the need for improved categorization and terminology. Based on the 1982 classification published under the auspices of the World Health Organization (WHO) and subsequent clinicopathologic data, class I and II refers to purely mesangial involvement (I, mesangial immune deposits without mesangial hypercellularity; II, mesangial immune deposits with mesangial hypercellularity); class III for focal glomerulonephritis (involving <50% of total number of glomeruli) with subdivisions for active and sclerotic lesions; class IV for diffuse glomerulonephritis (involving > or =50% of total number of glomeruli) either with segmental (class IV-S) or global (class IV-G) involvement, and also with subdivisions for active and sclerotic lesions; class V for membranous lupus nephritis; and class VI for advanced sclerosing lesions]. Combinations of membranous and proliferative glomerulonephritis (i.e., class III and V or class IV and V) are also reported (Weening J J, et al. The classification of glomerulonephritis in systemic lupus erythematosus revisited. J Am Soc Nephrol 2004; 15:241-50).

IgA nephropathy (a.k.a. IgA nephritis, Berger disease, or synpharyngitic glomerulonephritis) occurs when immunoglobulin A (IgA) antibody deposits lodge in the kidneys. In certain embodiments, IgA nephropathy is a kidney disease associated with inflammation of the glomeruli of the kidney and/or IgA deposits within the kidneys. In certain embodiments, IgA nephropathy includes related disorders such as, but not limited to, Henoch Schonlein Purpura (HSP).

IBD is an inflammatory condition of the colon and/or small intestine. Increases in the abundance of *Ruminococcus gnavus* in the intestine have been reported to occur in some subjects, and clinical subsets of Inflammatory Bowel Disease, which include ulcerative colitis and Crohns disease (Willing B P, et al. Gastroenterology 2010; 139:1844; Png C W, et al. Am J Gastroenterol 2010; 105:2420-8; Joossens M, Huys G, Cnockaert M, et al. Dysbiosis of the faecal microbiota in patients with Crohn's disease and their unaffected relatives. Gut 2011; 60:631-7). In particular, Ileal Crohns Disease has been associated with increases in *R. gnavus*, although the contributory mechanisms of *R. gnavus* were not explored. In certain embodiments, the IBD is an inflammatory condition of the colon, small intestine, large intestine, mouth, esophagus, stomach, anus, or rectum. In certain embodiments, the IBD is Crohn's disease, ulcerative colitis, microscopic colitis (e.g., collagenous colitis, lymphocytic colitis), diversion colitis, Behcet's disease, or indeterminate colitis. In certain embodiments, the IBD is Crohn's disease or ulcerative colitis.

Detection of Antibodies

In certain embodiments, the present invention provides methods for diagnosis or methods of monitoring that can involve determining the level of antibodies that recognize a bacterial antigen. In certain embodiments, the detection of antibodies can be used in combination with the methods disclosed throughout the specification such as, but not limited to, detecting the level of gastrointestinal bacteria.

In certain embodiments, the present invention provides for methods of detecting antibodies that recognize a bacterial antigen. In certain embodiments, the antibodies are IgA, IgD, IgE, IgG, or IgM. In certain embodiments, the antibodies are IgG. In certain embodiments, the antibodies are detected in a bodily fluid sample. Bodily fluids include, but are not limited to blood, saliva, urine, gastric and digestive fluid, tears, stool, semen, vaginal fluid, interstitial fluids derived from tumorous tissue, and cerebrospinal fluid. In certain embodiments, the bodily fluid is a blood sample. In certain embodiments, the blood sample is plasma or serum. The blood sample is to be handled in a manner consistent with immune assays for testing the presence of antibodies. In certain embodiments, the bodily fluid is saliva.

In certain embodiments, the present invention provides a method for determining whether a subject diagnosed with SLE or ILE is at an increased risk for developing lupus nephritis, progression of SLE, and/or complications of lupus comprising a) determining in a bodily fluid sample collected from the subject a level of antibodies that recognize a bacterial antigen, b) comparing the level of antibodies determined in step a) to a control level of antibodies, and c) determining that the subject is at an increased risk for developing lupus nephritis, progression of SLE, and/or complications of lupus if the level of antibodies determined in step a) is statistically significantly higher than the control level.

In certain embodiments, the present invention provides a method for determining whether a subject has SLE and/or lupus nephritis comprising a) determining in a bodily fluid sample collected from the subject a level of antibodies that recognize a bacterial antigen, b) comparing the level of antibodies determined in step a) to a control level of antibodies, and c) determining that the subject has SLE and/or lupus nephritis if the level of antibodies determined in step a) is statistically significantly higher than the control level.

In another embodiment, the present invention provides a method for determining whether a subject has an IgA nephropathy or related renal condition or is at an increased risk for developing an IgA nephropathy or a related renal condition comprising a) determining in a bodily fluid sample collected from the subject a level of antibodies that recognize a bacterial antigen, b) comparing the level of antibodies determined in step a) to a control level of antibodies, and c) determining that the subject has an IgA nephropathy or related renal condition or is at an increased risk for developing an IgA nephropathy or related renal condition if the level of antibodies determined in step a) is statistically significantly higher than the control level. In certain embodiments, the related renal condition can be, but it not limited to, Henoch Schonlein Purpura.

In another embodiment, the present invention provides a method for determining whether a subject has glomerulonephritis or is at an increased risk for developing glomerulonephritis comprising a) determining in a bodily fluid sample collected from the subject a level of antibodies that recognize a bacterial antigen, b) comparing the level of antibodies determined in step a) to a control level of antibodies, and c) determining that the subject has glomerulonephritis or is at an increased risk for developing glomerulonephritis if the level of antibodies determined in step a) is statistically significantly higher than the control level.

In another embodiment, the present invention provides a method for determining whether a subject has IBD or is at an increased risk for developing IBD comprising a) determining in a bodily fluid sample collected from the subject a level of antibodies that recognize a bacterial antigen, b) comparing the level of antibodies determined in step a) to a control level of antibodies, and c) determining that the subject has IBD or is at an increased risk for developing IBD if the level of antibodies determined in step a) is statistically significantly higher than the control level.

In another embodiment, the present invention provides a method for monitoring changes in development of a disorder (as described above) in a subject, which method comprises a) determining in two or more bodily fluid samples (i.e., of the same type) collected from the subject at spaced apart time points (as described above) a level of antibodies that recognize a bacterial antigen, b) comparing the level of antibodies determined in step a) between the earlier collected and later collected sample(s), and c) (i) determining that the disorder in the subject has progressed if the level of antibodies determined in step a) is increased in the later collected sample(s) as compared to the earlier collected sample(s), or (ii) determining that the disorder in the subject has not progressed if the level of antibodies determined in step a) is not increased in the later collected bodily fluid sample(s) as compared to the earlier collected sample(s). In certain embodiments, an increase of at least about 1.2-fold, at least about 1.5-fold, at least about 2.0-fold, at least about 2.5-fold, at least about 3-fold, at least about 3.5-fold, at least about 4-fold, at least about 4.5-fold, or at least about 5-fold in the level of the antibodies in the later collected sample(s) as compared to the earlier collected samples indicates a progression of the disorder.

In certain embodiments, the bodily fluid samples are collected at least once a year, at least twice a year, at least three times a year, at least four times a year, at least five times a year, at least six times a year, at least seven times a year, at least eight times a year, at least nine times a year, at least ten times a year, at least eleven times a year, or at least twelve times a year. In certain embodiments, the blood samples are collected once every month, once every two months, once every three months, once every four months, or once every six months. In certain embodiments, the bodily fluid is a blood sample.

In another embodiment, the present invention provides a method for monitoring the effect of a treatment on development of a disorder (as described above) in a subject, which method comprises: a) determining a level of a bacterial antigen in a bodily fluid sample collected from the subject prior to initiation of the treatment, b) determining a level of antibodies against the bacterial antigen in a bodily fluid sample collected from the subject in the course of or following the treatment, c) comparing the level of antibodies determined in steps a) and b), and d) (i) determining that the treatment is effective for said disorder if the level of antibodies determined in step b) is not higher than the level of antibodies determined in step a), or (ii) determining that the treatment is not effective for said disorder if the level of antibodies determined in step b) is higher than the level of antibodies determined in step a). In certain embodiments, a level of antibodies in step b) of at least about 1.2-fold, at least about 2-fold, at least about 3-fold, at least about 4-fold, or at least about 5-fold lower than the level of step a) indicates that treatment is effective. In certain embodiments, a level of antibodies in step b) between about 1.2-fold to about 5-fold or about 2-fold to about 4-fold lower than in step a) indicates that treatment is effective. In certain embodiments, the level of antibodies in step b) is at least about 2-fold lower than the level of step a).

An antigen is a molecule capable of inducing an immune response in a host. For example, an antigen can be any protein, carbohydrate, lipid, nucleic acid, or mixture of these, or a plurality of these, to which an immune response is elicited.

In certain embodiments, the bacterial antigen is derived from *Ruminococcus gnavus* strain CC55_001C, HM-1056 (Human Microbiome Project (HMP) ID 1201; GenBank: AZJF00000000). Taxonomically, *R. gnavus* originally belonged to the genus Ruminococcus in the family Ruminococcaceae. The Ruminococcus genus contained 18 species, but on the basis of 16S ribosomal gene sequencing, some of the species have been reassigned to the new genus *Blautia* within the family Lachnospiraceae, which, like Ruminococcaceae, is a part of the order Clostridiales. *R. gnavus* was reassigned due to its active fermentative ability, but *R. gnavus* has retained the *Ruminococcus* genus name (82).

In certain embodiments, the bacterial antigen is derived from a bacterial strain from the Lachnospiraceae family, wherein the strain has 16S rDNA or rRNA with at least 95%, 96%, 97%, 98%, 99% or including 100% sequence identity to the 16S rDNA or rRNA of *Ruminococcus gnavus* strain CC55_001C, as described above, over its entire length or at least 95%, 96%, 97%, 98%, 99% or including 100% sequence identity to any single V region of the 16S rDNA or rRNA. In certain embodiments, the bacterial antigen is derived from a bacterial strain from the Lachnospiraceae family, wherein the strain has 16S rDNA or rRNA with at least 95%, sequence identity to the 16S rDNA or rRNA of *Ruminococcus gnavus* strain CC55_001C over its entire length. In certain embodiments, the bacterial antigen is derived from a bacterial strain from the Lachnospiraceae family, wherein the strain has at least 97% sequence identity to any single V region of the 16S rDNA or rRNA of *Ruminococcus gnavus* strain CC55_001C. In certain embodiments, the V region of 16S rDNA or rRNA is the V4 region. In certain embodiments, the bacterial antigen is derived from a bacterial strain from the Lachnospiraceae family, wherein the strain has at least 99% sequence identity to any single V region of the 16S rDNA or rRNA of *Ruminococcus gnavus* strain CC55_001C. In certain embodiments, the V region of 16S rDNA or rRNA is the V4 region.

In certain embodiments, the bacterial antigen is derived from a bacterial strain from the *Blautia* genus, wherein the strain has 16S rDNA or rRNA with at least 95%, 96%, 97%, 98%, 99% or including 100% sequence identity to the 16S rDNA or rRNA of *Ruminococcus gnavus* strain CC55_001C, as described above, over its entire length or at least 95%, 96%, 97%, 98%, 99% or including 100% sequence identity to any single V region of the 16S rDNA or rRNA. In certain embodiments, the bacterial antigen is derived from a bacterial strain from the *Blautia* genus, wherein the strain has 16S rDNA or rRNA with at least 95%, sequence identity to the 16S rDNA or rRNA of *Ruminococcus gnavus* strain CC55_001C over its entire length. In certain embodiments, the bacterial antigen is derived from a bacterial strain from the *Blautia* genus, wherein the strain has at least 97% sequence identity to any single V region of the 16S rDNA or rRNA of *Ruminococcus gnavus* strain CC55_001C. In certain embodiments, the V region of 16S rDNA or rRNA is the V4 region. In certain embodiments, the bacterial antigen is derived from a bacterial strain from the *Blautia* genus, wherein the strain has at least 99% sequence identity to any single V region of the 16S rDNA or rRNA of *Ruminococcus gnavus* strain CC55_001C. In certain embodiments, the V region of 16S rDNA or rRNA is the V4 region.

In certain embodiments, the bacterial antigen is derived from a bacterial strain from the *Ruminococcus gnavus* species, wherein the strain has 16S rDNA or rRNA with at least 95%, 96%, 97%, 98%, 99% or including 100% sequence identity to the 16S rDNA or rRNA of *Ruminococcus gnavus* strain CC55_001C, as described above, over its entire length or at least 95%, 96%, 97%, 98%, 99% or including 100% sequence identity to any single V region of the 16S rDNA or rRNA. In certain embodiments, bacterial antigen is derived from a bacterial strain from the *Ruminococcus gnavus* species, wherein the strain has 16S rDNA or rRNA with at least 95%, sequence identity to the 16S rDNA or rRNA of *Ruminococcus gnavus* strain CC55_001C over its entire length. In certain embodiments, the bacterial antigen is derived from a bacterial strain from the *Ruminococcus gnavus* species, wherein the strain has at least 97% sequence identity to any single V region of the 16S rDNA or rRNA of *Ruminococcus gnavus* strain CC55_001C. In certain embodiments, the V region of 16S rDNA or rRNA is the V4 region. In certain embodiments, the bacterial antigen is derived from a bacterial strain from the *Ruminococcus gnavus* species, wherein the strain has at least 99% sequence identity to any single V region of the 16S rDNA or rRNA of *Ruminococcus gnavus* strain CC55_001C. In certain embodiments, the V region of 16S rDNA or rRNA is the V4 region.

In certain embodiments, the bacterial antigen comprises a non-protein, non-nucleic acid molecule. In certain embodiments, the bacterial antigen comprises a bacterial lipoglycan or a derivative thereof.

In addition to using full-length lipoglycan, the methods of the invention can use lipoglycan derivatives, including lipoglycan fragments, for antibody detection. Production of such fragments is disclosed, e.g., in van der Es et al., Chem Soc Rev. 2017 46(5):1464-1482.

In certain embodiments, the lipoglycan-containing antigen or derivative thereof is derived from *Ruminococcus gnavus* strain CC55_001C, HM-1056 (Human Microbiome Project (HMP) ID 1201; GenBank: AZJF00000000).

In certain embodiments, the lipoglycan-containing antigen or derivative thereof is derived from a bacterial strain from the Lachnospiraceae family, wherein the strain has 16S rDNA or rRNA with at least 95%, 96%, 97%, 98%, 99% or including 100% sequence identity to the 16S rDNA or rRNA of *Ruminococcus gnavus* strain CC55_001C, as described above, over its entire length or at least 95%, 96%, 97%, 98%, 99% or including 100% sequence identity to any single V region of the 16S rDNA or rRNA. In certain embodiments, the lipoglycan-containing antigen or derivative thereof is derived from a bacterial strain from the Lachnospiraceae family, wherein the strain has 16S rDNA or rRNA with at least 95%, sequence identity to the 16S rDNA or rRNA of *Ruminococcus gnavus* strain CC55_001C over its entire length. In certain embodiments, the lipoglycan or derivative thereof is derived from a bacterial strain from the Lachnospiraceae family, wherein the strain has at least 97% sequence identity to any single V region of the 16S rDNA or rRNA of *Ruminococcus gnavus* strain CC55_001C. In certain embodiments, the V region of 16S rDNA or rRNA is the V4 region. In certain embodiments, the lipoglycan-containing antigen or derivative thereof is derived from a bacterial strain from the Lachnospiraceae family, wherein the strain has at least 99% sequence identity to any single V region of the 16S rDNA or rRNA of *Ruminococcus gnavus* strain CC55_001C. In certain embodiments, the V region of 16S rDNA or rRNA is the V4 region.

In certain embodiments, the lipoglycan-containing antigen or derivative thereof is derived from a bacterial strain from the *Blautia* genus, wherein the strain has 16S rDNA or rRNA with at least 95%, 96%, 97%, 98%, 99% or including 100% sequence identity to the 16S rDNA or rRNA of *Ruminococcus gnavus* strain CC55_001C, as described above, over its entire length or at least 95%, 96%, 97%, 98%, 99% or including 100% sequence identity to any single V region of the 16S rDNA or rRNA. In certain embodiments, the lipoglycan-containing antigen or derivative thereof is derived from a bacterial strain from the *Blautia* genus, wherein the strain has 16S rDNA or rRNA with at least 95%, sequence identity to the 16S rDNA or rRNA of *Ruminococcus gnavus* strain CC55_001C over its entire length. In certain embodiments, the lipoglycan-containing antigen or derivative thereof is derived from a bacterial strain from the *Blautia* genus, wherein the strain has at least 97% sequence identity to any single V region of the 16S rDNA or rRNA of *Ruminococcus gnavus* strain CC55_001C. In certain embodiments, the V region of 16S rDNA or rRNA is the V4 region. In certain embodiments, the lipoglycan-containing antigen or derivative thereof is derived from a bacterial strain from the *Blautia* genus, wherein the strain has at least 99% sequence identity to any single V region of the 16S rDNA or rRNA of *Ruminococcus gnavus* strain CC55_001C. In certain embodiments, the V region of 16S rDNA or rRNA is the V4 region.

In certain embodiments, the lipoglycan-containing antigen or derivative thereof is derived from a bacterial strain from the *Ruminococcus gnavus* species, wherein the strain has 16S rDNA or rRNA with at least 95%, 96%, 97%, 98%, 99% or including 100% sequence identity to the 16S rDNA or rRNA of *Ruminococcus gnavus* strain CC55_001C, as described above, over its entire length or at least 95%, 96%, 97%, 98%, 99% or including 100% sequence identity to any single V region of the 16S rDNA or rRNA. In certain embodiments, the lipoglycan-containing antigen or derivative thereof is derived from a bacterial strain from the *Ruminococcus gnavus* species, wherein the strain has 16S rDNA or rRNA with at least 95%, sequence identity to the 16S rDNA or rRNA of *Ruminococcus gnavus* strain CC55_001C over its entire length. In certain embodiments, the lipoglycan-containing antigen or derivative thereof is derived from a bacterial strain from the *Ruminococcus gnavus* species, wherein the strain has at least 97% sequence identity to any single V region of the 16S rDNA or rRNA of *Ruminococcus gnavus* strain CC55_001C. In certain embodiments, the V region of 16S rDNA or rRNA is the V4 region. In certain embodiments, the lipoglycan-containing antigen or derivative thereof is derived from a bacterial strain from the *Ruminococcus gnavus* species, wherein the strain has at least 99% sequence identity to any single V region of the 16S rDNA or rRNA of *Ruminococcus gnavus* strain CC55_001C. In certain embodiments, the V region of 16S rDNA or rRNA is the V4 region.

In certain embodiments, the bacteria has antigenic gene products other than lipoglycan-containing antigen that leads to SLE and lupus nephritis as well as inflammatory diseases such as, but not limited to, glomerulonephritis (e.g., IgA nephropathy) and IBD (e.g., ulcerative colitis and Crohn's Disease).

In certain embodiments, bacterial antigen is obtained by treating a culture of bacteria with a lysozyme, a nucleic acid digesting agent (e.g., nucleases), and/or a protease. In certain embodiments, the culture is treated with a protease after treatment with a lysozyme and/or a nucleic acid digesting agent. In certain embodiments, the culture is treated with a protease before treatment with a lysozyme and/or a nucleic acid digesting agent.

In certain embodiments, the bacteria are cultured by ordinary methods known to one of skill in the art. In certain embodiments, the bacteria are cultured in a rich nutrient media. In certain embodiments, the bacteria are cultured in chopped Meat Broth.

Lysozymes are enzymes that occur naturally in egg white, human tears, saliva, and other body fluids, capable of destroying the cell walls of certain bacteria and thereby acting as a mild antiseptic. Exemplary lysozymes include, but are not limited to, animal based lysozymes (e.g., human, turkey, chicken, dog, rat), egg white lysozymes (e.g., chickens, ducks, quails, turkeys, and geese), and plant lysozymes.

Nucleic acid fragmentation can be achieved by any method of polynucleotide fragmentation known to those of skill in the art including, but not limited to, nuclease digestion (e.g., restriction enzymes, non-sequence-specific nucleases such as DNase I, micrococcal nuclease, SI nuclease and mung bean nuclease), and physical methods such as shearing and sonication. Isolation is accomplished by any technique that allows for the selective purification of marked fragments from unmarked fragments (e.g., size or affinity separation techniques and/or purification on the basis of a physical property).

Random cleavage can be achieved by enzymatic methods including: a single or a combination of nucleases such as *Serratia marcescens*, Fragmentase® (New England Biolabs, Ipswich, Mass.), DNAse I, and Benzonase® (EMD, Gibbstown, N.J.), or other types of nucleases. Fragmentase is an endonuclease that generates dsDNA breaks in a time-dependent manner to yield 100 bp-800 bp DNA fragments. Benzonase is genetically engineered endonuclease from *Serratia marcescens* that can effectively cleave both DNAs and RNAs. Other enzymatic methods include the use of Vvn nuclease alone or *Serratia* nuclease, or DNase I, or other nuclease in the art such as Shearase™ (Zymo Research, Irvine, Calif.) or Ion Shear™ (Life Technologies, Grand Island, N.Y.). Nicking enzymes can be used since the DNA is denatured after fragmentation.

Exemplary proteases include, but are not limited to, proteinase K, gelatinase A, gelatinase B, trypsin, trypsin (Arg blocked), trypsin (Lys blocked), clostripain, endoproteinase (e.g., microvillar, Asp-N), chymotrypsin, cyanogen bromide, iodozobenzoate, Myxobacter P., *Armillaria*, pepsin (e.g., luminal), dipeptidyl peptidase, enteropeptidase, hydrolase, bromelain, ficin, papain, pepsin, plasmin, thermolysin, thrombi, and cathepsins.

In certain embodiments, the bacterial antigen is obtained by a) pelleting a bacterial culture; b) producing a bacterial extract by treating the bacteria with a protein extraction buffer in the presence of a lysozyme, a nuclease, and/or a protease, and a detergent under non-denaturing conditions; c) incubating the mixture; d) removing cell debris (e.g., centrifugation), and using the supernatant as the antigen preparation. In certain embodiments, the bacterial extract is incubated in the presence of a lysozyme, a nuclease, and a protease. In certain embodiments, the nuclease is *Serratia marcescens*. In certain embodiments, the protease is Proteinase K.

In certain embodiments, the sample may be purified using size exclusion chromatography. In certain embodiments, the sample is enriched for specific characteristic polymers and oligomers and to remove irrelevant components.

In certain embodiments, the bacteria are incubated at 37° C. under anaerobic (75% $N_2$, 20% $CO_2$, and 5% $H_2$) conditions for at least 2, at least 3, at least 4, at least 5, at least 6, or at least 7 days. In certain embodiments, the cells are incubated for about 2 to about 7 days.

In certain embodiments, the level of antibodies is determined using an assay such as, but not limited to, bead-based assay, an enzyme-linked immunosorbent assay (ELISA), a radioimmunoassay, Western blotting, and/or any variant of an assay that detects these same antigen-reactive antibodies. In certain embodiments, the bacterial antigen, TA, or derivative thereof, is coated onto a bead or onto the surface of an ELISA plate or other solid phase used for detection.

In certain embodiments, the control level of antibodies can be obtained from, for example, a predetermined standard; the level in a similarly prepared sample obtained from the same subject in the past; or the level in a similarly prepared sample obtained from a matched healthy subject or an average of several matched healthy subjects.

In certain embodiments, the average/mean is obtained by testing at least two, at least three, at least four, at least five, at least 10, at least 20, at least 25, at least 50, at least 75, or at least 100 healthy subjects. In certain embodiments, the average is the mean plus one, two, or three standard deviations of a group of unaffected matched subjects. In certain embodiments, the level of the antibodies is determined to be statistically significantly higher than the control level if the level is higher than the mean value of normal plus one standard deviation. In certain embodiments, the level of the antibodies is determined to be statistically significantly higher than the control level if the level is higher than the mean value of normal plus two standard deviations. In certain embodiments, the level of the antibodies is determined to be statistically significantly higher than the control level if the level is higher than the mean value of normal plus three standard deviations. In certain embodiments, the level of the antibodies is determined to be statistically significantly higher than the control level if the level is higher than the mean value calculated for at least 40 unaffected healthy subjects plus three standard deviations. In one embodiment a level is measured in the serum of an individual and we reevaluate over time to determine if there are patterns of increases over time.

In certain embodiments, the predetermined standard is a value which represents a statistically validated threshold ratio of the levels of the antibodies equal to the highest possible value within the range of corresponding values in a large cohort of matched healthy subjects. In certain embodiments, the predetermined standard is a value which represents a statistically validated threshold cut-off of the levels of the antibodies equal to the highest possible value within the range of corresponding values in a large cohort of matched healthy subjects.

Detection of Gastrointestinal (GI) Microbiota

In certain embodiments, the present invention provides methods for diagnosis or methods of monitoring that can involve determining the abundance of gastrointestinal (GI) bacteria. In certain embodiments, the detection of GI bacteria can be used in combination with the methods disclosed throughout the specification such as, but not limited to, detecting the level of antibodies against a bacterial antigen.

In certain embodiments, the microbiota sample can be taken from the stomach, duodenum, jejunum, ileum, cecum, colon and feces. In certain embodiments, the microbiota sample can be taken from the feces or intestines.

In certain embodiments, the method involves testing for the abundance of bacteria that produces a bacterial antigen associated with autoimmune disease such as, but not limited to, systemic lupus erythematosus (SLE) and lupus nephritis as well as inflammatory diseases such as, but not limited to, glomerulonephritis (e.g., IgA nephropathy) and inflammatory bowel disease (IBD) (e.g., ulcerative colitis and Crohn's disease). In certain embodiments, the method involves testing for the abundance of bacteria that produces a bacterial antigen as disclosed above.

In certain embodiments, the method involves testing for the abundance of *Ruminococcus gnavus* strain CC55_001C (as described above). In certain embodiments, the method involves testing for a strain from the Lachnospiraceae family, wherein said strain has 16S rDNA or rRNA with at least 95%, 96%, 97%, 98%, 99% or including 100% sequence identity to the 16S rDNA or rRNA of *Ruminococcus gnavus* strain CC55_001C over its entire length or at least 95%, 96%, 97%, 98%, 99% or including 100% sequence identity to any single V region of the 16S rDNA or rRNA of *Ruminococcus gnavus* strain CC55_001C. In certain embodiments, the bacteria shares antigenic determinants with *Ruminococcus gnavus* strain CC55_001C. In certain embodiments, the bacterial strain is from the Lachnospiraceae family, wherein the strain has 16S rDNA or rRNA with at least 95%, sequence identity to the 16S rDNA or rRNA of *Ruminococcus gnavus* strain CC55_001C over its entire length. In certain embodiments, the bacterial strain is from the Lachnospiraceae family, wherein the strain has at least 97% sequence identity to any single V region of the 16S rDNA or rRNA of *Ruminococcus gnavus* strain CC55_001C. In certain embodiments, the V region of 16S rDNA or rRNA is the V4 region. In certain embodiments, the bacterial strain is from the Lachnospiraceae family, wherein the strain has at least 99% sequence identity to any single V region of the 16S rDNA or rRNA of *Ruminococcus gnavus* strain CC55_001C. In certain embodiments, the V region of 16S rDNA or rRNA is the V4 region.

In another embodiment, the present invention provides a method for determining whether a subject diagnosed with SLE or ILE is at an increased risk for developing lupus nephritis, progression of SLE, and/or complications of lupus comprising a) determining in a GI microbiota sample collected from the subject the abundance of bacteria, b) comparing the abundance of bacteria determined in step a) to a control abundance of bacteria and c) determining that the subject is at an increased risk for developing lupus nephritis, progression of SLE, and/or complications of lupus if the abundance of bacteria determined in step a) is statistically significantly higher than the control abundance.

In another embodiment, the present invention provides a method for determining whether a subject has SLE and/or lupus nephritis comprising a) determining in a GI microbiota sample collected from the subject an abundance of bacteria, b) comparing the abundance of bacteria determined in step a) to a control abundance of the bacteria and c) that the subject has SLE and/or lupus nephritis if the abundance of the bacteria determined in step a) is statistically significantly higher than the control abundance.

In another embodiment, the present invention provides a method for determining whether a subject has IgA nephropathy or related renal disorder or is at an increased risk for developing an IgA nephropathy or related renal disorder comprising a) determining in a GI microbiota sample collected from the subject an abundance of bacteria, b) comparing the abundance of bacteria determined in step a) to a control abundance of the bacteria and c) that the subject has IgA nephropathy or related renal disorder or is at an increased risk for developing an IgA nephropathy or related renal disorder if the abundance of the bacteria determined in step a) is statistically significantly higher than the control abundance.

In another embodiment, the present invention provides a method for determining whether a subject has glomerulonephritis or related renal disorder or is at an increased risk for developing glomerulonephritis or related renal disorder comprising a) determining in a GI microbiota sample collected from the subject an abundance of bacteria, b) comparing the abundance of bacteria determined in step a) to a control abundance of the bacteria and c) that the subject has glomerulonephritis or related renal disorder or is at an increased risk for developing glomerulonephritis or related renal disorder if the abundance of the bacteria determined in step a) is statistically significantly higher than the control abundance.

In another embodiment, the present invention provides a method for determining whether a subject has IBD or is at an increased risk for developing IBD comprising a) determining in a GI microbiota sample collected from the subject an abundance of bacteria, b) comparing the abundance of bacteria determined in step a) to a control abundance of the bacteria and c) that the subject IBD or is at an increased risk for developing IBD if the abundance of the bacteria determined in step a) is statistically significantly higher than the control abundance.

In another embodiment, the present invention provides a method for monitoring changes in development of a disorder (as defined above) in a subject comprising a) determining in two or more GI microbiota samples collected from the subject at spaced apart time points an abundance of bacteria, b) comparing the abundance of bacteria determined in step a) between the earlier collected and later collected sample(s), and c) (i) determining that the disorder in the subject has progressed if the abundance of bacteria determined in step a) is increased in the later collected sample(s) as compared to the earlier collected sample(s), or (ii) determining that the disorder in the subject has not progressed if the abundance of bacteria determined in step a) is not increased in the later collected bodily fluid sample(s) as compared to the earlier collected sample(s). In certain embodiments, an increase of at least about 1.2-fold, at least about 1.5-fold, at least about 2.0-fold, at least about 2.5-fold, at least about 3-fold, at least about 3.5-fold, at least about 4-fold, at least about 4.5-fold, or at least about 5-fold in the abundance in the later collected sample(s) as compared to the earlier collected samples indicates a progression of the disorder.

In another embodiment, the present invention provides a method for monitoring the effect of a treatment on development of a disorder (as defined above) in a subject comprising a) determining in two or more GI microbiota samples collected from the subject at spaced apart time points an abundance of bacteria, b) determining in the GI microbiota sample collected from the subject in the course of or following the treatment an abundance of bacteria, c) comparing the abundance of bacteria determined in steps a) and b); and (i) determining that the treatment is effective for said disorder if the abundance of bacteria determined in step b) is not higher than the abundance of bacteria determined in step a), or (ii) determining that the treatment is not effective for said disorder if the abundance of bacteria determined in step b) is higher than the abundance of bacteria determined in step a).

In certain embodiments, an abundance of bacteria in step b) of at least about 1-fold, at least about 2-fold, at least about 3-fold, at least about 4-fold, or at least about 5-fold lower than the abundance of step a) indicates that treatment is effective. In certain embodiments, an abundance of bacteria in step b) of between about 1.2-fold to about 5-fold or about 2-fold to about 4-fold lower than in step a) indicates that treatment is effective. In certain embodiments, the abundance of bacteria in step b) is at least about 2-fold lower than the abundance of step a).

In certain embodiments, the control abundance of bacteria can be obtained from, for example, a predetermined standard; the abundance in a similarly prepared sample obtained from the same subject in the past; or the abundance in a similarly prepared sample obtained from a matched healthy subject or an average of several matched healthy subjects.

In certain embodiments, the average/mean is obtained by testing at least two, at least three, at least four, at least five, at least 10, at least 20, at least 25, at least 50, at least 75, or at least 100 healthy subjects. In certain embodiments, the average is the mean plus one, two, or three standard deviations of a group of unaffected matched subjects. In certain embodiments, the abundance of bacteria is determined to be statistically significantly higher than the control abundance if the abundance is higher than the mean value of normal plus one standard deviation. In certain embodiments, the abundance of bacteria is determined to be statistically significantly higher than the control abundance if the abundance is higher than the mean value of normal plus two standard deviations. In certain embodiments, the abundance of the bacteria is determined to be statistically significantly higher than the control abundance if the abundance is higher than the mean value of normal plus three standard deviations. In certain embodiments, the abundance of the bacteria is determined to be statistically significantly higher than the control abundance if the abundance is higher than the mean value calculated for at least 40 unaffected healthy subjects plus three standard deviations.

In certain embodiments, the predetermined standard is a value which represents a statistically validated threshold ratio of the abundances of the bacteria equal to the highest possible value within the range of corresponding values in a large cohort of matched healthy subjects.

Values will vary based on the methods for quantitation and should be normalized for the assay.

Non-limiting examples of the methods which can be used for determining the relative abundance of the bacterial strains include, e.g., quantitative polymerase chain reaction (qPCR), sequencing of bacterial 16S rDNA or rRNA, shotgun metagenome sequencing, bacterial genotype pattern based fingerprinting (DNA fingerprinting) and metabolomics. In certain embodiments, the bacterial strain is identified by high-throughput sequencing of one or more genes selected from the group consisting of 16S rDNA or rRNA, LtaS, TagB, TagF, TagE, TagG, TagH, TagH, RumA, and RumC to identify the abundance of the strain-specific nucleic acid sequence(s) (Formstone A, Carballido-Lopez J. Bacteriology 2008 190(5):1812-21).

Additional methods include methods of evaluating the microbiota population in a subject or diagnosing an abnormal microbiota development. Methods include monitoring the subject's microbiota after the administration of the microbiota inoculum or probiotic by: a) determining a relative abundance of one or more bacterial taxa in a microbiota sample obtained from the subject, and b) comparing the relative abundance(s) determined in step a) to (i) a predetermined standard value or (ii) to the abundance(s) of the same taxa in a control subject or (iii) to the average value of abundances of the same taxa in several control subjects.

The determination of relative abundance of the taxa may involve, for example, a method selected from the group consisting of quantitative polymerase chain reaction (qPCR), sequencing of bacterial 16S rDNA or rRNA, shotgun metagenome sequencing, bacterial genotype pattern based fingerprinting (DNA fingerprinting), and metabolomic analysis.

In accordance with the present invention there may be numerous tools and techniques within the skill of the art, such as those commonly used in molecular biology, pharmacology, and microbiology. Such tools and techniques are described in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

Additional Diagnostic Criteria

In certain embodiments, additional diagnostic steps may be combined with the methods above (i.e., detection of antibodies against a bacterial antigen and/or detection of certain GI bacteria). In certain embodiments, the additional diagnostic tests are performed before the methods described above. In certain embodiments, the additional diagnostic tests are performed after the methods described above. In certain embodiments, the additional diagnostic tests are performed in conjunction/simultaneously with the methods described above. In certain embodiments, each of the diagnostic tests is being performed simultaneously with other diagnostic methods for SLE and/or ILE. In certain embodiments, the diagnostic methods being performed simultaneously are being performed on the same panel. For assays using bodily fluid samples, the same or different sample may be used for two or more different assays.

In certain embodiments, the tests above are performed after the appearance of clinical features indicative of the disorder.

In certain embodiments, the diagnostic or monitoring methods can further comprise a separate diagnosis of SLE or incomplete lupus (ILE) syndrome. In certain embodiments, the diagnostic or monitoring methods can further comprise determining in a bodily fluid sample collected from the subject the level of antibodies against one or more additional antigens. In certain embodiments, the additional antigens can be double-stranded DNA (dsDNA), C1q, glomerular extract, nucleosomes, Smith Antibody (Sm), U1RNP, Ro/SSA, La/SSB, histone(s), and any combination thereof.

Autoantibodies can be detected in the serum prior to the onset of clinical disease, with the number and complexity of these antibodies increasing up to the point of diagnosis (Egner W. J Clin Pathol. 2000; 53:424-32; Arbuckle M R, et al. N Engl J Med. 2003; 349:1526-33.) This result raises the possibility that risk profiles for lupus could be detected prior to onset of clinical symptoms. Autoantibody complexity is increased in patients with incomplete lupus (ILE) syndromes defined as having at least one but less than four of the criteria needed for a diagnosis of SLE (Wandstrat A E, et al. J Autoimmun. 27:153-60]. Detection of IgG antibodies to lipoglycan-containing antigen of *R. gnavus* may aid this diagnosis, establish prognosis, and also enable early and effective treatment.

In certain embodiments, the level of the antibodies against said one or more additional antigen(s) is determined in the same sample as the level of the antibodies against lipoglycan-containing antigen or a derivative thereof or antibodies to the bacterial antigen. In certain embodiments, the level of antibodies can be determined using a method selected from the group consisting of enzyme-linked immunosorbent assay (ELISA), *Crithidia luciliae* immunofluorescence test, radioimmunoassay, counterimmunoelectrophoreses (CIE), immunodiffusion, Western blotting, bead based assays, and/or hemagglutination.

In certain embodiments, the diagnostic or monitoring methods can further comprise determining in a bodily fluid sample collected from the subject the level of analytes including C1q, C3, C4, CH50, C-reactive protein (CRP), and any combination thereof.

In certain embodiments the increased level of the antibodies against said one or more additional antigen(s) or analytes as compared to a relevant control is indicative of SLE, lupus nephritis as well as inflammatory diseases such as, but not limited to, glomerulonephritis (e.g., IgA nephropathy) and inflammatory bowel disease (IBD) (e.g., ulcerative colitis and Crohn's disease).

In certain embodiments, the diagnostic or monitoring methods can further comprise testing the erythrocyte sedimentation rate (ESR). ESR is the rate at which red blood cells sediment in a period of one hour. ESR is increased in inflammation, pregnancy, anemia, autoimmune disorders (such as rheumatoid arthritis and lupus), infections, and some kidney diseases. In certain embodiments, the test is performed by placing anticoagulated blood in an upright tube (e.g., a Westergren tube), and the rate at which the red blood cells fall was measured and reported in mm/h.

In certain embodiments, the diagnostic or monitoring methods further comprise determining SLE Disease Activity Index (SLEDAI), SLEDAI modified by the Safety of Estrogens in Lupus Erythematosus National Assessment trial (SELENA-SLEDAI), British Isles Lupus Activity Group (BILAG) assessment or the SLAM index. Currently the diagnosis of SLE is based on either ACR criteria (1) or SLICC criteria (2). 1. Hochberg M C. Arthritis Rheum. 1997; 40(9):1725. 2. Petri M, et al. Arthritis Rheum. 2012; 64(8):2677-2686.

In certain embodiments, the diagnostic or monitoring methods further comprise conducting a kidney assessment. In certain embodiments, the kidney assessment entails a kidney biopsy.

In certain embodiments, the diagnostic or monitoring methods further comprise urinalysis. In certain embodiments, the urinalysis comprises determining the level of protein and/or red blood cells in the urine, and wherein the increased level of protein (e.g., proteinuria) or red blood cells as compared to a relevant control is indicative of a kidney disease. In certain embodiments, the protein in the urine can be albumin. In certain embodiments, the total level of protein in the urine is determined. In certain embodiment, the total protein in a 24 hour urine collection is determined and the ratio to creatinine in serum or urine is determined.

Anti-Bacterial and Other Therapeutic Methods of the Invention

In one aspect, the invention provides a method for treating (including preventing) SLE and lupus nephritis as well as inflammatory diseases such as, but not limited to, glomerulonephritis (e.g., IgA nephropathy) and inflammatory bowel disease (IBD) (e.g., ulcerative colitis and Crohn's disease) in a subject in need thereof, said method comprising administering to the subject a compound or composition, wherein the compound or composition inhibits growth and/or activity of one or more strains of bacteria in the GI microbiota of the subject. In certain embodiments, the growth is inhibited to the extent that the bacterial strains are removed from the microbiota (i.e., reduced or ablated).

In one embodiment of any of the methods of the invention, the compound or composition that inhibits growth and/or activity of one or more strains of bacteria is administered to the subject by a route selected from the group consisting of oral, rectal (e.g., by enema), mucosal, sublingual, and via naso/oro-gastric gavage. In one embodiment, the compound or composition that inhibits growth and/or activity of one or more strains of bacteria is administered directly to the GI of the subject.

In some embodiments, the compound or composition inhibits growth and/or activity of one or more strains of bacteria from *Ruminococcus gnavus*. In certain embodiments, the compound or composition inhibits growth and/or activity of at least 2, 3, 4, 5, 6, 7, 8, 9, 10, 20, 50 or more strains from *Ruminococcus gnavus*. In certain embodiments, the compound or composition inhibits growth and/or activity of the *Ruminococcus gnavus* strain CC55_001C.

In some embodiments of any of the above methods involving administration of a compound or composition that inhibits growth and/or activity of one or more strains of bacteria of *Ruminococcus gnavus* or a closely related OTUs which are independently characterized by, e.g., at least 95%, 96%, 97%, 98%, 99% or including 100% sequence identity to 16S rDNA or rRNA sequences of the bacteria from *Ruminococcus gnavus* strain CC55_001C. In another embodiment, the OTUs may be characterized by one or more of the variable regions of the 16S rDNA or rRNA sequence (V1-V9). These regions in bacteria are defined by nucleotides 69-99, 137-242, 433-497, 576-682, 822-879, 986-1043, 1117-1173, 1243-1294 and 1435-1465, respectively, using numbering based on the *E. coli* system of nomenclature. (See, e.g., Brosius et al., Complete nucleotide sequence of a 16S ribosomal RNA gene from *Escherichia coli*, PNAS 75(10):4801-4805 (1978)). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU.

In some embodiments, the composition is administered to the subject in an effective amount sufficient to inhibit the biosynthesis of lipoglycan-containing antigen or a derivative thereof or of a bacterial antigen as described above. In some embodiments, the composition is administered to the subject in an effective amount sufficient to increase the removal of lipoglycan-containing antigen or derivative thereof or of a bacterial antigen from the body or to block the immunologic and biologic effects of the lipoglycan-containing antigen, derivative thereof or of a bacterial antigen.

In certain embodiments, the method comprises administering to the subject an effective amount of a compound or composition, wherein the compound or composition inhibits growth and/or activity of one or more strains of bacteria from the phylum ofFirmicutes in the GI microbiota of the subject. In certain embodiments, the compound or composition inhibits growth and/or activity of at least 2, 3, 4, 5, 6, 7, 8, 9, 10, 20, 50 or more strains from this taxon.

In certain embodiments, the method comprises administering to the subject an effective amount of a compound or composition, wherein the compound or composition inhibits growth and/or activity of one or more strains of bacteria from the class of Clostridia in the GI microbiota of the subject. In certain embodiments, the compound or composition inhibits growth and/or activity of at least 2, 3, 4, 5, 6, 7, 8, 9, 10, 20, 50 or more strains from this taxon.

In certain embodiments, the method comprises administering to the subject an effective amount of a compound or composition, wherein the compound or composition inhibits growth and/or activity of one or more strains of bacteria from the order of Clostridiales in the GI microbiota of the subject. In certain embodiments, the compound or composition inhibits growth and/or activity of at least 2, 3, 4, 5, 6, 7, 8, 9, 10, 20, 50 or more strains from this taxon.

In certain embodiments, the method comprises administering to the subject an effective amount of a compound or composition, wherein the compound or composition inhibits growth and/or activity of one or more strains of bacteria from the family of Lachnospiraceae or Ruminococcaceae in the GI microbiota of the subject. In certain embodiments, the compound or composition inhibits growth and/or activity of at least 2, 3, 4, 5, 6, 7, 8, 9, 10, 20, 50 or more strains from these taxa.

In certain embodiments, the method comprises administering to the subject an effective amount of a compound or composition, wherein the compound or composition inhibits growth and/or activity of one or more strains of bacteria from the genus *Blautia* or *Ruminococcus* in the GI microbiota of the subject. In certain embodiments, the compound or composition inhibits growth and/or activity of at least 2, 3, 4, 5, 6, 7, 8, 9, 10, 20, 50 or more strains from these taxa.

In certain embodiments, the method comprises administering to the subject an effective amount of a compound or composition, wherein the compound or composition inhibits growth and/or activity of one or more strains of bacteria from the species *Ruminococcus gnavus* in the GI microbiota of the subject. In certain embodiments, the compound or composition inhibits growth and/or activity of at least 2, 3, 4, 5, 6, 7, 8, 9, 10, 20, 50 or more strains from this taxon. In certain embodiments, the compound or composition inhibits the immunologic activity of the strain associated with the bacterial antigen. In certain embodiments, the compound or composition inhibits the expression of the bacterial antigen. In certain embodiments, the compound or composition reduces the content of the bacterial antigen within the bacteria. In certain embodiments, the compound or composition reduces the content of the bacterial antigen within the GI tract. In certain embodiments, the compound or composition reduces the content of the bacterial antigen within the systemic circulation.

In one embodiment of any of the above methods of the invention, the compound or composition that inhibits growth and/or activity of one or more strains of bacteria is administered in a therapeutically effective amount. The dosages of the compound or composition administered in the methods of the invention will vary widely, depending upon the subject's physical parameters, the frequency of administration, the manner of administration, the clearance rate, and the like. The initial dose may be larger, and might be followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to reduce or eradicate colonization.

In some embodiments, the compound or composition that inhibits growth and/or activity of one or more strains of bacteria according to any of the above methods can be natural products that inhibit microbial growth. In certain embodiments, the compound or composition that inhibits growth and/or activity of one or more strains of bacteria according to any of the above methods can be bacteria that is conditionally lethal engineered bacteria (e.g., *H. Pylori, E. coli*, etc. . . . ). In certain embodiments, the compound or composition that inhibits growth and/or activity of one or more strains of bacteria according to any of the above methods can be genetically engineered commensals strains of microorganisms.

In some embodiments, suppressing growth or activity of at least one bacterial species in the microbiota according to any of the above methods involving such suppression can be achieved, e.g., by administering an antibiotic. In one specific embodiment, the antibiotic is administered in a therapeutic dose. In another specific embodiment, the antibiotic is administered in a sub-therapeutic dose. Non-limiting examples of antibiotics useful in the methods of the invention include beta-lactams (e.g., Penicillin VK, Penicillin G, Amoxicillin trihydrate), nitroimidazoles, macrolides (e.g., Tylosin tartrate, Erythromycin, Azithromycin, and Clarithromycin), tetracyclines, glycopeptides (e.g., Vancomycin), and fluoroquinolones. In one specific embodiment, the method comprises administering Penicillin VK or Penicillin G at 1 mg/kg body weight per day for at least four weeks of life. In another specific embodiment, the method comprises administering Amoxicillin trihydrate at 25 mg/kg body weight per day for 1 to 3 treatments each lasting 3 to 5 days. In yet another specific embodiment, the method comprises administering Tylosin tartrate at 50 mg/kg body weight per day for 1 to 3 treatments each lasting 3 to 5 days.

In certain embodiments, the method comprises administering to the subject an effective amount of a compound or composition, wherein the compound or composition results in a decrease in the level of the antibodies to a lipoglycan-containing antigen or a derivative thereof or to a bacterial antigen as described above. In certain embodiments, the compound of composition binds and neutralizes the lipoglycan-containing antigen or derivative thereof or the bacterial antigen or aids in the clearance of lipoglycan-containing antigen or derivative thereof or the bacterial antigen from the GI or circulation.

In certain embodiments, the compound is an antibody or a functional fragment thereof. In certain embodiments, the antibody or functional fragment binds to a lipoglycan-containing antigen or derivative thereof or to a bacterial antigen as described above. In certain embodiments, the antibody or functional fragment is a monoclonal antibody. In certain embodiments, the specific binding protein is a fully human monoclonal antibody or a binding fragment of a fully human monoclonal antibody. The binding fragments can include fragments such as Fab, Fab' or F(ab')2 and Fv. In certain embodiments, the compound is an antibody or a functional fragment thereof can be from the same or different species.

In certain embodiments, the antibody or fragment thereof is fully human and binds to the bacterial antigen with a Kd less than 500 picomolar (pM), less than 450 pM, less than 410 pM, less than 350 pM, less than 300 pM, less than 200 pM, less than 100 pM, less than 75 pM, less than 50 pM, less than 25 pM, less than 10 pM, less than 5 pM, or less than 2 pM. Affinity and/or avidity measurements can be measured by BIACORE®.

In certain embodiments, the antibody or functional fragment thereof is an IgA, IgD, IgE, IgG, or IgM. In certain embodiments, the antibody or functional fragment thereof is an IgA antibody. In certain embodiments, the antibody or functional fragment thereof is an IgA antibody produced by a dairy animal.

In certain embodiments, the method comprises mucosal immunization with the lipoglycan-containing antigen or derivative thereof or to the bacterial antigen as described above. In certain embodiments, the immune response is limited to the GI tract. In certain embodiments, the method prevents entry of the pathogenic substances into the circulation of the host.

In certain embodiments, the method comprises administering to the subject an effective amount of one or more compounds that bind or remove the lipoglycan-containing antigen or derivative thereof, or bacterial antigen as described above, and/or administering a compound such as, but not limited to, macrophage scavenger receptor protein (MSRP); a fragment of MSRP, wherein said fragment is capable of binding to said lipoglycan-containing antigen or lipoglycan derivative; gelsolin; a peptide comprising the amino acid sequence of the C-terminal helix of apolipoprotein CI (apoCI); daptomycin; activated charcoal; kaolinite; kaopectate; a cationic peptide; a phospholipid; a polysulphate; an endogenous binding protein or functional domain of a ficolin protein; or charcoal (e.g., activated charcoal), clay or binding resin. In certain embodiments, the compounds that bind or remove lipoglycan-containing antigen or derivatives thereof may be administered at least 1, 2, 3, 4, 5, 6, 7, or 9 times a day.

Probiotic/Prebiotic Therapeutic Methods of the Invention

In one aspect, the invention provides a method for treating (including preventing) SLE and lupus nephritis as well as inflammatory diseases such as, but not limited to, glomerulonephritis (e.g., IgA nephropathy) and IBD (e.g., ulcerative colitis and Crohn's disease) in a subject in need thereof, said method comprises administering a probiotic and/or a prebiotic composition, wherein the composition(s) stimulate growth and/or activity of one or more strains of bacteria.

In one embodiment of any of the above methods of the invention, the probiotic and/or prebiotic is administered to the subject by a route selected from the group consisting of oral, rectal (e.g., by enema), mucosal, sublingual, and via naso/oro-gastric gavage. In one embodiment, the probiotic is administered directly to the GI of the subject.

In some embodiments, the probiotic comprises one or more strains of bacteria from the species *Faecalibacterium prausnitzii*, species *Bacteroides uniformis*, genus *Akkermansia*, and/or genus *Lactobacillus*. In certain embodiments, the probiotic comprises at least 2, 3, 4, 5, 6, 7, 8, 9, 10, 20, 50 or more strains from the species *Faecalibacterium prausnitzii*, species *Bacteroides uniformis*, genus *Akkermansia*, and/or genus *Lactobacillus*. In some embodiments, only nonpathogenic species within the taxa qualify for use in the compositions or methods herein.

In some embodiments of any of the above methods involving administration of a probiotic composition, said probiotic composition comprises one or more OTUs which are independently characterized by, i.e., at least 95%, 96%, 97%, 98%, 99% or including 100% sequence identity to 16S rDNA or rRNA sequences of the bacteria from the species *Faecalibacterium prausnitzii*, species *Bacteroides uniformis*, genus *Akkermansia*, and/or genus *Lactobacillus*. In another embodiment, the OTUs may be characterized by one or more of the variable regions of the 16S rDNA or rRNA sequence (V1-V9). These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. (See, e.g., Brosius et al., Complete nucleotide sequence of a 16S ribosomal RNA gene from *Escherichia coli*, PNAS 75(10):4801-4805 (1978)). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU.

In some embodiments, the method comprises administering to the subject an effective amount of a probiotic or a prebiotic composition or a combination thereof, wherein said composition(s) stimulates growth and/or activity of one or more strains of bacteria from the species *Faecalibacterium prausnitzii*, species *Bacteroides uniformis*, genus *Akkermansia*, and/or genus *Lactobacillus* in the GI microbiota of the subject. In certain embodiments, the composition comprises at least 2, 3, 4, 5, 6, 7, 8, 9, 10, 20, 50 or more strains from the species *Faecalibacterium prausnitzii*, species *Bacteroides uniformis*, genus *Akkermansia*, and/or genus *Lactobacillus*.

In certain embodiments, the method comprises administering to the subject an effective amount of a probiotic or a prebiotic composition or a combination thereof, wherein said composition(s) stimulates growth and/or activity or includes of one or more strains of bacteria from one or more phyla selected from the group consisting of Firmicutes, Bacteroidetes, and/or Verrucomicrobia in the GI microbiota of the subject. In certain embodiments, the composition comprises at least 2, 3, 4, 5, 6, 7, 8, 9, 10, 20, 50 or more strains from these taxa.

In certain embodiments, the method comprises administering to the subject an effective amount of a probiotic or a prebiotic composition or a combination thereof, wherein said composition(s) stimulates growth and/or activity or includes of one or more strains of bacteria from one or more classes selected from the group consisting of Clostridia, Bacteroidetes, Verrucomicrobiae, and/or Bacilli in the GI microbiota of the subject. In certain embodiments, the composition comprises at least 2, 3, 4, 5, 6, 7, 8, 9, 10, 20, 50 or more strains from these taxa.

In certain embodiments, the method comprises administering to the subject an effective amount of a probiotic or a prebiotic composition or a combination thereof, wherein said composition(s) stimulates growth and/or activity or includes of one or more strains of bacteria from one or more orders selected from the group consisting of Clostridiales, Bacteroidales, Verrucomicrobiales and/or Lactobacillales in the GI microbiota of the subject. In certain embodiments, the composition comprises at least 2, 3, 4, 5, 6, 7, 8, 9, 10, 20, 50 or more strains from these taxa.

In certain embodiments, the method comprises administering to the subject an effective amount of a probiotic or a prebiotic composition or a combination thereof, wherein said composition(s) stimulates growth and/or activity or includes of one or more strains of bacteria from one or more families selected from the group consisting of Clostridiaceae, Bacteroidaceae, Verrucomicrobiaceae, and/or Lactobacillaceae in the GI microbiota of the subject. In certain embodiments, the composition comprises at least 2, 3, 4, 5, 6, 7, 8, 9, 10, 20, 50 or more strains from these taxa.

In certain embodiments, the method comprises administered to the subject an effective amount of a probiotic or a prebiotic composition or a combination thereof, wherein said composition(s) stimulates growth and/or activity or includes of one or more strains of bacteria from one or more genera selected from the group consisting of *Faecalibacterium, Bacteroides, Akkermansia*, and *Lactobacillus* in the GI microbiota of the subject. In certain embodiments, the composition comprises at least 2, 3, 4, 5, 6, 7, 8, 9, 10, 20, 50 or more strains from these taxa.

In certain embodiments, the method comprises administered to the subject an effective amount of a probiotic or a prebiotic composition or a combination thereof, wherein said composition(s) stimulates growth and/or activity or includes of one or more strains of bacteria from one or more species selected from the group consisting of *Faecalibacterium prausnitzii* and/or *Bacteroides uniformis* in the GI microbiota of the subject. In certain embodiments, the composition comprises at least 2, 3, 4, 5, 6, 7, 8, 9, 10, 20, 50 or more strains from these taxa.

Within a given composition, different bacterial strains can be contained in equal amounts (even combination) or in various proportions (uneven combinations) needed for achieving the maximal biological activity. For example, in a bacterial composition with two bacterial strains, the strains may be present in from a 1:10,000 ratio to a 1:1 ratio, from a 1:10,000 ratio to a 1:1,000 ratio, from a 1:1,000 ratio to a 1:100 ratio, from a 1:100 ratio to a 1:50 ratio, from a 1:50 ratio to a 1:20 ratio, from a 1:20 ratio to a 1:10 ratio, from a 1:10 ratio to a 1:1 ratio. For bacterial compositions comprising at least three bacterial strains, the ratio of strains may be chosen pairwise from ratios for bacterial compositions with two strains. For example, in a bacterial composition comprising bacterial strains A, B, and C, at least one of the ratios between strain A and B, the ratio between strain B and C, and the ratio between strain A and C may be chosen, independently, from the pairwise combinations above. In one specific embodiment, the invention encompasses administering two or more bacteria-containing compositions to the same subject. Such compositions can be administered simultaneously or sequentially.

In one embodiment of any of the above methods of the invention, the probiotic is administered in a therapeutically effective amount. The dosages of the microbiota inoculum and/or probiotic composition administered in the methods of the invention will vary widely, depending upon the subject's physical parameters, the frequency of administration, the manner of administration, the clearance rate, and the like. The initial dose may be larger, and might be followed by smaller maintenance doses. The dose may be administered as infrequently as weekly or biweekly, or fractionated into smaller doses and administered daily, or more than once a day, semi-weekly, etc., to maintain an effective dosage level. It is contemplated that a variety of doses will be effective to achieve colonization, e.g. $10^6$, $10^7$, $10^8$, $10^9$, and $10^{10}$ CFU for example, can be administered in a single dose. Lower doses can also be effective, e.g., $10^4$, and $10^5$ CFU.

The probiotic composition useful in any of the above methods can comprise, without limitation, e.g., live bacterial cells, conditionally lethal bacterial cells, inactivated bacterial cells, killed bacterial cells, spores (e.g., germination-competent spores), recombinant carrier strains, cell extract, and bacterially-derived products (natural or synthetic bacterially-derived products such as, e.g., bacterial antigens or bacterial metabolic products).

Bacterial strains administered in probiotic compositions according to the methods of the present invention can comprise live bacteria. One or several different bacterial inoculants can be administered simultaneously or sequentially (including administering at different times). Such bacteria can be isolated from the GI tract and grown in culture. The present invention also comprises administering "bacterial analogues", such as recombinant carrier strains expressing one or more heterologous genes derived from the relevant bacterial species. The use of such recombinant bacteria may allow the use of lower therapeutic amounts due to higher protein expression. Non-limiting examples of recombinant carrier strains useful in the methods of the present invention include *E. coli* and *Lactobacillus, Bacteroides* and *Oxalobacter*. Methods describing the use of bacteria for heterologous protein delivery are described, e.g., in U.S. Pat. No. 6,803,231.

In certain embodiments, the probiotic comprises a preparation of the GI microbiota of a healthy subject. A suitable donor might have no known infections or colonizations of disease associated microbes and viruses. A spouse or family method without evidence of disease might be suitable. It might be best to transfer a carefully selected collection or consortium of commensal bacteria, with or without pretreatment that would facilitate colonization and prevent recurrence of the disease-associated taxa (i.e., species and strain).

Methods for producing bacterial compositions of the invention may include three main processing steps, combined with one or more mixing steps. The steps are: organism banking, organism production, and preservation. For banking, the strains included in the bacterial compositions of the invention may be (1) isolated directly from a specimen or taken from a banked stock, (2) optionally cultured on a nutrient agar or broth that supports growth to generate viable biomass, and (3) the biomass optionally preserved in multiple aliquots in long-term storage. The bacterial suspension can be freeze-dried to a powder and titrated. After drying, the powder may be blended to an appropriate potency, and mixed with other cultures and/or a filler such as microcrystalline cellulose for consistency and ease of handling, and the bacterial composition formulated as provided herein.

In one embodiment of any of the above methods of the invention, the probiotic is delivered to the subject in a form of a suspension, a pill, a tablet, a capsule, or a suppository. In another embodiment, the probiotic is delivered to the subject in a form of a liquid, foam, cream, spray, powder, or gel. In yet another embodiment, the probiotic is delivered to the subject in a saline suspension for use in feeding tubes, transmission via nasogastric tube, or enema. If live bacteria are used, the carrier should preferably contain an ingredient that promotes viability of the bacteria during storage.

The formulation can include added ingredients to improve palatability, improve shelf-life, impart nutritional benefits, and the like. If a reproducible and measured dose is desired, the bacteria can be administered by a rumen cannula.

In one embodiment of any of the above methods of the invention, the bacterial inoculum is delivered to the subject in a form of a composition which comprises (i) a carrier and/or excipient and/or (ii) one or more prebiotic agents which stimulate growth and/or activity of one or more bacteria present in the composition. In one specific embodiment, said composition comprises an excipient or a carrier that optimizes the seeding of the transferred microbiota.

In one embodiment of any of the above methods involving administration of a probiotic composition, said probiotic composition is reconstituted from a lyophilized preparation. In one embodiment of any of the above methods involving administration of a probiotic composition, said probiotic composition comprises a buffering agent to adjust pH.

In one embodiment, the probiotic composition comprises a buffering agent (e.g., sodium bicarbonate, infant formula, or other agents which allow bacteria to survive and grow [e.g., survive in the acidic environment of the stomach and to grow in the intestinal environment]), along with preservatives, stabilizers, binders, compaction agents, lubricants, dispersion enhancers, disintegration agents, antioxidants, flavoring agents, sweeteners, and coloring agents.

In one embodiment of any of the above methods involving administration of a probiotic composition, the probiotic composition is administered conjointly with a prebiotic which stimulates growth and/or activity of bacteria contained in the probiotic composition. Non-limiting examples of useful prebiotics include, e.g., galactose, $\beta$-N-Acetyl-$\alpha$-glucosamine, pyroglutamtamic acid, arginine, serine, glycine, fructooligosaccharides (FOS), galactooligosaccharides (GOS), human milk oligosaccharides (HMO), Lacto-N-neotetraose, D-Tagatose, xylo-oligosaccharides (XOS), arabinoxylan-oligosaccharides (AXOS), N-acetylglucosamine, N-acetylgalactosamine, glucose, arabinose, maltose, lactose, sucrose, cellobiose, amino acids, alcohols, resistant starch (RS), electrolytes and any combinations thereof. In some embodiments, the electrolytes can modulate or balance the pH. In one specific embodiment, the probiotic and prebiotic are administered in one composition, or simultaneously as two separate compositions, or sequentially.

Formulations and Combination Treatments

Oral delivery may also include the use of nanoparticles that can be targeted, e.g., to the GI tract of the subject, such as those described in Yun et al., Adv Drug Deliv Rev. 2013, 65(6):822-832 (e.g., mucoadhesive nanoparticles, negatively charged carboxylate- or sulfate-modified particles, etc.). Non-limiting examples of other methods of targeting delivery of compositions to the GI tract are discussed in U.S. Pat. Appl. Pub. No. 2013/0149339 and references cited therein (e.g., pH sensitive compositions [such as, e.g., enteric polymers which release their contents when the pH becomes alkaline after the enteric polymers pass through the stomach], compositions for delaying the release [e.g., compositions which use hydrogel as a shell or a material which coats the active substance with, e.g., in vivo degradable polymers, gradually hydrolyzable polymers, gradually water-soluble polymers, and/or enzyme degradable polymers], bioadhesive compositions which specifically adhere to the colonic mucosal membrane, compositions into which a protease inhibitor is incorporated, a carrier system being specifically decomposed by an enzyme present in the colon).

For oral administration, the active ingredient(s) can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

In one aspect, the invention provides a method for treating (including preventing) SLE and lupus nephritis as well as inflammatory diseases such as, but not limited to, glomerulonephritis (e.g., IgA nephropathy) and inflammatory bowel disease (IBD) (e.g., ulcerative colitis and Crohn's disease) in a subject in need thereof, said method comprises administering a compound or composition that inhibits growth and/or activity of one or more strains of bacteria (as disclosed above) in combination with administering a probiotic and/or a prebiotic composition that stimulates growth and/or activity of one or more strains of bacteria (as disclosed above). In certain embodiments, the compound or composition that inhibits growth and/or activity of one or more strains of bacteria is administered before the probiotic and/or prebiotic composition(s). In certain embodiments, the compound or composition that inhibits growth and/or activity of one or more strains of bacteria is administered after the probiotic and/or prebiotic composition(s). In certain embodiments, the compound or composition that inhibits growth and/or activity of one or more strains of bacteria is administered at the same time as the probiotic and/or prebiotic composition(s). In certain embodiments, the growth is inhibited to the extent that the bacterial strains are removed from the microbiota (i.e., reduced or ablated). In certain embodiments, additional other therapeutic methods/agents (as disclosed below) can be co-administered (simultaneously or sequentially) with the combination inhibitory and stimulatory therapy to generate additive or synergistic effects.

It is also contemplated that when used to treat SLE or lupus nephritis as well as inflammatory diseases such as, but not limited to, glomerulonephritis (e.g., IgA nephropathy) and inflammatory bowel disease (IBD) (e.g., ulcerative colitis and Crohn's disease), the compositions and methods of the present invention can be utilized with other therapeutic methods/agents suitable for the same or similar cancers or tumors. Such other therapeutic methods/agents can be co-administered (simultaneously or sequentially) to generate additive or synergistic effects. Suitable therapeutically effective dosages for each agent may be lowered due to the additive action or synergy.

In one embodiment of any of the above methods of the invention, the method further comprises administering to the subject one or more additional compounds selected from the group consisting of immuno-suppressives, biologicals, probiotics, prebiotics, and cytokines (e.g., IFN or IL-22).

In certain embodiments, the compositions can be administered with an effective amount of anti-inflammatory drugs (NSAIDs), antimalarial agents, corticosteroids, azathioprine, mycophenolate, methotrexate, leflunomide, belimumab, and Vitamin D.

In certain embodiments, the antimalarial agent can be used to treat an autoimmune disease. In certain embodiments, the antimalarial drug is amodiaquine, chloroquine, chlorproguanil HCl, halofantrine HCl, mefloquine HCl, proguanil HCl, pyrimethamine, quinine sulfate, or hydroxychloroquine. In certain embodiments, the antimalarial agent is hydroxychloroquine.

In certain embodiments, the corticosteroid is prednisone, hydrocortisone, prednisolone, dexamethasone, alclometasone dipropionate, amcinonide, beclamethasone dipropionate, betamethiasone benzoate, betamethasone dipropionate, betamethasone valerate, budesonide, clobetasol propionate, clobetasone butyrate, desonide, desoxymethasone, diflorasone diacetate, diflucortolone valerate, flumethasone pivalate, fluclorolone acetonide, fluocinolone acetonide, fluocinonide, fluocortin butyl, fluocortolone preparations, fluprednidene acetate, flurandrenolone, halcinonide, hydrocortisone, hydrocortisone acetate, hydrocortisone butyrate, methylprednisolone acetate, mometasone furoate, or triamcinolone acetonide. In certain embodiments, the corticosteroid is prednisone or hydrocortisone or prednisolone or dexamethasone.

As a non-limiting example, the invention can be combined with other therapies that block inflammation (e.g., via blockage of ILL INFα/β, IL6, TNF, IL23, etc.) or inhibitors of specific cytoplasmic tyrosine kinases alone or in combination with a compound that is an Janus kinase inhibitor.

The methods and compositions of the invention can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 41BB, OX40, etc.). The methods of the invention can be also combined with other treatments that possess the ability to modulate NKT function or stability, including but not limited to CD1d, CD1 d-fusion proteins, CD1d dimers or larger polymers of CD1d either unloaded or loaded with antigens, CD1d-chimeric antigen receptors (CD1d-CAR), or any other of the five known CD1 isomers existing in humans (CD1a, CD1b, CD1c, CD1e).

In certain embodiments, a conditional lethal bacterial strain can be utilized as the inoculant or to deliver a recombinant construct. Such a conditional lethal bacterial strain survives for a limited time typically when provided certain nutritional supplements. It is contemplated that such a supplement could be a liquid, formulated to contain the nutritional component necessary to keep the bacteria alive. It is further contemplated that a patient/subject would drink such a supplement in intervals to keep the bacteria alive. Once the supplement is depleted, the conditional lethal bacteria die. Methods relating to conditional lethal strains of *H. pylori* are described in U.S. Pat. No. 6,570,004. In certain embodiments, the methods entail use of a bacteriophage that modulates the representation or the specific gene product expression of the bacterial strain (e.g., the strain of *R. gnavus*).

Spores used in the compositions of the invention can be isolated, for example, by solvent treatments (e.g., using partially miscible, fully miscible or an immiscible solvent), chromatographic treatments (e.g., using hydrophobic interaction chromatography (HIC) or an affinity chromatography), mechanical treatments (e.g., blending, mixing, shaking, vortexing, impact pulverization, and sonication), filtration treatments, thermal treatments (e.g., 30 seconds in a 100° C. environment followed by 10 minutes in a 50° C.), irradiation treatments (e.g., with ionizing radiation, typically gamma irradiation, ultraviolet irradiation or electron beam irradiation provided at an energy level sufficient to kill pathogenic materials while not substantially damaging the desired spore populations), centrifugation and density separation treatments (e.g., using density or mobility gradients or cushions (e.g., step cushions), such as, e.g., CsCl, Percoll, Ficoll, Nycodenz, Histodenz or sucrose gradients). It is generally desirable to retain the spore populations under non-germinating and non-growth promoting conditions and media, in order to minimize the growth of pathogenic bacteria present in the spore populations and to minimize the germination of spores into vegetative bacterial cells.

The compositions of the invention can comprise a carrier and/or excipient. While it is possible to use a bacterial inoculant or compound of the present invention for therapy as is, it may be preferable to administer it in a pharmaceutical formulation, e.g., in admixture with a suitable pharmaceutical excipient and/or carrier selected with regard to the intended route of administration and standard pharmaceutical practice. The excipient and/or carrier must be "acceptable" in the sense of being compatible with the other ingredients of the formulation and not deleterious to the recipient thereof. Acceptable excipients and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient and carrier can be selected with regard to the intended route of administration and standard pharmaceutical practice. Oral formulations readily accommodate additional mixtures, such as, e.g., milk, yogurt, and infant formula. Solid dosage forms for oral administration can also be used and can include, e.g., capsules, tablets, caplets, pills, troches, lozenges, powders, and granules. Non-limiting examples of suitable excipients include, e.g., diluents, buffering agents (e.g., sodium bicarbonate, infant formula, or other agents which allow bacteria to survive and grow [e.g., survive in the acidic environment of the stomach and to grow in the intestinal environment]), preservatives, stabilizers, binders, compaction agents, lubricants, dispersion enhancers, disintegration agents, antioxidants, flavoring agents, sweeteners, and coloring agents. Additional specific examples of suitable carriers and/or excipients include, e.g., vegetable cellulose, vegetable stearic acid, vegetable magnesium stearate, and/or silica. Those of relevant skill in the art are well able to prepare suitable solutions.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1. SLE and Microbiome

Figure 2A:
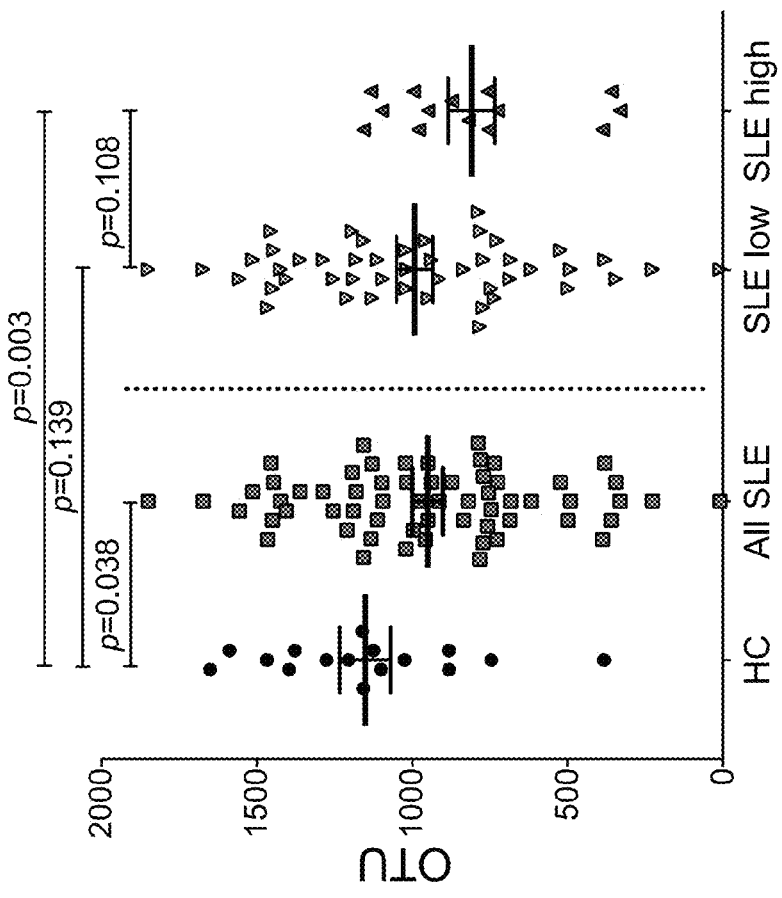
FIGS. 2A-2C. SLE patients with active disease have altered communities of commensal taxa in fecal samples. (2A) To estimate the relative species diversity, Chao1 alpha diversity was evaluated that represents the total expected number of operational taxonomic units (OTUs), which define quasi-species from 16S rRNA gene surveys. The larger values represent higher diversity. SLE patients (N=61) have less diverse intestinal microbiota than healthy controls (N=17), indicating SLE commonly have intestinal dysbiosis. Examination of the distribution of Chao1 values showed that SLE patients with high disease activity (i.e., SLEDAI>7) had contracted microbiomes vs. healthy adult controls (HC), and a trend towards more limited diversity (lower mean Chao1) compared to SLE with low disease activity. This cut-point was associated with greatest statistically significant differences. The SLE Low group, have the range of SLEDAI scores of 0-7 (N=47), and SLE high group have scores of 8-18 (N=14). (2B) Principal coordinates analyses (PCoA) show that the beta diversity within bacterial communities in the fecal microbiomes in healthy subjects is less different from SLE patients (PERMANOVA, P=0.02). Furthermore, healthy subjects were more like one another than were SLE patients. (2C) Based on Shannon-Jensen distances (JSD), the microbiota communities in healthy subjects are more like one another than SLE patients with low disease activity, with even greater differences are seen in SLE with high disease activity (P=0.002). Significance based on Mann-Whitney test.
Figure 2B:
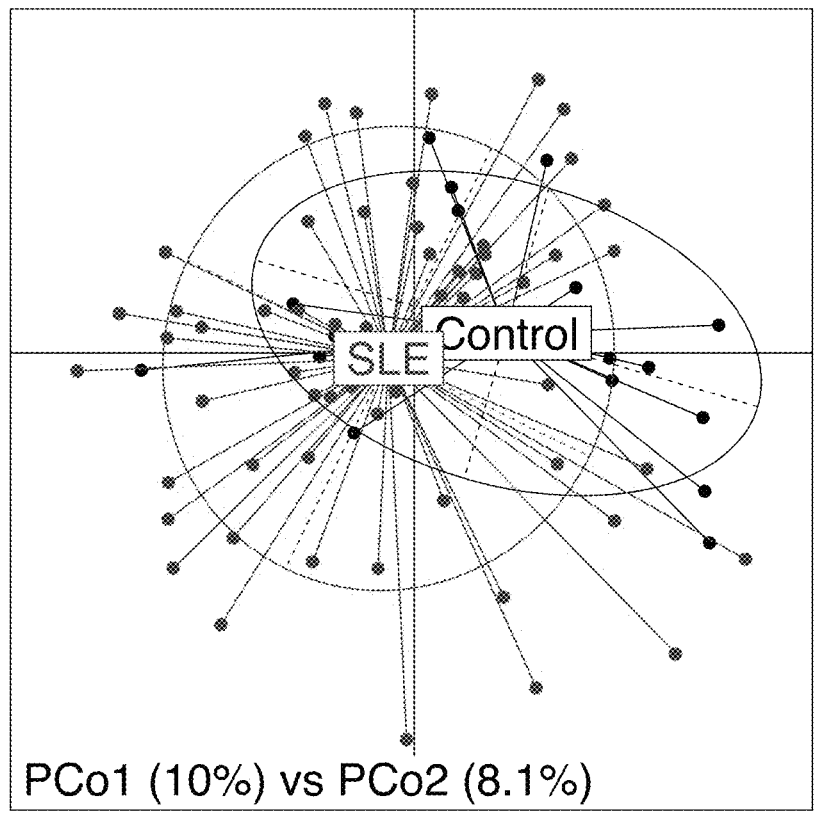
Figure 2C:
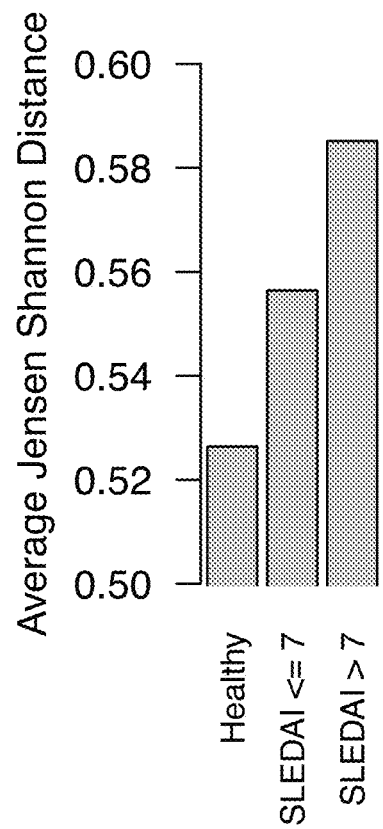

A cross-sectional cohort of 130 adult multiethnic SLE patients, including three or more longitudinal samples from 6 patients, and 8 sample sets from patients at onset before start of medications, with SLEDAI from 0 to 19 was recruited. Six others were flaring off medications. From the 16S surveys of the fecal microbiome, it was surprisingly discovered that these SLE patients have recurrent patterns of dysbioses in their intestinal microbiomes (23, 24). Immunologic studies and fecal microbiome surveys of 61 Lupus patients and 18 healthy adult controls were completed. There were greater than 30 million assignable 16S reads for 243 samples. There was a clear difference in the microbiota of SLE patients in the richness of the fecal microbiomes (i.e., alpha diversity by Chao1 analysis) (FIG. 2A), compared to healthy controls, and significant differences in the composition of their microbiomes based on taxa (FIG. 2C).

The Hygiene Hypothesis postulates that the limited exposure to microorganisms in industrialized countries, due to improved sanitary conditions, reduces complexity and skews our microbiomes, which promotes the development of allergic and autoimmune diseases (41). At a phylum level, akin to the dysbioses reported in IBD patients (42, 43), active SLE have expansions of Proteobacteria and Bacteroidetes, but a paucity of Actinobacteria and Firmicutes. Changes in the microbiome did not correlate with disease duration or current medication (although in this cohort it was difficult to discount hydroxychloroquine as nearly every Lupus patient is on this medication). Patients were also categorized by composite SLEDAI score (44-47), which was developed to aid treatment decisions. While patients with low SLEDAI were more similar to healthy controls, the abundance of distinct taxa in patients with SLEDAI>7 (high disease) showed even greater reduction in microbiome alpha diversity (FIGS. 2A, 2C). In patients in remission and off immunologically active medications (and had low SLEDAI scores, these patients have intestinal communities that can be similar to a healthy gender/age-matched individual (see FIGS. 2A and 2B). In contrast, in patients with greater disease severity these imbalances are generally more severe.

In the SLE fecal microbiome significant global shifts with altered representation in defined individual taxa, at the family, genus and (quasi-) species level (Table 1) were found. Patients with SLEDAI low disease activity were generally more similar to healthy patients, while microbiome shifts were more marked in Lupus patients with higher disease activity (FIG. 2), with a progressive gradient.

TABLE 1

| Shifts in Taxa abundance in SLE and by disease activity compared to healthy | | | | | |
|---|---|---|---|---|---|
| | Taxonomy | Healthy | SLEDAI_Low | SLEDAI_High | P value |
| Class | Mollicutes | 2.13% | 0.07% | 0.21% | 0.008 |
| Order | RF39 | 2.11% | 007% | 0.21% | 0.022 |
| Family | Veillonellaceae | 1.68% | 3.41% | 12.27% | 0.009 |
| Family | [Barnesiellaceae] | 1.56% | 0.83% | 0.42% | 0.045 |
| Genus | *Lachnospira* | 1.19% | 0.25% | 0.62% | 0.045 |
| Genus | *Acidaminococcus* | 0.20% | 0.25% | 3.11% | 0.014 |
| Genus | *Faecalibacterium* | 1.08% | 0.65% | 0.53% | 0.026 |
| Genus | [*Ruminococcus*] | 0.64% | 1.76% | 3.15% | 0.013 |
| Species | *F. prausnitzii* | 1.07% | 0.64% | 0.52% | 0.022 |

TABLE 1-continued

Shifts in Taxa abundance in SLE and by disease activity compared to healthy

| | Taxonomy | Healthy | SLEDAI_Low | SLEDAI_High | P value |
|---|---|---|---|---|---|
| (decrease) Species (decrease) | *Bacteroides uniformis* | 1.95% | 0.87% | 0.35% | 0.016 |
| Species (increase) | *Ruminococcus gnavus* | 0.23% | 1.19% | 2.11% | 0.006 |

By Univariate Kruskal-Wallis ANOVA Analysis

Fecal samples from SLE with high disease activity have significant expansions of *R. gnavus* species (Table 1), which has been reassigned to the Lachnospiraceae family (discussed above). *R. gnavus* expansions have also been reported in some IBD patients with active inflammatory disease (42, 43). Complex inter-relationships within microbiome community were found. In individual microbiome communities, evidence that certain species are in dynamic and reciprocal relationships with each other was found (Table 1). Indeed, within a community from an active SLE patient, when there is an expansion of *R. gnavus*, there was significant reciprocal contraction of the putative protective species (48), *F. prausnitzii* (p<0.0002), after CLR normalization. The relative abundance of *R. gnavus* based on 16S sequence analysis taken from fecal samples of 61 SLE patients vs 17 healthy controls was: 1.348±0.258 vs 0.252±0.095, respectively (Mann Whitney two-tailed p=0.01).

The effects on B cells and antibodies was also studied, as these are intertwined with the gut immune development, and with Lupus pathogenesis. In fact, the intestine is one of the most important sources of antibody production in the body, which is overwhelmingly secretory IgA (sIgA). In the bowel, only a subset (~20%) of 16S defined bacterial taxa are coated with sIgA (24), representing direct evidence of immune recognition of accessible bacterial taxa-specific antigens in vivo. In SLE, certain operational taxonomic units (OTU) are preferentially represented among the sIgA-coated gut commensals. It was surprisingly found that overrepresentation of *Prevotella copri* (earlier implicated in new-onset RA) (23, 24).

In the intestines of both healthy adults and SLE patients, the *R. gnavus* species were commonly coated with high levels of secreted IgA, presumably because surface-factors are immunogenic for the gut-associated lymphoid tissue (GALT). Strains of *R. gnavus* are heterogeneous, as some may have protective properties (i.e., induce T regs) (26) others induce inflammatory cytokines (i.e., serum IL-17) (27). Strains of *R. gnavus* reportedly also vary in their capacity to use the host protective mucous layer as a nutritional source (28); genomes vary in genes for antibiotic peptides (called Lantibiotics) (29, 30), which suppress other taxa that compete in their metabolic space (30). Notably, within an individual SLE patient it was found that expansions of *R. gnavus* inversely correlate with contractions of *Faecalibacterium prausnitzii*, which is reported to have anti-inflammatory protective properties (31).

Example 2. *R. Gnavus* Strains Differ in Antigenicity for Serum IgG Antibody Responses in SLE Patients To study the bacterial antigens in *R. gnavus*, a total of 8 strains (Table 2) were examined (including from the BEI and ATCC repositories). After growth in culture, each extract was conjugated onto a separate Luminex immunoassay bead. *R. gnavus* strain CC55_001C, which we obtained from the BEI repository, was isolated from a patient with colonic cancer tumor biopsy. This donor was not known to have an autoimmune disease.

TABLE 2

Strains of *Ruminococcus gnavus*

| Strain number | Strain Identifier | Origin |
|---|---|---|
| 1 | 29149, VPI C7-9 (from ATCC) | Human stool |
| 2 | HM-1056, CC55_001C (from BEI) | Colonic biopsy |
| 3 | CD1 FAA 3 | Crohn's Disease community 1 - mucosal biopsy |
| 4 | 32-6-I 9 D6 FAA AN | Healthy Donor 6 feces |
| 5 | 2/1/58FAA | IBD Patient 58 mucosal biopsy |
| 6 | UC2 D5 FAA 1 | Ulcerative colitis community 2 - mucosal biopsy |
| 7 | OB21_GAM_25_AN | Obese community 1 - feces |
| 8 | WAL 14576 | Finegold lab strain isolate - feces |

The *R. gnavus* strains were cultured in chopped Meat Broth (CM), which supports the growth of most non-sporeforming and sporeforming anaerobes associated with human and animal infections. Cultures were incubated at 37° C. in an anaerobic (75% $N_2$, 20% $CO_2$, and 5% $H_2$) chamber for 2-7 days. Bacteria were then pelleted by centrifugation. Strain typing was confirmed by assigning OTU by 16S rDNA sequence, or OTU-specific QPCR.

Extracts were generated with Bugbuster™ buffer (EMD Millipore), following manufacturer's direction. This buffer includes both recombinant lysozyme and Benzonase nuclease. To reduce or remove antigenic proteins, Proteinase K was used, with the volume adjusted depending on the volume and concentration of the extracts and incubated at 55° C. for 10 min. Samples were pre-cleared using a table top eppendorf centrifuge. Reactivity of these preparations were then tested with multiplex bead based assays with detection with phycoerythrin labeled anti-human IgG were used (MagPix instrument, Luminex). Alternatively, bacterial samples were pre coating onto ½ surface area 96-well ELISA plate wells, and detection with horseradish peroxidase labeled goat anti-human IgG (gamma heavy chain specific (Jackson Immunoresearch). Alternatively, western immunoblots were used under reducing conditions that including boiling in sample buffer than included 2 mercaptoethanol.

Figure 3:
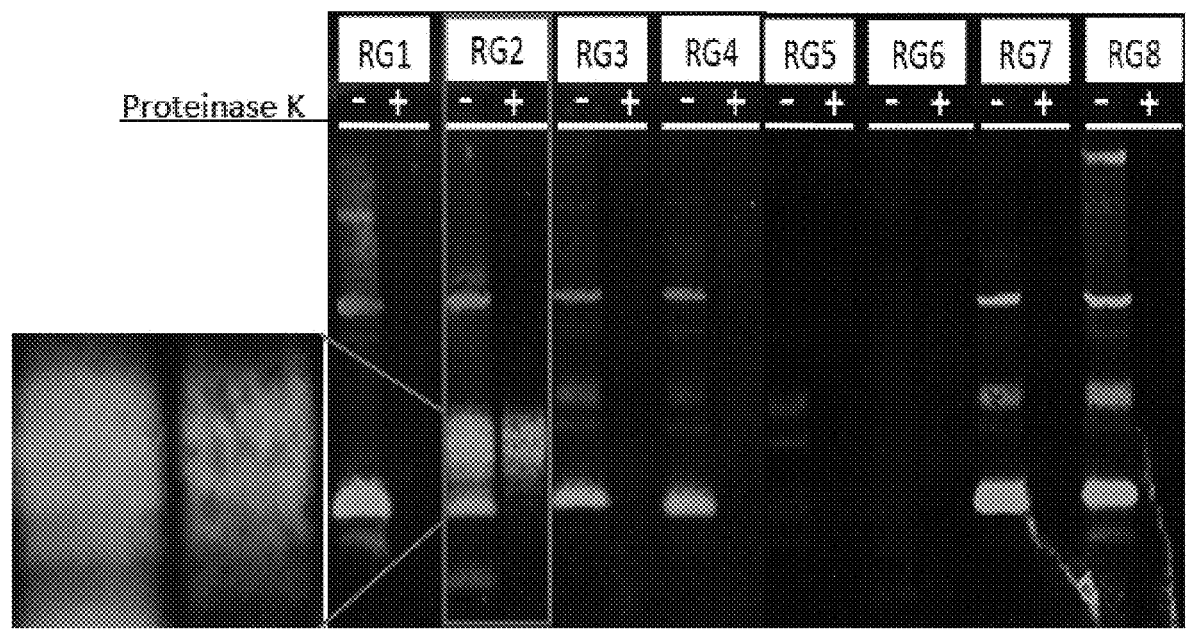
FIG. 3. Localization of immunodominant strain-associated non-protein non-nucleic acid antigen in Ruminococcus gnavus. Immunoblot of electrophoretically separated molecular species from 8 independent human strains of R. gnavus, termed RG1-RG8 (see Table 10). All preps were treated with lysozyme and Benzonase™, a non-specific nuclease, and then paired aliquots of each strain prep were run side-by-side, after thorough Proteinase K treatment of the prep at right. This panel shows representative results after the membrane was incubated with a dilution of a serum from the S-047 patient with active Lupus nephritis. Only extracts of the R. gnavus strain, CC55_001C, which was termed RG2, include nuclease-resistant proteinase-resistant clustered polymeric bands recognized by Lupus serum IgG, as shown in the left inset. These bands were commonly recognized by other Lupus sera, but not from unaffected individuals at the same dilution.
Figure 4A:
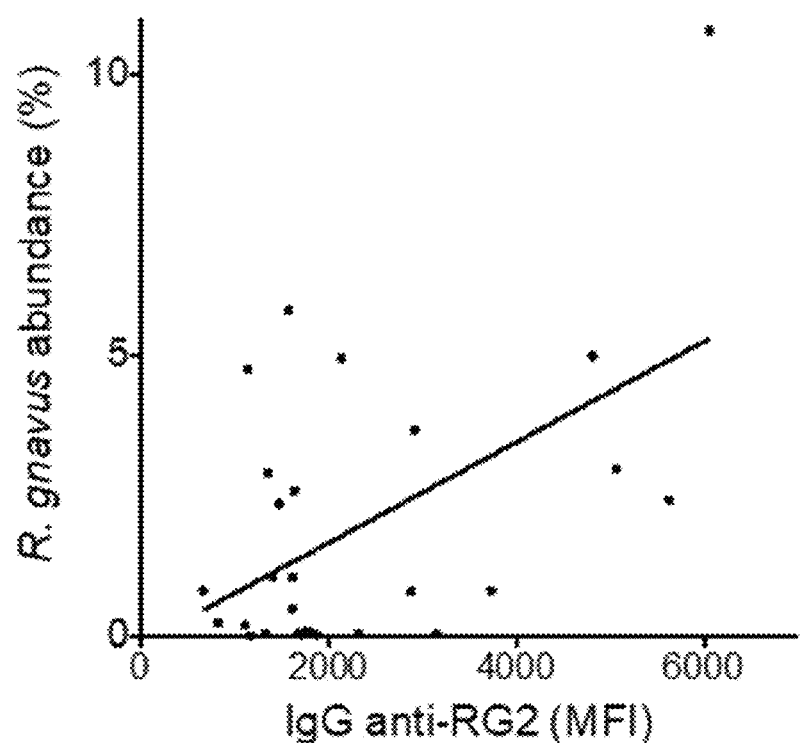
FIGS. 4A-4F. SLE patients with high disease activity have elevated levels of anti-RG2 strain-specific IgG antibodies. (4A) Abundance in fecal samples correlates with the levels of serum IgG anti-RG2 antibody from SLE patients (R=0.523). For these assays, the RG2 strain was anaerobically cultured and a treated extract, as well as those for other strains and other species, were each separately coupled to different paramagnetic beads (Luminex). (4B) Levels of serum IgG anti-RG2 are shown individually in groups of unaffected adults (see methods) and groups of Lupus-affected individuals from the NYU cohort. No significant bead binding was found for 7 other strains (see Table 10). SLE patients with high disease activity (SLEDAI>7) had much higher levels of IgG antibodies to the RG2 strain than healthy controls (p=0.0003), and SLE with low disease activity (p=0.002). (4C) Levels of serum IgG anti native DNA directly correlate with IgG anti-RG2 antibodies (R=0.625 p<0.0001). Results from multiplex assay. (4D) Levels of IgG anti-RG2 directly correlate with IgG to an extract of human glomeruli (R=0.52 p<0.0001). Results from multiplex assay. (4E) Levels of serum C3 inversely correlated with levels of serum Lupus IgG anti-RG2 antibodies in SLE patients. (4F) Levels of serum C4 inversely correlated with levels of serum Lupus IgG anti-RG2 antibodies in SLE patients. Results for 1:50 serum dilutions in bead-based immunoassays. Significance based on Mann-Whitney test. Pearson correlations shown.
Figure 4B:
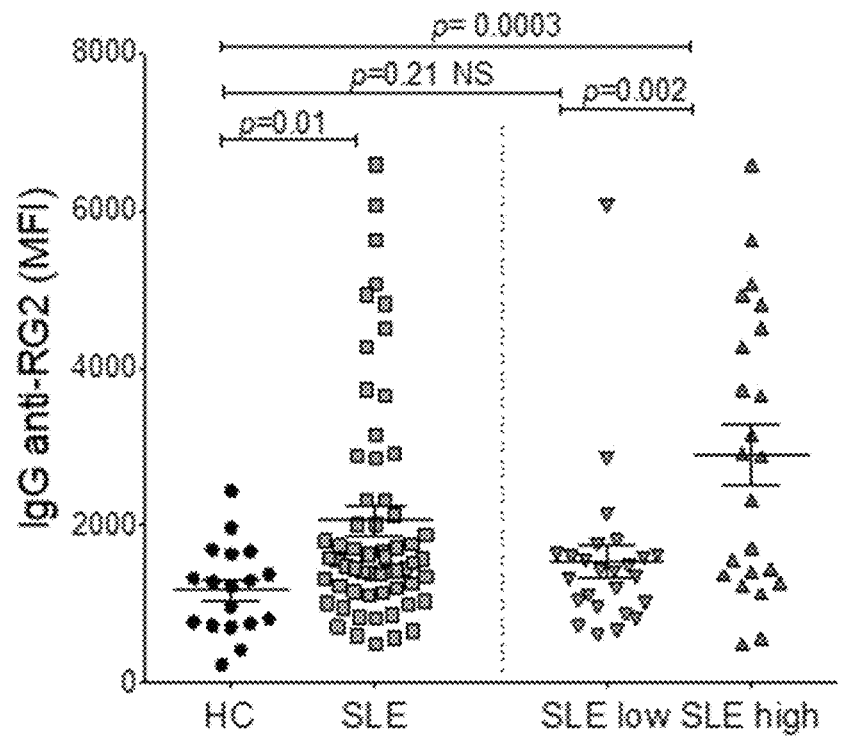

Significantly, SLE patients with high SLEDAI scores have significantly greater serum IgG anti-*R. gnavus* activity with the BEI strain alone (HM-1056, also termed strain CC55_001C) than responses in SLE with low disease activity or healthy controls (P<0.001) (FIG. 4B). These high IgG anti-BEI responses were generally associated with gut microbiomes with low alpha diversity. In other words, it was found that only the *R. gnavus* strain 2 has a non-protein antigen recognized by serum IgG of SLE patients, but not generally by healthy controls (FIG. 3).

Figure 4C:
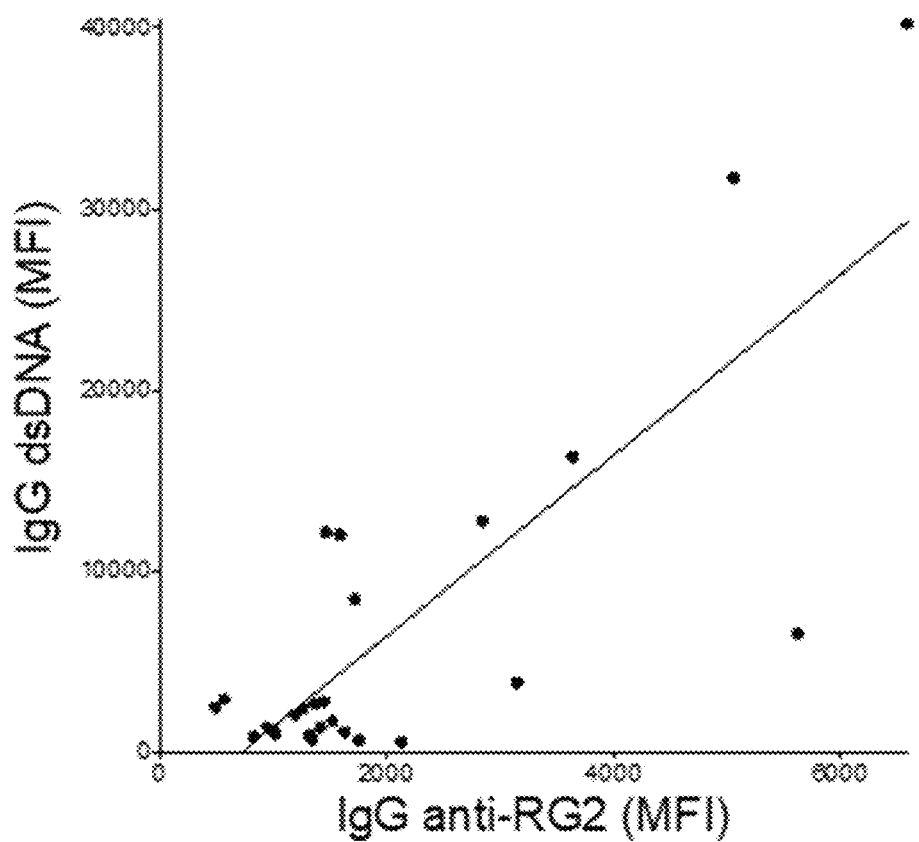
Figure 4D:
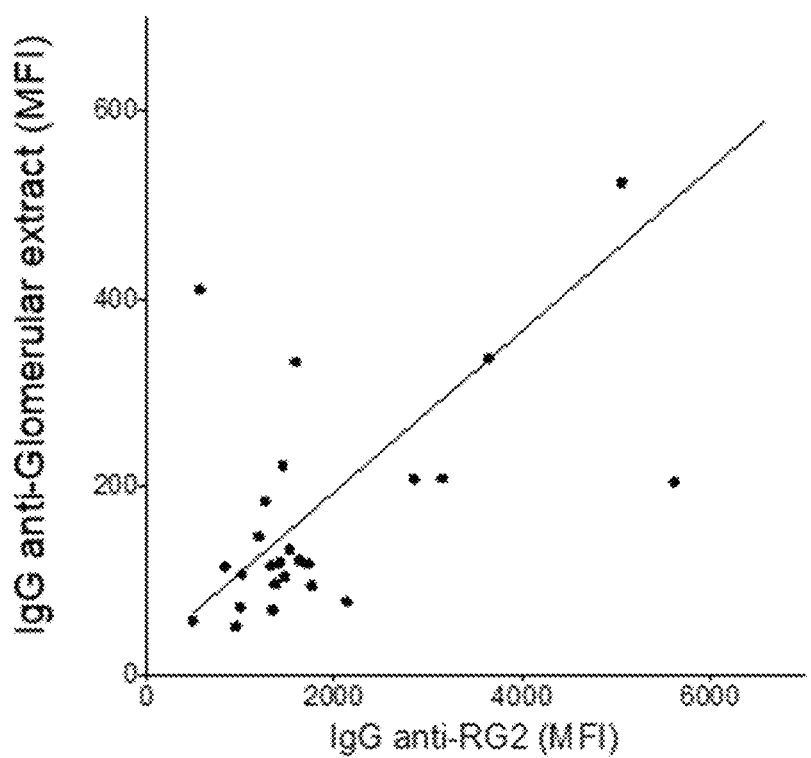
Figure 4E:
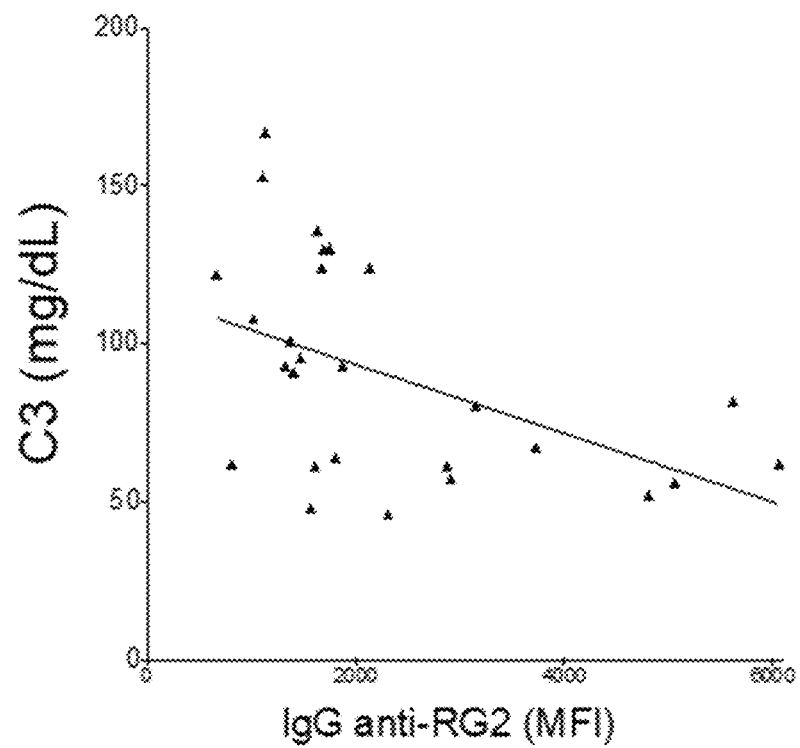
Figure 4F:
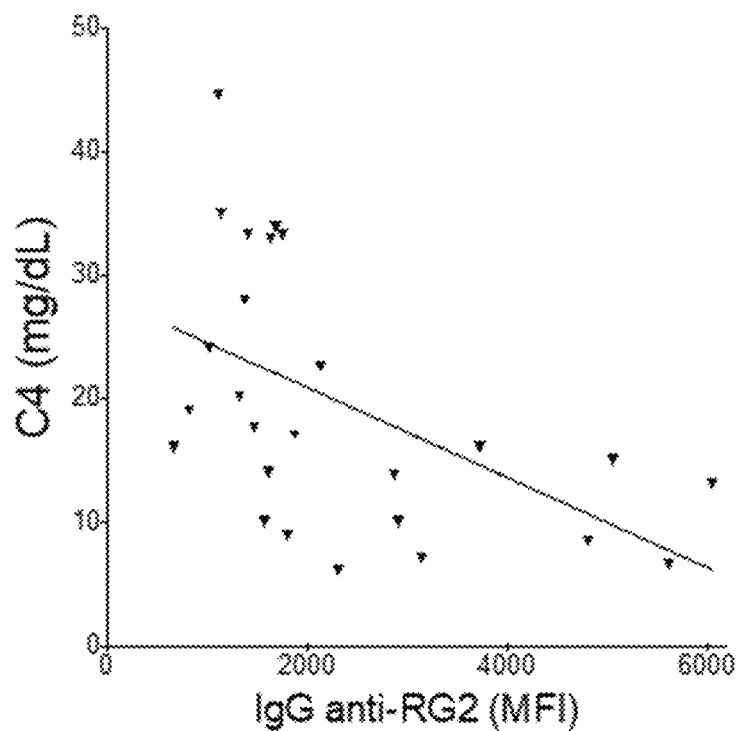

Levels of IgG anti-BEI strain antibodies strongly and directly correlate with those to dsDNA (P<0.0001) (FIG. 4C). Remarkably there was also strong direct relationship between IgG anti-*R. gnavus* and IgG to glomerular extract (P<0.0001), and inverse correlations with serum C3 (P<0.01) and C4 (P<0.006) (FIGS. 4E and 4F), which are markers of in vivo activation of the complement cascade. Strikingly, it was also found that in SLE patients, the abundance of fecal 16S rDNA reads assigned to *R. gnavus* is significantly and directly correlated with serum IgG specific for the BEI strain (P=0.02) (FIG. 4A), suggesting the burden of *R. gnavus* antigen(s) can be linked to host anti-*R. gnavus* IgG antibody responses.

Figure 10:
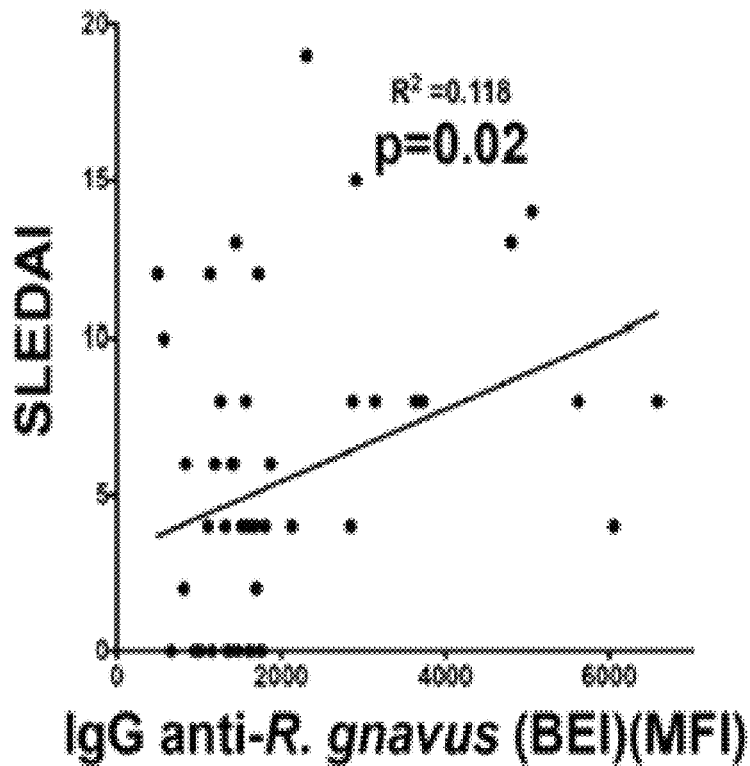
FIG. 10 Levels of serum BEI-strain 2-specific anti-*R. gnavus* antibodies are directly correlated with disease activity (SLEDAI) in an individual Lupus patient. Same data are shown dichotomized by disease activity in FIG. 4B.
Figure 11A:
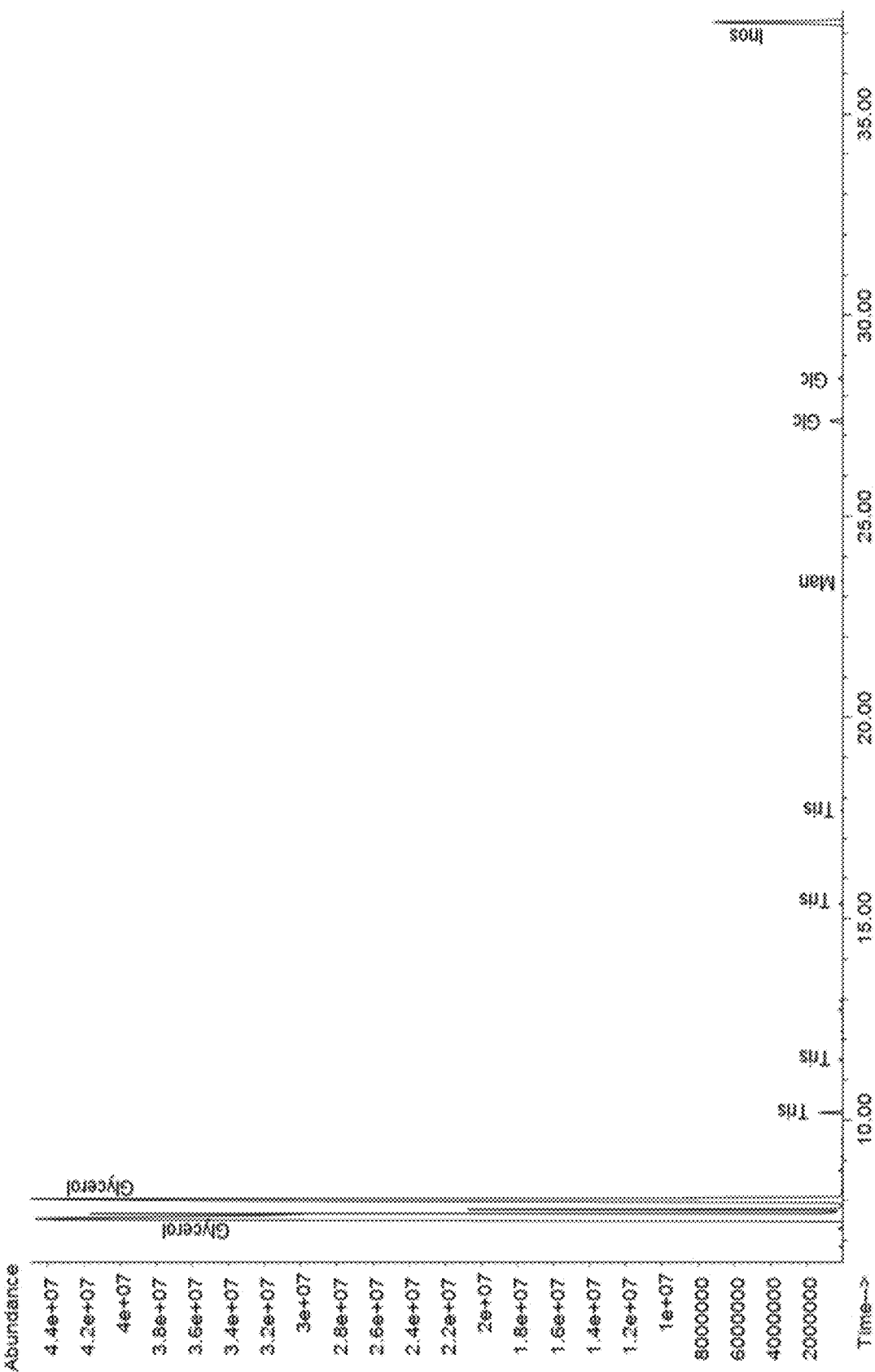
FIG. 11A-11D. Glycosyl composition analysis of bacterial samples: Total ion chromatogram (TIC) of the TMS-glycoside derivatives derived from the sample—(11A) sample #1 of RG2; (11B) sample #1 excluding the glycerol peaks of RG2; (11C) Sample #2 of RG2, (11D) sample #2 excluding glycerol peaks of RG2.
Figure 11B:
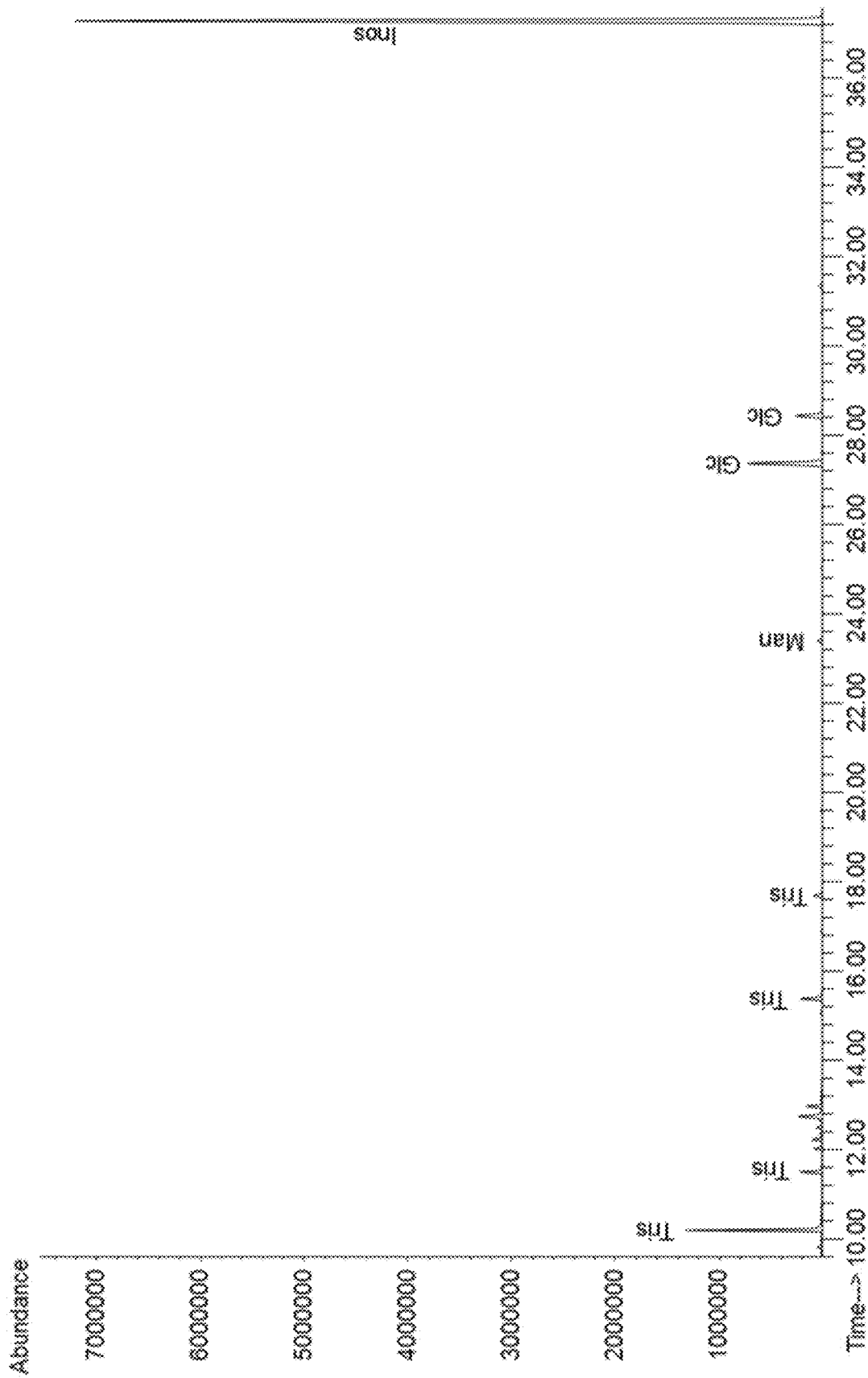
Figure 11C:
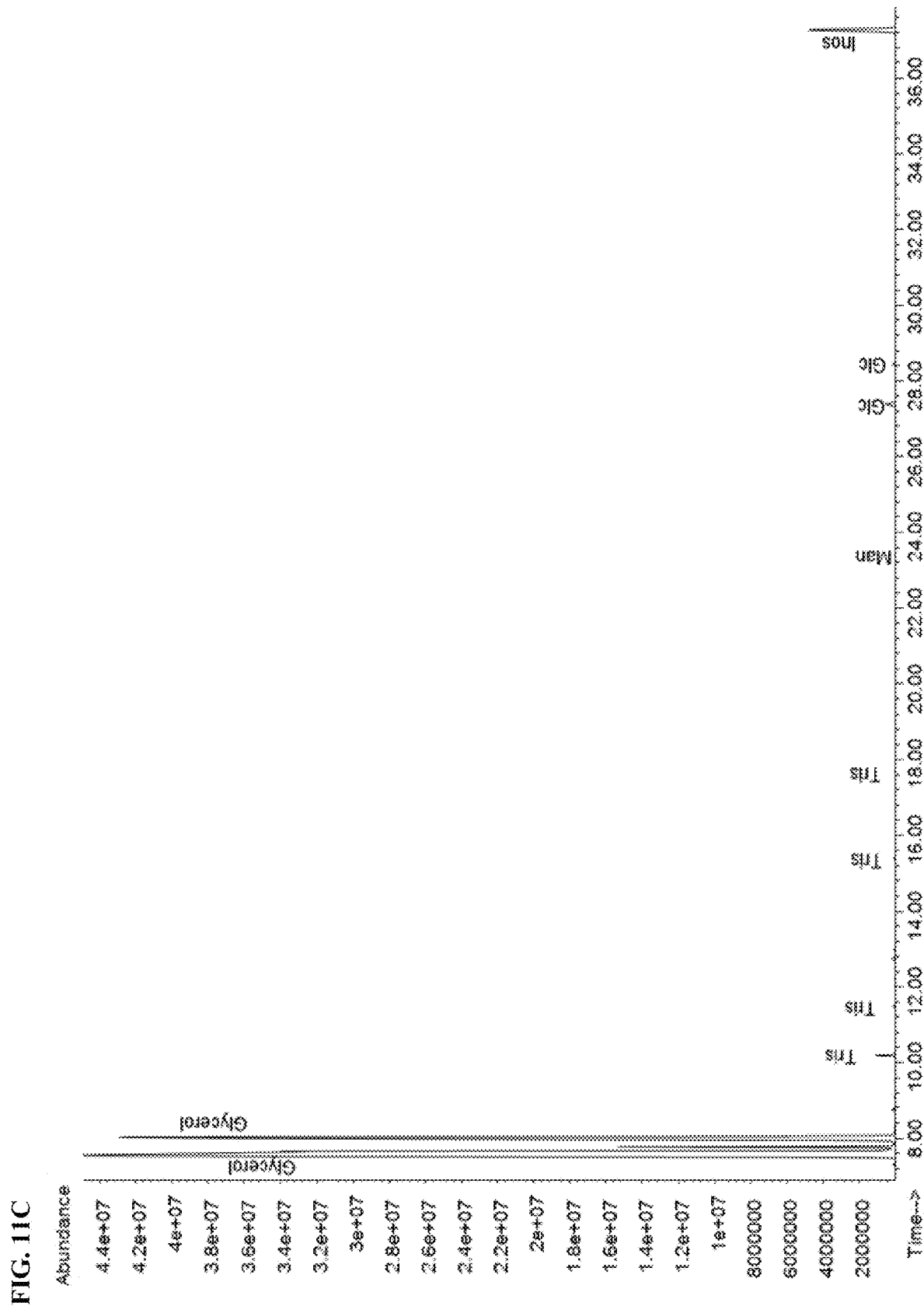
Figure 11D:
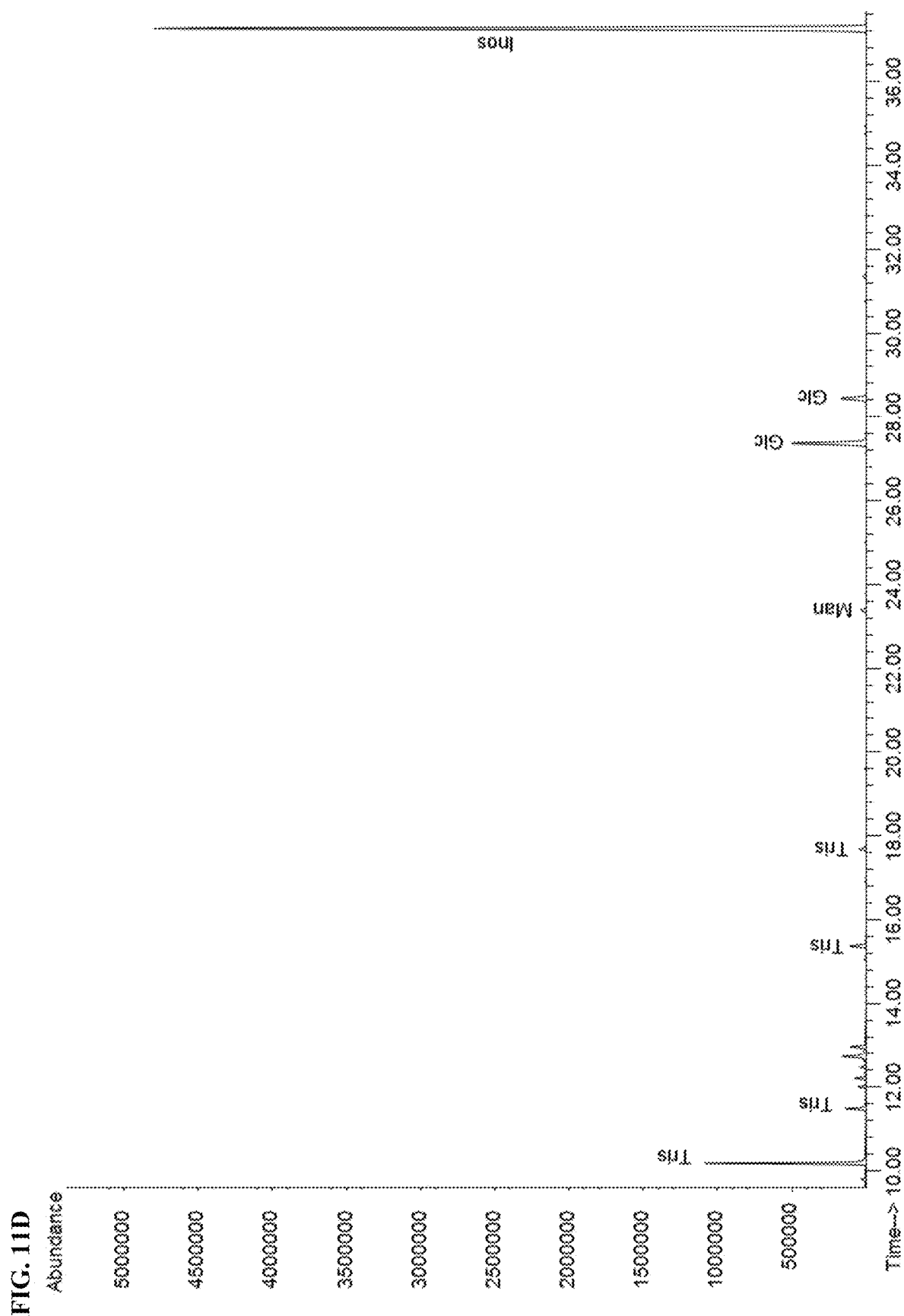

Levels of Lupus serum IgG to *R. gnavus* 2 (HM-1056, also termed strain CC55_001C) obtained from BEI) also significantly correlated with SLEDAI scores (P=0.02) (FIG. 10). It is hypothesized that this bacteria strain directed response may contribute to Lupus immune-complex mediated disease. The highest levels were present in active Lupus nephritis (by SLEDAI criteria), at the time of blood sampling (FIG. 6). Notably, all SLE patients with IgG to BEI *R. gnavus* predominantly recognize an oligomeric set of bands at ~22-25 kDa by IgG immunoblot that are resistant to DNAse, lysozyme, and protease treatment as demonstrated with Proteinase K (see FIG. 3).

It was postulated that these immune responses in Lupus patients are induced by a form of glycan or glycoconjugate, which is a highly immunogenic non-protein antigen that appears to be highly enriched in the cell wall of a strain of *R. gnavus*. This component is strongly recognized serum IgG responses from Lupus nephritis patients (which could be detected in samples at dilutions of 1:50 to >1:2000 in an assay). The inventors could also enrich for the representation of this glycan in a sample preparation simply by incubation of the bacteria in distilled water. Together, these results demonstrate that this is a cell wall associated glycoconjugate (FIG. 11 and Table 3). As such, Lupus disease activity appeared to be intertwined with a systemic immune response to a strain-specific glycan or lipoglycoconjugate antigenic compound. The data represents 10% of the overall sample amounts contained in each sample tube after 48 hours HF treatment. Glycosyl composition analysis of samples #1 and #2 indicated that the main residue at ~100 mol % was Glycerol. Detected carbohydrates were identified as small amounts of Glucose and Mannose as well as residues of Tris. The latter was likely a buffer contaminant. This signature documents the compound as a type of bacterial lipoglycan.

TABLE 3

Glycosyl composition analysis results of samples #1 and #2

| Sample | Glycosyl residue | Mass (µg) | Mol %[1] |
|---|---|---|---|
| #1 | Mannose (Man) | 0.2 | — |
|  | Glucose (Glc) | 4.5 | 0.1 |
|  | Glycerol | 1873.9 | 99.9 |
|  | SUM | 1878.6 | 100 |
| #2 | Mannose (Man) | 0.2 | — |
|  | Glucose (Glc) | 4.8 | 0.1 |
|  | Glycerol | 2493.8 | 99.9 |
|  | SUM | 2498.8 | 100 |

These data confirm the antigen of intrest includes carbohydrate moieties.
[1]Values are expressed as mole percent of total carbohydrate;
n.d.—not detected Together with the abundance of this antigen, it was hypothesized that this pathobiont strain produces a highly immunogenic cell wall lipoglycan. Lipoglycans are highly immunogenic substances and binding of circulating antibodies activates the complement cascade, and can trigger the release from neutrophils and macrophages of reactive oxygen and nitrogen species, and other factors that may act in synergy to amplify cell damage.

Lupus nephritis is believed to be an IgG immune complex-mediated disease (37). There are many possible scenarios by which lipoglycan-containing antigen from *R. gnavus* in the gut is passively released to enter the peripheral lymphoid tissue, where it induces high levels of lipoglycan-specific IgG antibodies. Induced host responses triggered by lipoglycan-containing antigen may then induce tissue injury, due in part to inherent or acquired defects in apoptotic clearance of injured cells that progress to secondary necrosis and release of nuclear antigens, and potentially other immune activation pathways associated with SLE. These postulated *R. gnavus* induced pathways of pathogenesis are reminiscent of post-immune responses to some strains of group *A. streptococci*, which can trigger immune complex glomerulonephritis with features and immune deposits akin to Lupus nephritis (38).

If it is assumed that lipoglycan is the dominant polysaccharide source in the samples, the molar amount of glycerol can be used to make a crude estimation of the amount of lipoglycan. For sample #1 the calculated amount of lipoglycan would be ~124 nmol/mg, whereas in sample #2 the amount of lipoglycan would be ~132 nmol/mg.

Example 3. SLE Gut Microbiome and Inflammatory Disease

Figure 12:
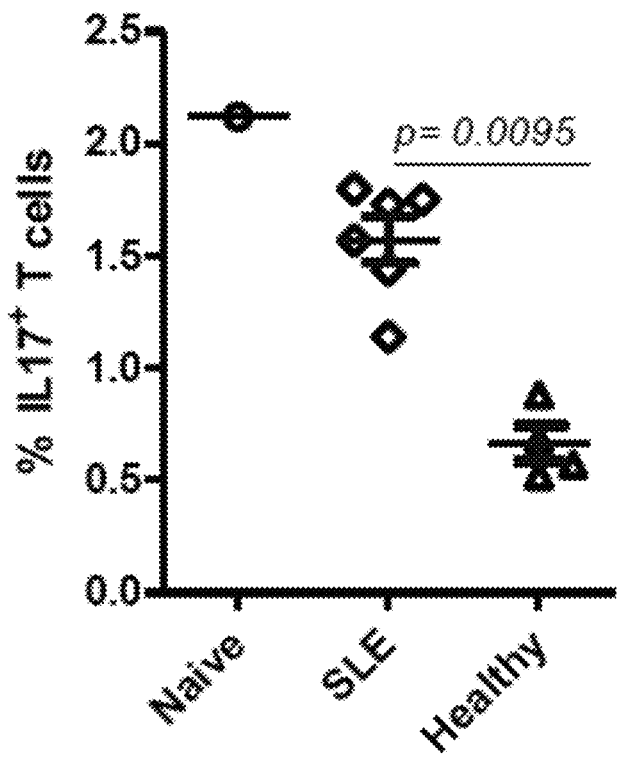
FIG. 12. SLE gut microbiome conveys expanded Th17 cells (IL17a producing) in gut lamina propria (LP) of adult C57BL/6: Female mice received 30 days of oral antibiotics, were rested for 3 days, then received three weekly gavages with fecal suspensions, and studied at 35 days. Results are shown for a naïve mouse, and for groups that received gut microbiome from active SLE patient (with *R. gnavus*) or a healthy control. Detected as per El Bannoudi H, et al., Eur J Immunol 2013; 43:439-46. Mann Whitney two-tailed t test, with mean SEM error bars. Levels of T regs were unchanged.

To investigate the potential for taxa in SLE gut microbiomes to contribute to inflammatory disease, an SLE patient was selected with an SLEDAI of 15 with active renal disease, and high serum IgG anti-*R. gnavus* 2 antigen (BEI strain specific) antibodies at time of sampling. Fecal suspensions were thrice gavaged weekly into B6 groups. After 40 days, mice were sacrificed, and results show the SLE microbiome induced expansions of Th17 cells in LP and in the spleen, and expanded IFNγ producing T cells (FIG. 12). These findings suggest active SLE patients have gut taxa with properties akin to SFB that can cause murine autoimmune disease (51-54).

Example 4. Multiplex Test

This example provides a multiplex assay that can help to identify patients with different probable diagnoses, such as inflammatory bowel disease (IBD), IgA Nephropathy, and/or lupus nephritis.

Diagnoses were made by clinical criteria or based on renal biopsy, as appropriate. A Magpix (Lumina) system was used with different beads coated with the indicated antigen. Two bacterial strains of *R. gnavus* (CC55_001C, HM-1056 and VPI C7-9, 29149) were grown, and extracts treated as described above in the disclosure.

Patients with SLE often have IgG autoantibodies to DNA, nucleosomes, glomerular extracts, Sm and C1q. The frequency of each type of autoantibody is different in different patients. IgG anti-Sm antibodies may support a diagnosis of SLE, but are not believed to be related to renal disease. Some IgG anti-DNA antibodies may be more common in patients with Lupus nephritis (also called Lupus glomerulonephritis). Class IV refers to a World Health Organization histology type of Lupus nephritis. Healthy subjects, and those with inflammatory bowel disease (ulcerative colitis and Crohn's disease), do not generally have abnormal results for tests associated with SLE. Values are italicized in Table 4 if they appear to be in the abnormally elevated range. The level associated with increased suspicion of disease was determined empirically by comparisons of groups of subjects known to be unaffected by the ailment, or who have been identified as having the disease based on clinical or histologic criteria. These results are relevant to understanding sensitivity and specificity of a test. These data were determined in duplicate diluted sample, at the dilutions indicated.

which was unaffected by nuclease and proteinase treatment, localized by EM-imaging to the cell-wall, with features of a lipoglycan. Furthermore, in three independent cohorts, this lipoglycan-containing-antigen was capable of dose-dependent inhibition of Lupus serum anti-native DNA antibodies, indicative of a form of molecular mimicry. The findings herein suggest a novel paradigm in which specific strains of a common gut commensal may affect the immunopathogenesis of Lupus glomerulonephritis.

The inventors have investigated the gut microbial communities in Lupus patients in search of host-commensal relationships that may contribute to autoimmune pathogenesis. To accomplish this goal, unbiased discovery surveys

TABLE 4

| | Sample | | R. gnavus CC55_001CC, HM-1056) | R. gnavus (VPI C7-9, 29149) | Ds DNA | Nucleosome | Glomerular Basement Membrane extract | Sm | Clq | Human Serum Albumin |
|---|---|---|---|---|---|---|---|---|---|---|
| Standard SLE | 1:200 | | *3896* | 2588 | *4127.25* | *10503* | *2456.5* | 35176 | *18354* | 1102.5 |
| Pool | 1:400 | | *2551.25* | 1552.5 | 2073.5 | *7946.25* | *1709.5* | *32507.25* | *13533.25* | 642.75 |
| Healthy | 1 1:50 | | 1240.75 | 130.75 | 4439 | 57 | 70 | 923.5 | 6471.75 | 26 |
| | 2 1:50 | | 823 | 299 | 600 | 141.75 | 240.75 | 617.5 | 3283 | 136.75 |
| | 3 1:50 | | 1455.5 | 555.5 | 530 | 264.5 | 335.5 | 1741 | 2948.75 | 233.5 |
| | 4 1:50 | | 751.5 | 339.75 | 453 | 392 | 283 | 751.5 | 3923.5 | 234.5 |
| SLE | SLE 1 1:50 | Class IV renal flare | *2456.75* | 1040.5 | *6325.5* | *10317* | *1475.5* | 6411.75 | 3805.75 | 200.25 |
| | SLE 2 (early/baseline timepoint) 1:50 | SLE renal activity unknown | 1369.25 | 873 | 3550.25 | 1566 | 1069 | *22603.25* | 5353 | 348.5 |
| | SLE 2 (Late/16 months later) 1:50 | Class IV renal flare | *4605.75* | 3837.75 | *11802* | *15067.75* | 481.5 | *35183.5* | 21302 | 1937.25 |
| | SLE 3 1:50 | SLE- not active | 1713.75 | 1113.25 | 971.75 | 1512 | 808.5 | *12221* | 3931.5 | 525 |
| | SLE 4 1:50 | SLE- not active | 2020.75 | 1280.75 | 1161.5 | 856.5 | 1178 | *18399.5* | 4465.25 | 506 |
| | SLE 5 1:50 | Class IV renal flare | *4553* | 696 | 2322.75 | *4277.75* | 937.5 | 2978 | *9895.5* | 174.25 |
| IBD | UC 1 1:50 | | 1128.25 | 305.75 | 593 | 267.25 | 187.25 | 1322.25 | 3236.75 | 84 |
| | UC 2 1:50 | | *2507* | 337 | *2935* | 275 | 132.25 | 713 | 3129.25 | 309.25 |
| | Crohns Disease 1:50 | | 2001 | 606 | *18603* | 781.5 | 666.25 | 2039.25 | *7190.25* | 392.75 |
| | UC 3 1:50 | | 647.25 | 413.5 | 441.5 | 345 | 310 | 764.5 | 2773.5 | 203 |
| | UC 4 1:50 | | *2199.25* | 327.5 | 925.5 | 308 | 199.75 | 2490.5 | 3098.5 | 252.5 |
| IgA nephropathy | IgAN 1 1:50 | Active renal | *4443* | 1302 | 3252 | 669 | 851 | 1925 | *17992* | 383 |

Example 5. Effects of *R. gnavus* on Immunopathogenesis of Lupus Glomerulonephritis In a discovery cohort, patients with high disease-activity displayed the most pronounced reductions in taxonomic complexity in faecal samples. Compared to healthy subjects, SLE patients had a five-fold overall mean greater representation of the *R. gnavus* species of the Lachnospiraceae family of obligate anaerobic gram-positive cocci, with reciprocal reductions of species with reported protective properties. *R. gnavus* abundance directly correlated with Lupus serum-IgG reactivity with one strain of this species but not with other tested strains. Levels of these strain-specific IgG correlated with composite disease-activity scores, and with active nephritis, and Class III, IV and V renal-biopsies. Lupus serum-IgG recognized a strain-associated antigen, were performed in a cross-sectional cohort of female lupus patients heterogeneous for ethnicity/race, disease activity, and organ involvement. These microbiome surveys were then followed by evaluations of autoantibody profiles and specific patient phenotypes. The resultant immunologic reactivities and phenotype associations were subsequently confirmed in two separate cohorts. The aggregate data demonstrated the interconnectedness in patients with Lupus nephritis (LN) between host pathologic autoimmune antinuclear antibody responses and immune recognition of a *R. gnavus* strain-associated bacterial antigen that in SLE patients functionally mimics mammalian DNA. The inventors' observations illuminate key features by which disease-associated outgrowths of certain strain(s) of an obligate anaerobe commensal, *R. gnavus*, may play a central role in immune-complex mediated Lupus disease.

Results

Patients with SLE have distinctive patterns of dysbiosis that parallel disease activity In the discovery phase of our studies, the inventors analyzed the faecal microbiota of 61 female patients with Lupus from a cross-sectional urban cohort and 17 female healthy controls (HC) (Table 7). Whereas prior investigations of microbiota in human Lupus have been limited to a small cohort with inactive disease (107), this cohort included patients with great heterogeneity in organ involvement and disease activity, from clinical remission to highly active, with patients scored using an updated version of the composite SLE disease activity index (SLEDAI) (108). Chao1 estimates of the total expected number of operational taxonomic units (OTUs) were used to define the richness of alpha diversity in gut communities (109).

TABLE 5

Abundance of Taxa in the Microbiome.

| Taxonomic level | Taxonomy | Healthy | SLEDAI$^{low}$ | SLEDAI$^{high}$ | p value |
|---|---|---|---|---|---|
| Family | Veillonellaceae | 1.68* | 3.41 | 12.27 | 0.009 |
| Family | Ruminococcaceae | 26.51 | 11.68 | 15.11 | 0.019 |
| Genus | Blautia | 2.17 | 4.10 | 3.50 | 0.058 |
| Genus | [Ruminococcus] | 0.64 | 1.76 | 3.15 | 0.013 |
| Species | Bacteroides uniformis | 1.95 | 0.87 | 0.35 | 0.016 |
| Species | Ruminococcus gnavus | 0.23 | 1.19 | 2.11 | 0.006 |

SLEDAI$^{low}$ was 0-7.
*Presented as percentage. Significant associations by univariate Kruskal analysis.

TABLE 6

Abundance in Lupus patients with renal disease.

| Taxonomic Level | Taxonomy | No Renal Disease Abundance (%) | Renal Disease Abundance (%) | p value |
|---|---|---|---|---|
| Phylum | Fusobacteria | 0.00 | 1.01 | 0.01 |
| Class | Erysipelotrichi | 0.72 | 3.68 | 0.00 |
| Class | Fusobacteriia | 0.00 | 1.01 | 0.01 |
| Order | Erysipelotrichales | 0.72 | 3.68 | 0.00 |
| Order | Fusobacteriales | 0.00 | 1.01 | 0.01 |
| Family | Erysipelotrichaceae | 0.72 | 3.68 | 0.00 |
| Family | Veillonellaceae | 3.40 | 6.89 | 0.03 |
| Family | Actinomycetaceae | 0.01 | 0.03 | 0.02 |
| Family | Peptostreptococcaceae | 0.01 | 0.08 | 0.05 |
| Family | [Paraprevotellaceae] | 0.69 | 1.17 | 0.04 |
| Family | Fusobacteriaceae | 0.00 | 0.99 | 0.00 |
| Genus | Veillonella | 0.27 | 1.07 | 0.03 |
| Genus | Actinomyces | 0.01 | 0.03 | 0.02 |
| Genus | Bilophila | 0.15 | 0.02 | 0.01 |
| Genus | [Ruminococcus] | 1.25 | 2.69 | 0.02 |
| Genus | Fusobacterium | 0.00 | 0.99 | 0.00 |
| Species | V. parvula | 0.01 | 0.17 | 0.02 |
| Species | V. dispar | 0.03 | 0.87 | 0.05 |
| Species | R. gnavus | 0.82 | 1.83 | 0.04 |

Tables 7a-c. Patients with Autoimmunity.

7a. NYU cohort SLE patients with microbiome data.

| NYU Patient ID | G | Age | Ethnicity | | Disease duration | SLEDAI score | Renal involvement by ACR at any time | Renal involvement at time of collection | Medications | Renal biopsy (WHO Class) |
|---|---|---|---|---|---|---|---|---|---|---|
| S-007 | F | 48 | Caucasian | Non hispanic | N/A | 4 | 1 | 0 | Pred 1 mg, HCQ, MMF 2000 mg | ND |
| S-009 | F | 55 | Asian | Non hispanic | 11 | 2 | 0 | 0 | Meth 20 mg, HCQ; MMF 1500 mg, Belim | ND |
| S-011 | F | 25 | Asian | Non hispanic | 14 | 4 | 1 | 0 | Pred 4 mg; HCQ | ND |
| S-012 | F | 34 | AA | Non hispanic | 4 | 2 | 0 | 1 | Pred 5 mg; HCQ; MMF 1500 mg | ND |
| S-013 | F | 45 | AA | Non hispanic | N/A | 2 | 1 | 1 | Pred 6 mg; HCQ; MMF 2000 mg | III/V |
| S-015 | F | 63 | White - Hispanic | Hispanic | N/A | 0 | 0 | 0 | HCQ; MTX 15 mg | ND |
| S-016 | F | 28 | AA | Non hispanic | 4 | 10 | 1 | 1 | Pred 60 mg; HCQ; AZA 150 mg | ND |
| S-020 | F | 31 | Caucasian | Non hispanic | N/A | 6 | 0 | 0 | Pred 12.5 mg; HCQ; Belim | ND |
| S-024 | F | 22 | Asian | Non hispanic | 15 | 8 | 1 | 1 | Pred 10 mg; HCQ; MMF 2000 mg | V |
| S-028 | F | 42 | Black - Hispanic | Hispanic | 11 | 2 | 1 | 1 | AZA 250 mg | ND |
| S-030 | F | 29 | White - Hispanic | Hispanic | 2 | 2 | 0 | 0 | Pred 10 mg; MTX 10 mg | ND |
| S-032 | F | 25 | Asian | Non hispanic | 3 | 0 | 0 | 0 | HCQ | N/A |

-continued

7a. NYU cohort SLE patients with microbiome data.

| NYU Patient ID | G | Age | Ethnicity | Disease duration | SLEDAI score | Renal involvement by ACR at any time | Renal involvement at time of collection | Medications | Renal biopsy (WHO Class) |
|---|---|---|---|---|---|---|---|---|---|
| S-036 | F | 29 | AA | Non hispanic | 16 | 14 | 1 | 1 | Pred 10 mg; HCQ; MMF 3000 mg | III/V |
| S-038 | F | 52 | Asian | Non hispanic | 15 | 4 | 1 | 1 | HCQ; MMF 2000 mg | ND |
| S-039 | F | 26 | AA | Non hispanic | 5 | 4 | 1 | 0 | HCQ; MMF 2000 mg | V |
| S-041 | F | 46 | White-Hispanic | Hispanic | N/A | 0 | 1 | 0 | Pred 10 mg; MMF 2000 mg | ND |
| S-047 | F | 38 | Asian | Non hispanic | 24 | 8 | 1 | 1 | Pred 5 mg; HCQ; AZA 150 mg; MMF 2000 mg | IV |
| S-049 | F | 47 | AA | Non hispanic | 12 | 2 | 0 | 0 | HCQ; AZA 100 mg | ND |
| S-052 | F | 62 | White-Hispanic | Hispanic | N/A | 2 | 0 | 0 | HCQ; MMF 2000 mg | ND |
| S-053 | F | 29 | AA | Non hispanic | 7 | 2 | 1 | 0 | HCQ; MTX 17.5 mg | ND |
| S-058 | F | 59 | AA | Non hispanic | 18 | 4 | 1 | 1 | HCQ; MMF 1000 mg | V |
| S-060 | F | 42 | White - Hispanic | Hispanic | 6 | 0 | 0 | 0 | None | ND |
| S-061 | F | 37 | Asian | Non hispanic | N/A | 8 | 0 | 1 | Pred 4 mg; HCQ | ND |
| S-062 | F | 44 | White - Hispanic | Hispanic | 24 | 0 | 1 | 1 | None | IV |
| S-063 | F | 33 | Asian | Non hispanic | 7 | 8 | 1 | 1 | HCQ; MMF 1000 mg | III/V |
| S-064 | F | 54 | White - Hispanic | Hispanic | 31 | 4 | 1 | 1 | HCQ | IV/V |
| S-070 | F | 68 | AA | Non hispanic | 13 | 4 | 0 | 0 | None | ND |
| S-072 | F | 79 | White-Hispanic | Hispanic | 42 | 0 | 0 | 0 | HCQ | ND |
| S-073 | F | 63 | AA | Non hispanic | 28 | 5 | 1 | 0 | Pred 5 mg | ND |
| S-075 | F | 58 | AA | Non hispanic | 39 | 0 | 1 | 0 | None | ND |
| S-078 | F | 34 | White-Hispanic | Hispanic | 9 | 8 | 0 | 1 | Pred 10 mg; HCQ; MMF 1500 mg | ND |
| S-079 | F | 30 | Black-Hispanic | Hispanic | 5 | 0 | 0 | 0 | HCQ | ND |
| S-080 | F | 47 | Caucasian | Non hispanic | 7 | 2 | 0 | 0 | HCQ | ND |
| S-081 | F | 49 | White-Hispanic | Hispanic | 7 | 2 | 0 | 0 | HCQ | ND |
| S-083 | F | 64 | Asian | Non hispanic | 29 | 2 | 1 | 0 | None | ND |
| S-086 | F | 37 | White-Hispanic | Hispanic | 3 | 12 | 1 | 1 | Pred 10 mg; HCQ; MMF 3000 mg | IV/V |
| S-088 | F | 23 | White-Hispanic | Hispanic | 6 | 13 | 1 | 1 | HCQ; AZA 100 mg | V |
| S-089 | F | 32 | Asian | Non hispanic | N/A | 8 | 1 | 1 | Pred 40 mg; HCQ | ND |
| S-093 | F | 75 | African American | Non hispanic | 56 | 2 | 0 | 0 | None | ND |
| S-096 | F | 31 | African American | Non hispanic | N/A | 0 | 1 | 0 | HCQ | ND |
| S-98 | F | 33 | White/Caucasian | Non hispanic | 17 | 4 | 0 | 0 | None | ND |
| S-102 | F | 61 | White-Hispanic | Hispanic | 15 | 0 | 0 | 0 | HCQ | ND |
| S-103 | F | 61 | AA | Non hispanic | 32 | 2 | 1 | 0 | HCQ | ND |
| S-113 | F | 24 | Caucasian | Non hispanic | 8 | 4 | 0 | 0 | Pred 5 mg; HCQ; AZA 100 mg | ND |
| S-115 | F | 38 | White-Hispanic | Hispanic | 12 | 8 | 1 | 1 | Pred 5 mg; HCQ | ND |

| 7a. NYU cohort SLE patients with microbiome data. | | | | | | | | | | |
|---|---|---|---|---|---|---|---|---|---|---|
| NYU Patient ID | G | Age | Ethnicity | | Disease duration | SLEDAI score | Renal involvement by ACR at any time | Renal involvement at time of collection | Medications | Renal biopsy (WHO Class) |
| S-120 | F | 33 | African American | Non hispanic | <1 | 15 | 1 | 1 | Pred 40 mg; HCQ; | ND |
| S-121 | F | 20 | White-Hispanic | Hispanic | N/A | 4 | 0 | 0 | None | ND |
| S-124 | F | 32 | White-Hispanic | Hispanic | N/A | 16 | 0 | 1 | Pred 20 mg; HCQ | ND |
| S-128 | F | 35 | Asian | Non hispanic | 2 | 6 | 0 | 0 | Pred 20 mg; HCQ; MMF 3000 mg | ND |
| S-130 | F | 51 | White-Hispanic | Hispanic | 28 | 0 | 1 | 0 | None | ND |
| S-134 | F | 29 | Caucasian | Non hispanic | 7 | 4 | 1 | 0 | Pred 3 mg; HCQ; MMF 360 mg | ND |
| S-135 | F | 63 | Caucasian | Non hispanic | 11 | 2 | 0 | 0 | HCQ; MMF 1000 mg | ND |
| S-138 | F | 61 | AA | Non hispanic | 36 | 2 | 1 | 0 | HCQ | IV |
| S-139 | F | 22 | Caucasian | Non hispanic | 10 | 6 | 1 | 0 | MMF 2000 mg | ND |
| S-140 | F | 29 | Asian | Non hispanic | 11 | 0 | 1 | 0 | HCQ | IV/V |
| S-141 | F | 38 | Caucasian | Non hispanic | <1 | 6 | 0 | 0 | HCQ | ND |
| S-142 | F | 57 | Black-Hispanic | Hispanic | 16 | 2 | 0 | 0 | HCQ | ND |
| S-144 | F | 48 | Caucasian | Non hispanic | 30 | 2 | 0 | 0 | Pred 5 mg; HCQ | ND |
| S-145 | F | 51 | Asian | Non hispanic | 19 | 3 | 0 | 0 | Pred 5 mg; MMF 3000 mg | ND |
| S-147 | F | 44 | Hispanic white | Hispanic | 13 | 13 | 1 | 1 | MMF 3000 mg | III |
| S-150 | F | 51 | Hispanic white | Hispanic | <<1 | 2 | 0 | 0 | Pred 10 mg; HCQ | ND |

N/A, not available; ND, not determined; AA, African-American; Medications daily dose listed; Pred, prednisone; Meth, methylprednisolone; HCQ, hydroxychloroquin 200-400 mg; MMF, mycophenolate mofitil; MTX, methotrexate weekly; Bel, belimumab.

TABLE 7b

| Temple University Cohort | | | | | | | |
|---|---|---|---|---|---|---|---|
| Temple University Patient ID | Gender | Age | Ethnicity | | SLEDAI score | Renal involvement at time of collection | Renal biopsy (WHO Class) |
| T-106 | F | 20 | AA | Non-Hispanic | 0 | 0 | II |
| T-113 | M | 35 | AA | Non-Hispanic | 19 | 1 | III/V |
| T-107 | F | 22 | Caucasian | Non-Hispanic | 10 | 0 | ND |
| T-108 | F | 45 | AA | Non-Hispanic | 9 | 1 | ND |
| T-119 | M | 29 | Caucasian | Non-Hispanic | 12 | 1 | ND |
| T-123 | F | 23 | AA | Non-Hispanic | 9 | 1 | ND |
| T-124 | F | 35 | AA | Non-Hispanic | 0 | 0 | ND |
| T-125 | F | 34 | Hispanic/Other | Hispanic | 18 | 1 | N/A |
| T-131 | F | 47 | AA | Non-Hispanic | 2 | 0 | ND |
| T-132 | F | 42 | AA | Non-Hispanic | 10 | 1 | III |
| T-133 | F | 25 | AA | Non-Hispanic | 16 | 1 | III |
| T-135 | F | 44 | Hispanic/White | Hispanic | 2 | 0 | ND |
| T-128 | F | 27 | AA | Non-Hispanic | 0 | 0 | III/V |
| T-136 | F | 52 | AA | Non-Hispanic | 3 | 0 | ND |
| T-140 | F | 39 | Hispanic/White | Hispanic | 2 | 1 | V |
| T-141 | F | 38 | AA | Non-Hispanic | 0 | 0 | ND |
| T-146 | F | 53 | AA | Non-Hispanic | 2 | 0 | ND |
| T-162 | F | 61 | AA | Non-Hispanic | 2 | 1 | ND |
| T-150 | F | 53 | AA | Non-Hispanic | 2 | 0 | ND |
| T-169 | F | 56 | Caucasian | Non-Hispanic | 10 | 0 | ND |
| T-178 | F | 33 | AA | Non-Hispanic | 9 | 1 | IV |
| T-171 | M | 24 | Hispanic/Other | Hispanic | 10 | 1 | III |
| T-155 | F | 28 | AA | Non-Hispanic | 14 | 1 | II |
| T-131 | F | 47 | AA | Non-Hispanic | 0 | 0 | ND |
| T-150 | F | 54 | AA | Non-Hispanic | 0 | 0 | ND |

TABLE 7b-continued

Temple University Cohort

| Temple University Patient ID | Gender | Age | Ethnicity | | SLEDAI score | Renal involvement at time of collection | Renal biopsy (WHO Class) |
|---|---|---|---|---|---|---|---|
| T-121 | F | 23 | Hispanic/Other | Hispanic | 9 | 0 | ND |
| T-127 | F | 21 | Asian/Pacific Islndr | Non-Hispanic | 2 | 0 | ND |

AA, African-American

TABLE 7c

Ohio State University Cohort

| Ohio State University Patient ID | Gender | Age | Ethnicity | | UPCR | Renal involvement at time of collection | Renal biopsy (WHO Class) |
|---|---|---|---|---|---|---|---|
| OB-181 | F | 30 | Caucasian | Non-Hispanic | 3.177 | 1 | III |
| OB-212 | F | 39 | Caucasian | Non-Hispanic | 0.589 | 1 | III |
| OB-213 | F | 27 | Caucasian | Non-Hispanic | 1.223 | 1 | IV |
| OB-230 | F | 32 | Caucasian | Non-Hispanic | 8.739 | 1 | IV |
| OB-235 | F | 29 | Caucasian | Non-Hispanic | 3.097 | 1 | III |
| OB-280 | F | 44 | Caucasian | Non-Hispanic | 1.416 | 1 | IV |
| OB-283 | F | 31 | Caucasian | Non-Hispanic | 6.141 | 1 | III |
| OB-241 | F | 42 | Caucasian | Non-Hispanic | N/A | 1 | V |
| OB-253 | F | 40 | Caucasian | Non-Hispanic | 2.387 | 1 | V |
| OB260 | F | 51 | Caucasian | Non-Hispanic | 0.312 | 1 | V |
| OB-275 | F | 23 | Caucasian | Non-Hispanic | 1.033 | 1 | V |
| OB-339 | F | 38 | Caucasian | Non-Hispanic | N/A | 1 | IV |
| OB-340 | M | 25 | Caucasian | Non-Hispanic | N/A | 1 | IV |
| OB-344 | M | 19 | Caucasian | Non-Hispanic | 3.062 | 1 | IV |
| OB-435 | F | 25 | Caucasian | Non-Hispanic | 3.80 | 1 | III + V |
| OB-458 | F | 32 | Caucasian | Non-Hispanic | 3.48 | 1 | IV |
| OB-491 | F | 31 | Caucasian | Non-Hispanic | 0.81 | 1 | IV |
| OB-498 | F | 21 | Caucasian | Non-Hispanic | 3.00 | 1 | IV |
| OB-202 | M | 50 | Caucasian | Non-Hispanic | N/A | 1 | MGN |
| OB-211 | M | 47 | Caucasian | Non-Hispanic | N/A | 1 | MGN |
| OB-232 | M | 57 | Caucasian | Non-Hispanic | N/A | 1 | MGN |
| OB-266 | M | 36 | Caucasian | Non-Hispanic | N/A | 1 | MGN |
| OB-336 | F | 58 | Caucasian | Non-Hispanic | N/A | 1 | MGN |
| OB-371 | F | 26 | Caucasian | Non-Hispanic | N/A | 1 | MGN |

UPCR, urinary protein creatinine ratio; MGN, primary membranous glomerulonephritis Although individuals varied greatly, 11/61 (18%) were in clinical remission and their Chao1 estimates of alpha richness diversity in their microbiota were indistinguishable from the HC (P=0.74, NS). Notably, three of these 11 patients in remission were not receiving medications at time of sampling, while an additional five were receiving only an oral antimalarial agent, hydroxychloroquine, suggesting that gut dysbioses may be uncommon in the absence of Lupus disease activity. However, when all Lupus patients were considered, overall there was significantly restricted biodiversity within their intestinal microbiota, compared to HCs (P=0.038) (FIG. 2A), reiterating the restricted alpha diversity documented in some other clinical conditions (102). Chao1 estimates of alpha diversity showed a numerical trend toward an inverse correlation with SLEDAI score (P=0.08). When patients were dichotomized based on disease activity, those with high disease activity (SLEDAI>7) had pronounced restrictions of their microbiota diversity compared to than HC (P=0.003) (FIG. 2).

The human gut microbiome is dominated by four bacterial phyla: Firmicutes, Bacteroidetes, Actinobacteria and Proteobacteria, with estimates of tens of thousands of species, and countless strains, involved in complex dynamic relationships within gut communities (110). To visualize community variation, the inventors performed principal coordinates analyses (PCoA) that confirmed that the taxonomic distribution within SLE patients was significantly different than in HC (P=0.02) (FIG. 2B). Notably, beta diversity analyses showed that the community within a healthy subject was more closely related to communities in other healthy controls (HC), while most Lupus patients had a wider distribution of phylogenetic diversity. In fact, microbial communities in Lupus affected individuals were also generally quite dissimilar from one another (FIG. 2B).

By PCoA the variability of the communities in HC were significantly different from the subset of SLE patients with low disease activity, while there was even more pronounced divergence with the patients with high disease activity (P=0.002) (FIG. 2C). As mentioned herein, not all Lupus patients had evidence of gut microbial imbalances, and there was overlap with the HC subjects (FIG. 2B), that included several patients in clinical remission who were not receiving immunosuppressive medication. Disease-associated dysbiosis also did not correlate with disease duration (data not shown).

SLE patients displayed a mean five-fold over-abundance of *Ruminococcus gnavus* (RG), an obligate anaerobic Gram-positive species recently reassigned to the *Blautia* genus within the Lachnospiraceae family, (range 0.00-10.79%, mean+/−SD 1.348%+/−2.01) compared to HC (0.00-1.27%, 0.25%+/−0.39 P=0.01) Indeed, SLE patients with low disease activity had minor over-representation compared to healthy subjects, while patients with high disease activity generally had even greater RG abundance (P=0.006) (Tables 5 and 8). In libraries from individual SLE patients, there were variations within the RG-assigned 16S rRNA gene sequences that identify OTU (Table 9), suggesting that these RG were unlikely to reflect the same type of single strain blooms documented for *Prevotella copri* in early onset rheumatoid arthritis (111).

TABLE 8

Univariate analysis of taxa abundance in fecal samples.

| | Taxonomic level | Taxonomy | Healthy | SLEDAI$^{low}$ | SLEDAI$^{high}$ | p value |
|---|---|---|---|---|---|---|
| 1 | Phylum | Actinobacteria | 0.035717396 | 0.068958138 | 0.032634995 | 0.991079785 |
| 2 | Phylum | Proteobacteria | 0.048216548 | 0.034387067 | 0.033770207 | 0.621436085 |
| 3 | Phylum | Firmicutes | 0.518405301 | 0.430966291 | 0.564711534 | 0.115049598 |
| 4 | Phylum | Verrucomicrobia | 0.007566190 | 0.026864292 | 0.010661603 | 0.593552369 |
| 5 | Phylum | Bacteroidetes | 0.361764221 | 0.430770137 | 0.341292736 | 0.529170188 |
| 6 | Class | Erysipelotrichi | 0.016873403 | 0.014351925 | 0.059152401 | 0.119649258 |
| 7 | Class | Actinobacteria | 0.032373056 | 0.065480881 | 0.031255527 | 0.933439498 |
| 8 | Class | Betaproteobacteria | 0.013074438 | 0.010052067 | 0.016736072 | 0.785015334 |
| 9 | Class | Clostridia | 0.493056628 | 0.386991444 | 0.488503529 | 0.096231861 |
| 10 | Class | Gammaproteobacteria | 0.031612832 | 0.018732714 | 0.013495157 | 0.964620853 |
| 11 | Class | Bacilli | 0.008475270 | 0.029622922 | 0.017026344 | 0.657837302 |
| 12 | Class | Verrucomicrobiae | 0.007462018 | 0.026864292 | 0.010661603 | 0.640519718 |
| 13 | Class | Bacteroidia | 0.358826347 | 0.430768765 | 0.341292736 | 0.511340284 |
| 14 | Order | Erysipelotrichales | 0.016873403 | 0.014351925 | 0.059152401 | 0.119649258 |
| 15 | Order | Bifidobacteriales | 0.031413660 | 0.053753821 | 0.031040212 | 0.826017318 |
| 16 | Order | Burkholderiales | 0.013021331 | 0.010050107 | 0.016736072 | 0.772465708 |
| 17 | Order | Clostridiales | 0.492772644 | 0.386927589 | 0.488492552 | 0.096231861 |
| 18 | Order | Lactobacillales | 0.006753619 | 0.028453582 | 0.016099213 | 0.530198073 |
| 19 | Order | Verrucomicrobiales | 0.007462018 | 0.026864292 | 0.010661603 | 0.640519718 |
| 20 | Order | Bacteroidales | 0.358826347 | 0.430768765 | 0.341292736 | 0.511340284 |
| 21 | Family | Erysipelotrichaceae | 0.016873403 | 0.014351925 | 0.059152401 | 0.119649258 |
| 22 | Family | Veillonellaceae | 0.016772782 | 0.034076500 | 0.122675942 | 0.009294467 |
| 23 | Family | Bifidobacteriaceae | 0.031413660 | 0.053753821 | 0.031040212 | 0.826017318 |
| 24 | Family | Alcaligenaceae | 0.012636230 | 0.009251639 | 0.011008572 | 0.773736495 |
| 25 | Family | Ruminococcaceae | 0.265069818 | 0.116767436 | 0.151112522 | 0.019087763 |
| 26 | Family | Prevotellaceae | 0.006148407 | 0.046227323 | 0.061106187 | 0.376133035 |
| 27 | Family | Rikenellaceae | 0.052223569 | 0.035793813 | 0.022141326 | 0.132824814 |
| 28 | Family | Porphyromonadaceae | 0.006973221 | 0.014288711 | 0.006636270 | 0.304545083 |
| 29 | Family | Streptococcaceae | 0.004077237 | 0.014259101 | 0.010343500 | 0.221657770 |
| 30 | Family | Clostridiaceae | 0.017224895 | 0.020579758 | 0.019318824 | 0.654005868 |
| 31 | Family | Verrucomicrobiaceae | 0.007462018 | 0.026864292 | 0.010661603 | 0.640519718 |
| 32 | Family | Lachnospiraceae | 0.130642477 | 0.175832855 | 0.158744130 | 0.281811600 |
| 33 | Family | Bacteroidaceae | 0.252717061 | 0.308497194 | 0.199606056 | 0.372940290 |
| 34 | Genus | *Megasphaera* | 0.003878194 | 0.009520792 | 0.063210082 | 0.263016328 |
| 35 | Genus | *Dialister* | 0.006198509 | 0.011513283 | 0.015272701 | 0.727247802 |
| 36 | Genus | *Bifidobacterium* | 0.031405502 | 0.053726698 | 0.031016735 | 0.826017318 |
| 37 | Genus | *Sutterella* | 0.012636230 | 0.009251639 | 0.011008572 | 0.773736495 |
| 38 | Genus | *Ruminococcus* | 0.099154183 | 0.044115765 | 0.054964326 | 0.127977576 |
| 39 | Genus | *Prevotella* | 0.006148407 | 0.046227323 | 0.061106187 | 0.376133035 |
| 40 | Genus | *Blautia* | 0.021683007 | 0.040953525 | 0.035914227 | 0.057461524 |
| 41 | Genus | *Dorea* | 0.011833821 | 0.014249426 | 0.009427467 | 0.840222727 |
| 42 | Genus | *Streptococcus* | 0.004005869 | 0.013608671 | 0.010316347 | 0.239522630 |
| 43 | Genus | *Akkermansia* | 0.007462018 | 0.026864292 | 0.010661603 | 0.640519718 |
| 44 | Genus | *Coprococcus* | 0.021226059 | 0.029813537 | 0.017080880 | 0.520847758 |
| 45 | Genus | [*Ruminococcus*] | 0.006408245 | 0.017568628 | 0.031536403 | 0.012886993 |
| 46 | Genus | *Bacteroides* | 0.252717061 | 0.308497194 | 0.199606056 | 0.372940290 |
| 47 | Species | *B. adolescentis* | 0.014926584 | 0.022310306 | 0.019180464 | 0.442513917 |
| 48 | Species | *P. copri* | 0.005833339 | 0.046030495 | 0.048685732 | 0.589221697 |
| 49 | Species | *A. muciniphila* | 0.007462018 | 0.026864292 | 0.010661603 | 0.640519718 |
| 50 | Species | *R. gnavus* | 0.002319268 | 0.011872029 | 0.021133120 | 0.005968172 |
| 51 | Species | *B. uniformis* | 0.019469577 | 0.008726573 | 0.003482228 | 0.016109354 |
| 52 | Species | *B. fragilis* | 0.010538618 | 0.024114905 | 0.021999473 | 0.077351980 |

Lupus is associated altered dynamic relationships between species.

As microbiome communities are complex, the inventors looked for evidence of coordinated shifts in the representation of individual species, and interrogation of individual Lupus microbiome communities provided circumstantial evidence that certain commensal species may be in dynamic reciprocal relationships with each other (Table 10). Specifically, the inventors found that RG outgrowths were commonly associated with reciprocal concurrent reductions of the *Bacteroides uniformis* species (P<0.001), with the most sparse levels in those with the highest SLEDAI scores (P=0.016) (Table 9) (112, 113). Similarly, RG expansions also inversely correlated with reduced representation of *Faecalibacterium prausnitzii* (p<0.00002), an anaerobe with putative protective properties and representation is also reported to be reduced in many patients with active inflammatory bowel syndrome (IBD) (114, 115).

TABLE 9

Taxa with reciprocal levels of abundance.

| | F. prausnitzii | R. gnavus. | B. uniformis |
|---|---|---|---|
| All subjects | | | |
| F. prausnitzii | 1.00 | 0.00002 | 0.90 |
| R. gnavus. | −0.47 | 1.00 | 0.02 |
| B. uniformis | −0.01 | −0.26 | 1.00 |
| | F. prausnitzii | R. gnavus | B. uniformis |
| SLE only | | | |
| F. prausnitzii | 1.00 | 0.001 | 0.73 |
| R. gnavus | −0.43 | 1.00 | 0.006 |
| B. uniformis | 0.05 | −0.35 | 1.00 |
| Control only | | | |
| F. prausnitzii | 1.00 | 0.04 | 0.29 |
| R. gnavus | −0.50 | 1.00 | 0.27 |
| B. uniformis | −0.27 | 0.28 | 1.00 |

Analyses of 16S data were performed after CLR normalization.
Numbers above diagonal underlined values are p-values.

Strains differ in immune recognition by Lupus serum antibody responses.

Whereas these microbiome analyses documented an overabundance of RG in active SLE patients, to search for a connection with pathogenesis, the inventors investigated for special host-pathobiont relationships within the immune systems of SLE patients. The inventors first examined whether Lupus circulating antibodies in can recognize the bacterial antigens in mono-cultured extracts of individual RG strains, after electrophoretic separation and immunoblotting. Lupus serum IgG reacted with a small number of protease-sensitive bands that varied in expression in different RG strains (FIG. 3). In contrast, the RG2 strain alone contained a conserved immunodominant repetitive polymeric set of antigenic bands (at ~20-28 kDa), which were resistant to treatment with lysozyme, and to a non-specific endonuclease and Proteinase K (FIG. 3). Transmission electron microscopy studies revealed binding by serum IgG from lupus patients to cultured RG2 cells with staining enhanced in the cell wall in a stranding/filament-like pattern, which is characteristic of lipoglycan expression in gram-positive cocci (115). Taken together, serum IgG of 22.9% of SLE patients in the NYU cross-sectional cohort was highly reactive with the RG CC55_001C strain (here termed *R. gnavus* strain 2, RG2) (Table 10) using a cut-off determined with a serum panel from unaffected individuals.

TABLE 10

Strains of *R. gnavus*.

| Strain designation | Origin |
|---|---|
| CC55_001C | Colonic biopsy |
| VPI C7-9 | Human stool |
| CD1 FAA 3 | Crohn's Disease community 1 - mucosal biopsy |
| 32-6-I 9 D6 FAA AN | Healthy Donor 6 -stool |
| 2/1/58FAA | IBD Patient 58 mucosal biopsy |
| UC2 D5 FAA 1 | Ulcerative colitis community 2 - mucosal biopsy |
| OB21_GAM_25_AN | Obese community 1 - stool |
| WAL 14576 | Finegold lab strain isolate - stool |

Strikingly, levels of host systemic IgG reactivity with the RG2 strain directly correlated with the RG abundance in a fecal sample, based on 16S rDNA gene sequence analyses (P=0.002) (FIG. 4A). However, this association was not found in the unaffected controls, and the inventors found little or no antibody reactivity was found with seven other RG strains (FIG. 3) (Table 10). Furthermore, levels of circulating RG2 strain-reactive IgG-antibodies also directly correlated with SLEDAI score (P=0.02) (FIG. 10), and when Lupus patients were dichotomized into groups based on disease activity the levels of RG2 strain-specific IgG responses were significantly higher in those with SLEDAI scores >7 (P<0.001) (FIG. 4B). This was not evident for the other RG strains. Notably, serum IgA responses to RG2 were also more commonly detected in SLE patients, although these IgA antibodies neither correlated with renal disease nor with IgG antibody levels.

The RG2 strain has the properties of an immune mimic for DNA/chromatin.

Figure 8:
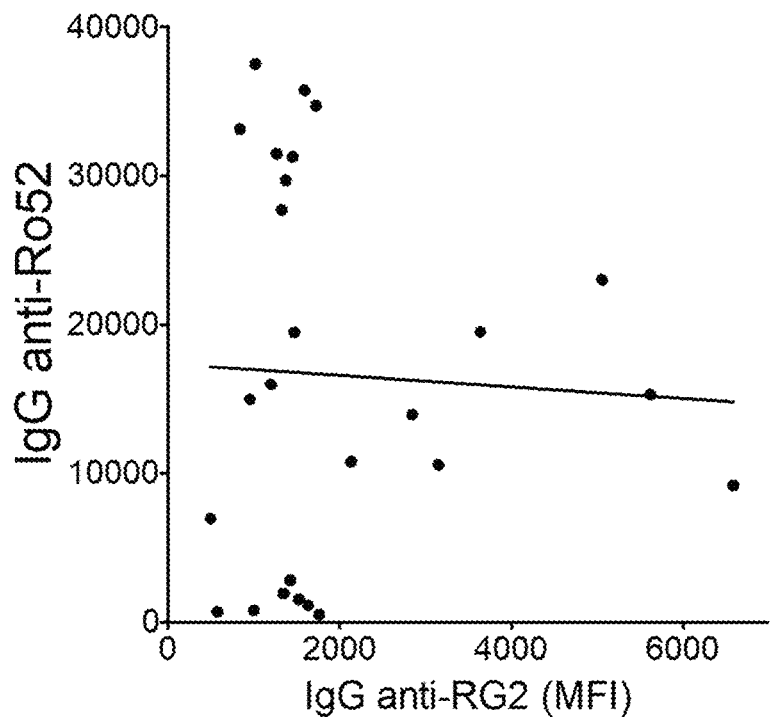
FIG. 8. Levels of serum IgG anti-RG2 do not correlate with IgG anti-Ro (SSA). The former were measured by bead based assay, and the latter by commercial ELISA (INOVA). P=0.82. There is no correlation between IgG anti-RG2 levels and IgG anti-Ro (SSA) levels.
Figure 9A:
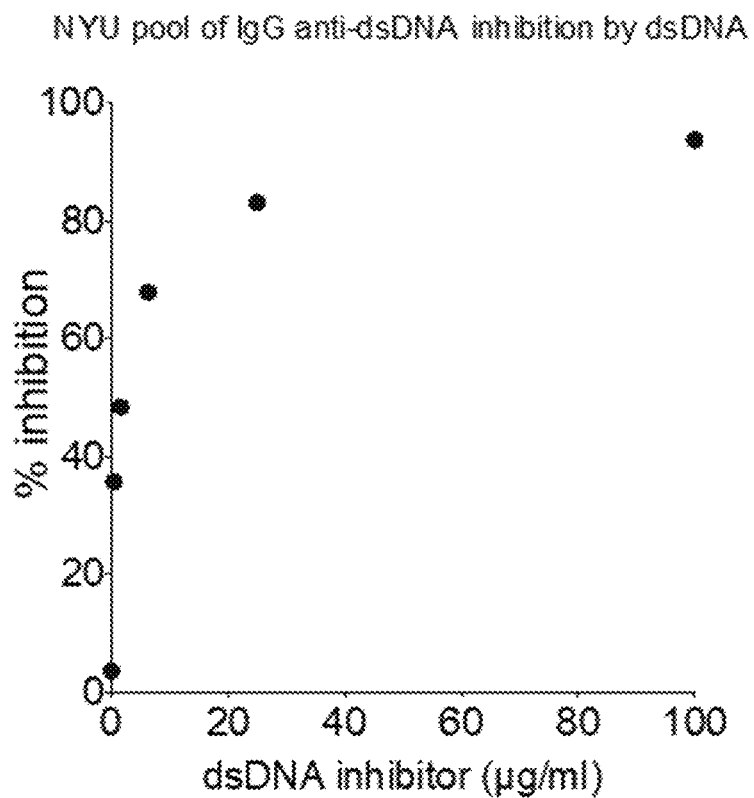
FIGS. 9A-9F. Demonstration of IgG anti-DNA inhibition in different Lupus clinical cohorts. Binding of IgG to dsDNA in an ELISA based assay was inhibited by preincubation, with either defined concentrations of mammalian dsDNA or the RG2 extract, as indicated at bottom.
Figure 9B:
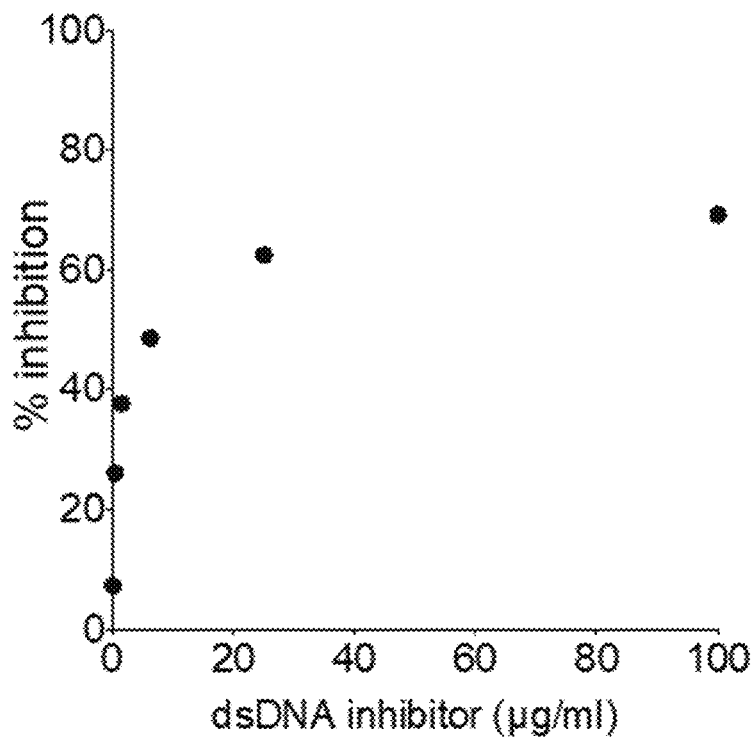
Figure 9C:
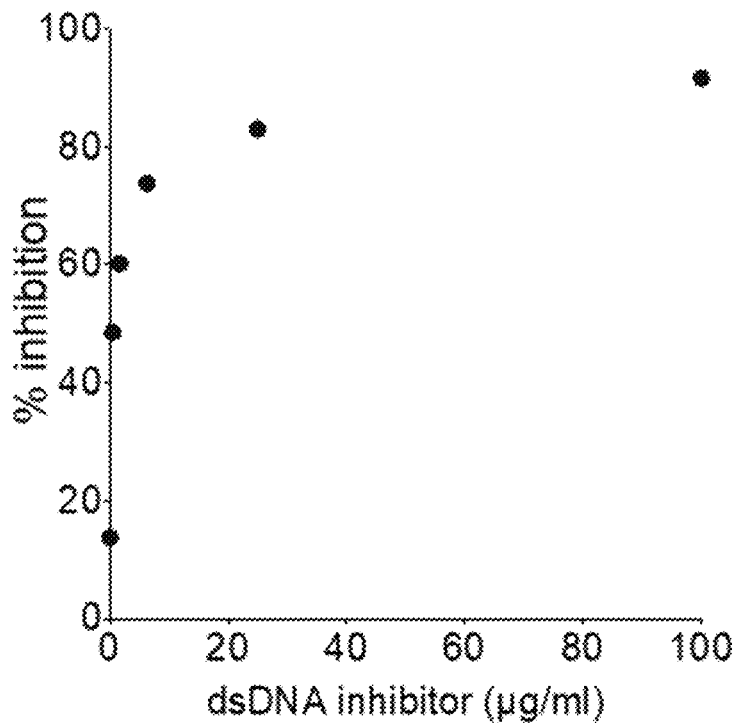
Figure 9D:
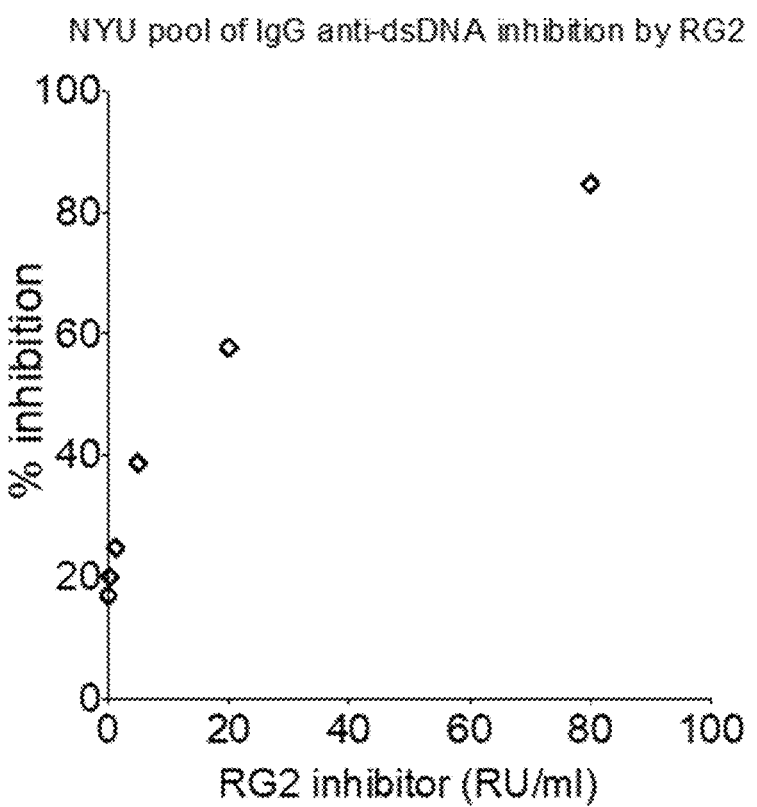
Figure 9E:
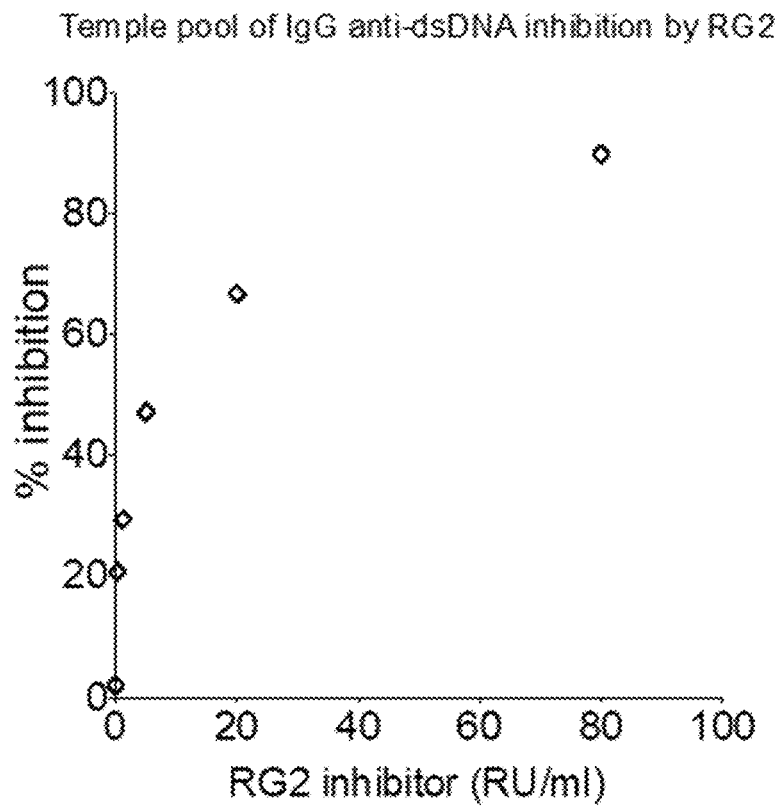
Figure 9F:
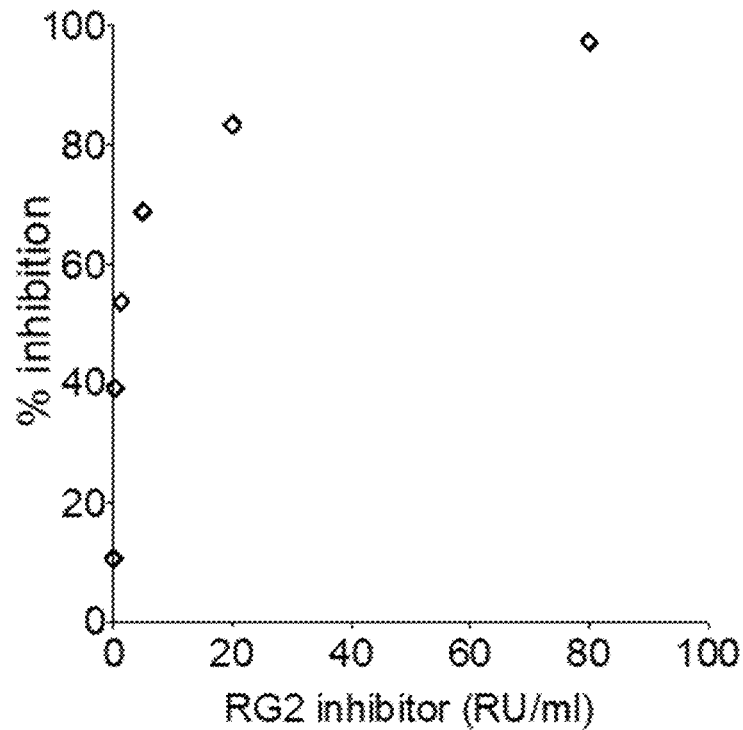

Serum levels of IgG anti-RG2 strain antibodies correlated with IgG anti-chromatin (not shown) and anti-native DNA autoantibodies (P<0.0001) (FIG. 4C) (90, 117). IgG antibodies to RG2 were also significantly positively correlated with IgG reactivity against human glomerular extract (P<0.0001) (FIG. 4D), which is reported to identify the most nephritogenic subset of circulating anti-DNA antibodies (118). In contrast, there was neither an association with other types of Lupus-associated autoantibodies, including IgG anti-Ro (FIG. 8) XX, nor with total IgG levels (not shown).

Antibody response to a RG strain is associated with renal disease.

Relevant to clinical disease state, levels of IgG anti-RG2 antibodies also inversely correlated with serum C3 (P<0.01) (FIG. 4E) and C4 levels (P<0.0064) (FIG. 4F), biomarkers for in vivo activation of the complement cascade implicated in active immune-complex mediated pathogenesis in Lupus nephritis (117, 119, 120). Indeed, in patients with a history of renal involvement, i.e., detected at any time since diagnosis, there was a greater abundance of RG (P=0.04) and of several other taxa, which included two species within the Veillonella family (Table 6). These *Veillona* species were highly correlated with each other (CLR transformed, r=0.89, P<10-16) but less strongly with RG (39% *V. parvula*, 43% *V. dispar*, P<0.005).

An epitope on RG2 represents an immune mimic of mammalian DNA.

Figure 5A:
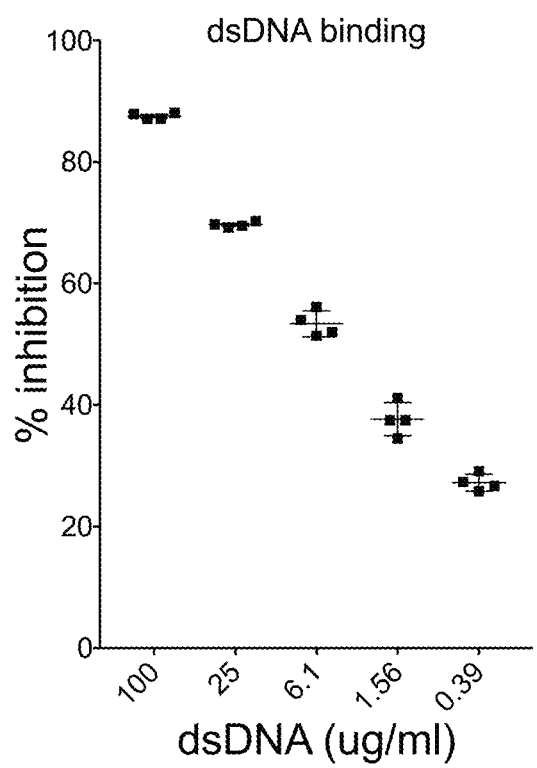
FIGS. 5A-5J. Anti-DNA antibody Inhibition studies underscore the native mammalian DNA-like binding epitope(s) of RG2 despite nuclease treatment. (5A-5D) Inhibition assays were performed with preincubation of diluted serum with the inhibitor in sandwich ELISA, as indicated. (5A) Native mammalian DNA in solution is capable of dose-dependent inhibition of the binding by a representative Lupus serum to immobilized calf thymus DNA on the solid phase. (5B) Nuclease- and proteinase K treated RG2 extract is responsible for dose-dependent inhibition of the binding by a representative Lupus serum to immobilized calf thymus DNA on the solid phase. (5C) Preincubation of representative Lupus sera with soluble RG2 inhibits binding of IgG to the RG2 on the solid phase of the well. (5D) Preincubation of the Lupus serum with soluble native mammalian DNA has little inhibitory capacity for the binding of IgG to treated RG2 on a solid phase. (5E-5J) Fine binding specificity of Lupus serum IgG with a circular native DNA-containing organelle in Crithidia lucillae. (5E) A positive control serum, provided by the manufacturer, is associated with reactivity with the *Crithidia lucillae* kinetoplast (indicated with white arrows) and the nucleus. A representative Lupus serum IgG is reactive (5F) at 1:40 final dilution, and (5G) at 1:100 final dilution, respectively. (5H) Serum from an unaffected subject is non-reactive. (5I) After preincubation of mammalian native DNA (100 μg/uL, final concentration) with a Lupus serum at 1:40 final dilution. (5J) After preincubation of RG2 extract (25 RU/mL) with a Lupus serum at 1:40 final dilution. S-047, a patient with active LN, was the source of the representative serum.
Figure 5B:
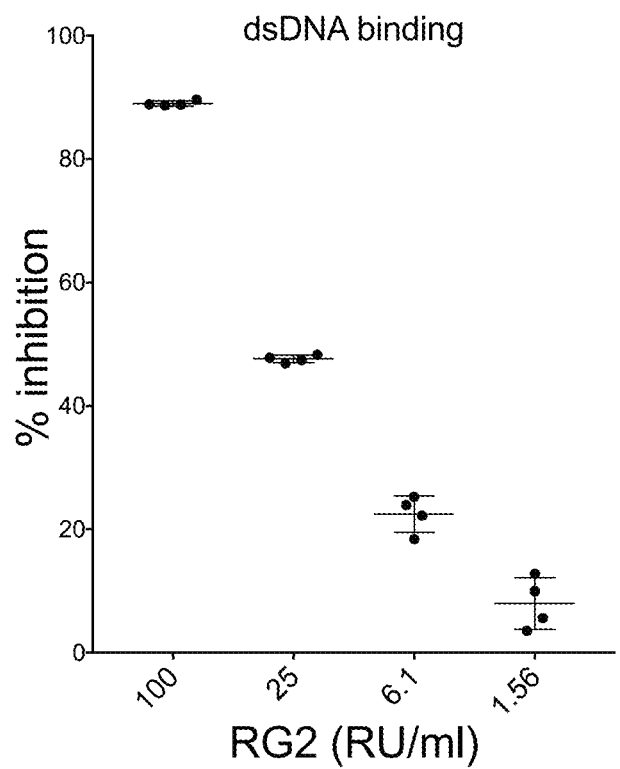
Figure 5C:
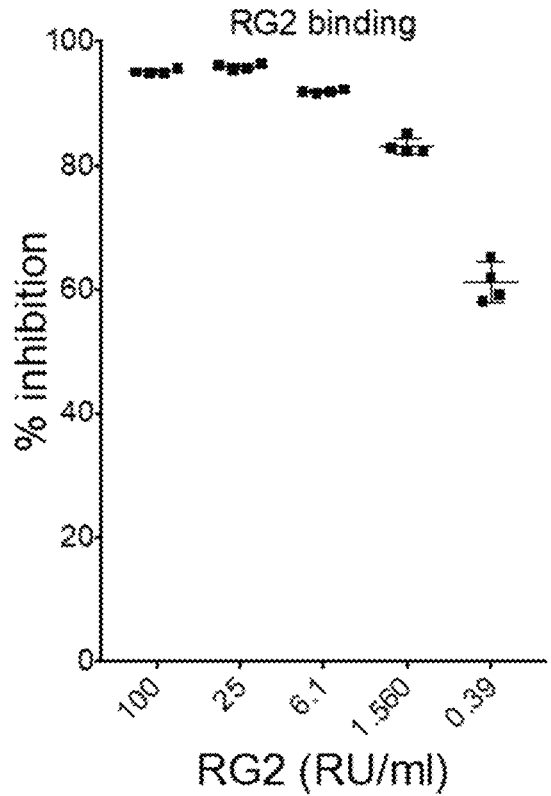
Figure 5D:
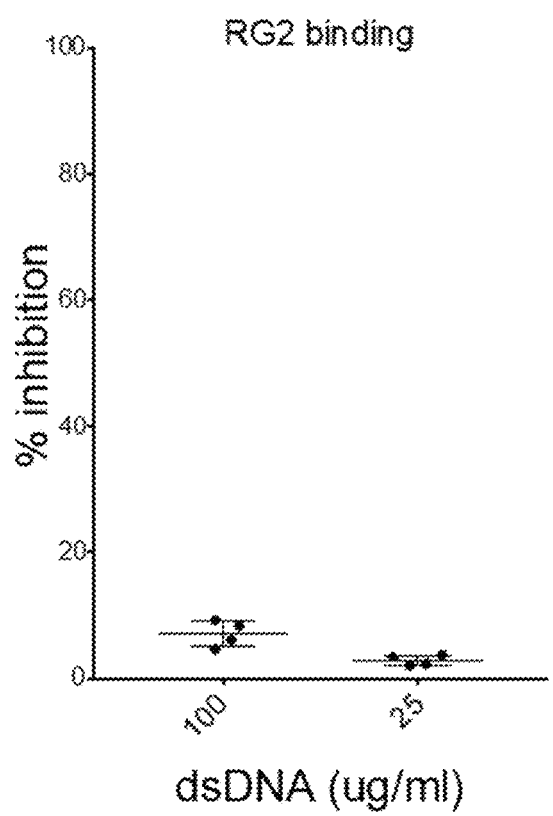
Figure 5E:
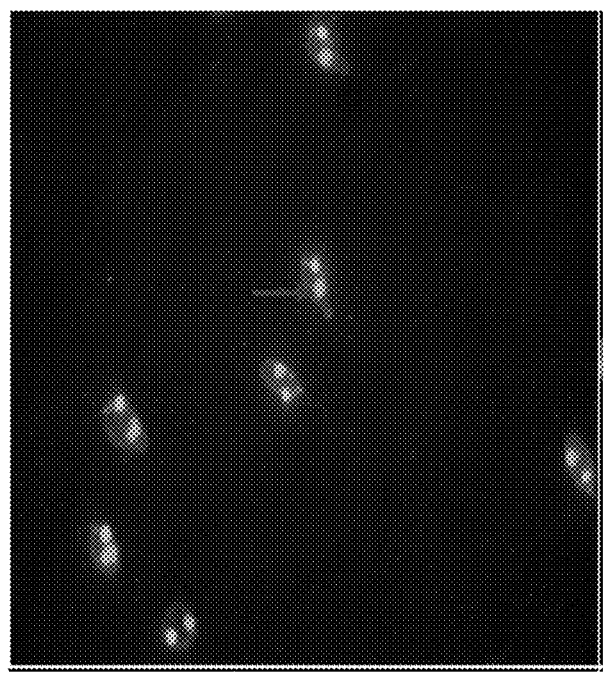
Figure 5F:
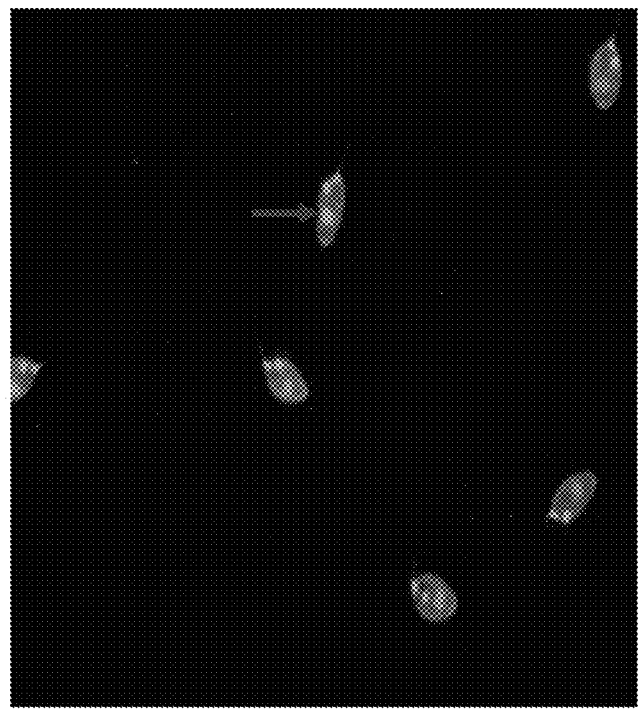
Figure 5G:
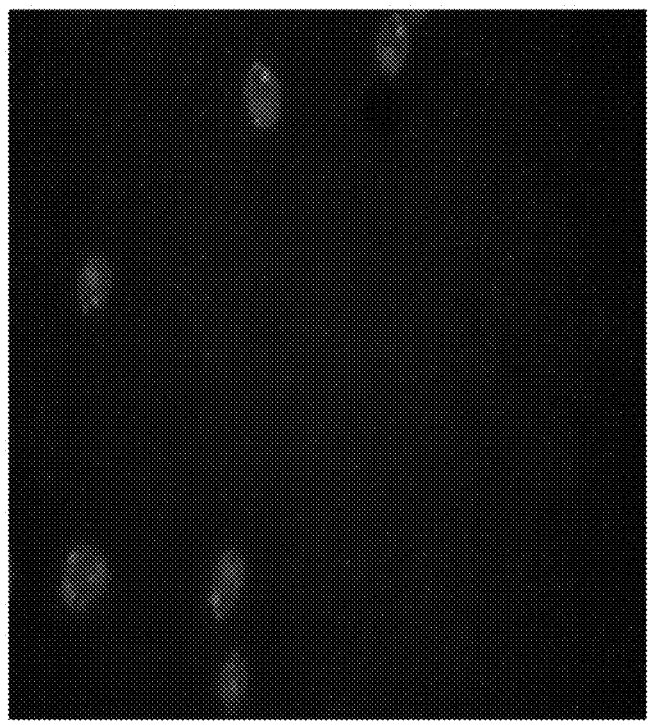
Figure 5H:
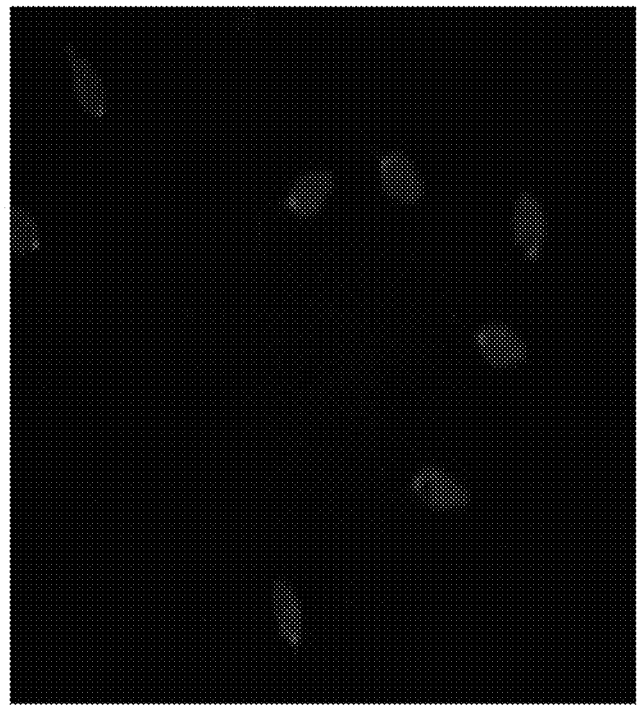
Figure 5I:
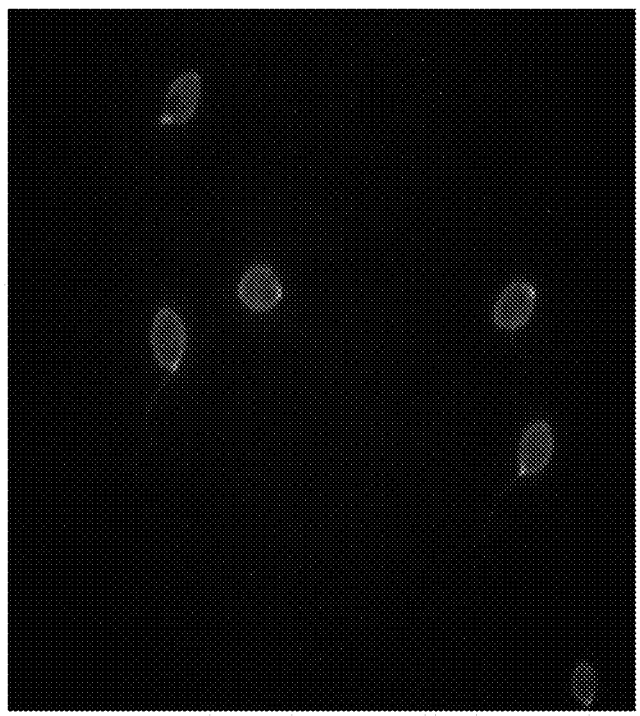
Figure 5J:
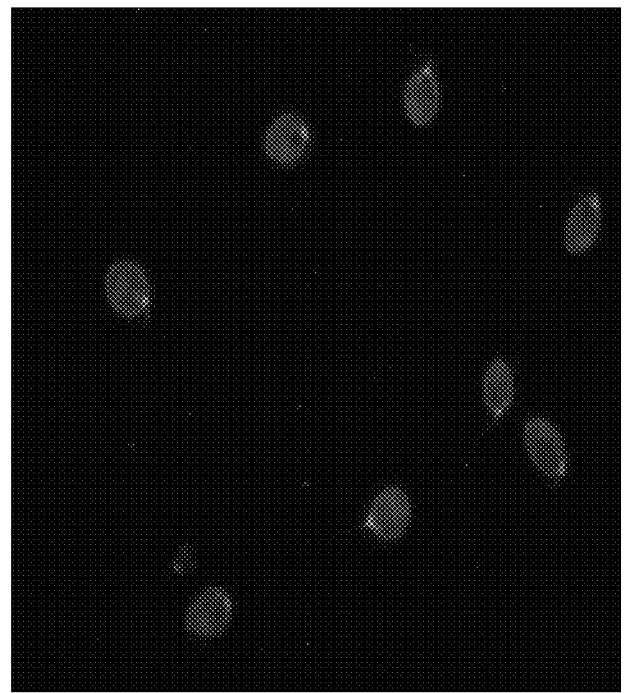

To evaluate for relationships of these antigens in the Lupus responses, the inventors performed immunoassays that evaluated the capacity of native DNA and RG2 extract to inhibit Lupus serum IgG binding to native mammalian DNA. Strikingly, both non-treated RG2 and protease/nuclease-treated RG2 extracts displayed dose-dependent inhibition of the binding of Lupus serum IgG to native DNA (FIG. 5A). RG2 displayed a high level (~90% maximal) inhibition of native mammalian DNA binding (FIG. 5B), which was nearly as efficient of an inhibitor as soluble native DNA itself. In side-by-side assays, soluble RG2 extract was an efficient inhibitor of the binding of Lupus serum IgG to immobilized treated RG2 extract (FIG. 5C). However, native DNA was not a good inhibitor of the IgG binding to native mammalian DNA (FIG. 5D), which suggests that RG2 also possesses epitopes that do not resemble DNA.

To further confirm the relevance of RG2 epitopes with anti-nuclear antibody responses, the inventors assessed the effect on IgG antibody reactivity with *Crithidia lucillae*, a protozoan with a kinetoplast organelle that contains interlocking circular native DNA molecules, which is used in an accepted standard assay for detection of antibodies specific for native double stranded DNA (121). Adapting the standard immunofluorescence assay (FIGS. 6E-6J), just as native mammalian DNA had the capacity to inhibit this antibody interaction (FIG. 6I), so did preincubation of Lupus serum IgG with RG2 extract (FIG. 6J). In addition, an extract of a different RG strain (i.e., RG1) (Table 10) inhibited neither Lupus IgG-binding to dsDNA nor to RG2, confirming this glycan-associated epitope is strain-restricted. Furthermore, SLE patients with active disease commonly display both anti-RG2 antibodies cross-reactive with native DNA and there are also RG2-reactive IgG antibodies that are not inhibitable by mammalian DNA molecules (FIG. 6D). These findings provide evidence that the purified RG2 preparation displays epitope(s) recognized by native DNA-specific autoantibodies, and also a subset of antibodies that did not recognize DNA. Without wishing to be bound by theory, it is suggested that in a SLE patient, antigenic epitope(s) of RG2 often serve as an immune mimic of native mammalian DNA.

Independent cohorts confirm association with anti-RG2 responses and Lupus nephritis.

Figure 6A:
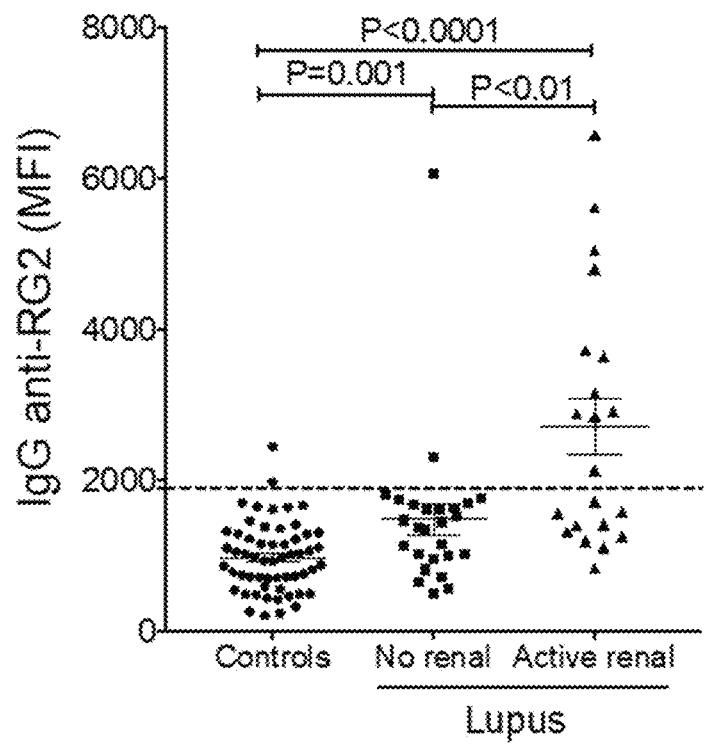
FIGS. 6A-6C. Elevated IgG anti-RG2 antibodies associated with active Lupus nephritis. (6A) Results from individuals in a NYU cohort are shown, with comparisons to unaffected controls, which included healthy controls (HC) with microbiome data, 15 additional healthy individuals, 13 with psoriatic arthritis, and 12 with osteoarthritis. (6B) Results from individuals in the Temple University cohort with 16 Lupus patients without evidence of renal (i.e., non-renal), and 12 with active LN. (6C) Results from 5 individuals with biopsy proven idiopathic membranous glomerulonephritis (MGN) compared to 17 with biopsy-proven active LN. The IgG anti-RG2 cutoff value of 1898.6 was based on the mean plus 2SD of the control subject sera tested. Significance based on Mann-Whitney test.
Figure 6B:
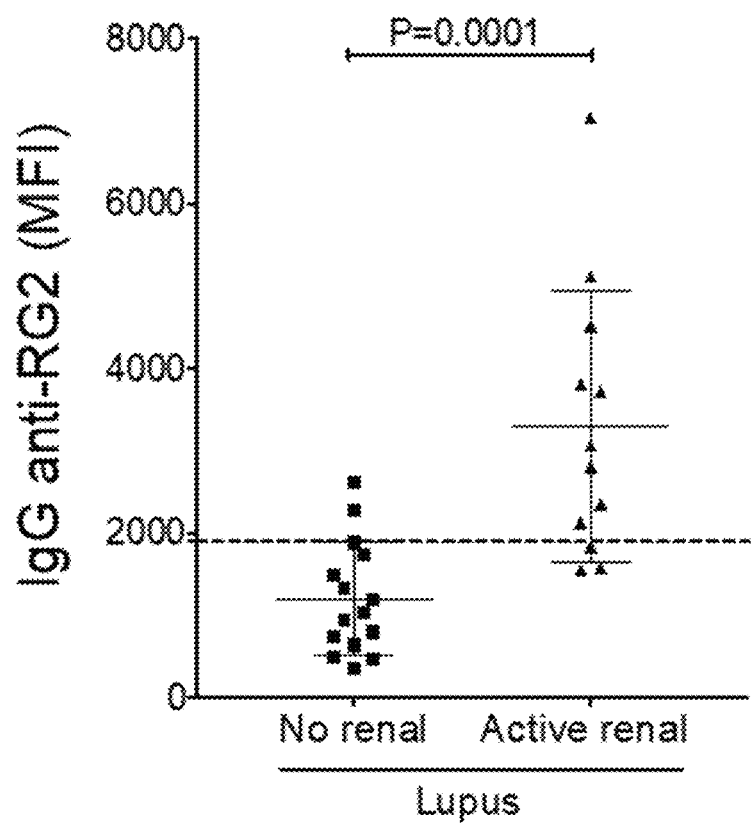

Furthermore, in the discovery NYU cohort, patients with active nephritis at the time of blood sampling (based on activity criteria (108)) had significantly raised levels of IgG anti-RG2 strain-specific antibody responses (FIG. 6A). To confirm this association, serologic surveys were performed in a second independent cohort from Temple University (Table 7), in which 11 of these 27 patients had elevated IgG anti-RG2 antibody reactivity, and of those with active nephritis (based on level of proteinuria and/or biopsy data) 9 of 12 (75%) were positive for this antibody assay (FIG. 6B).

Figure 6C:
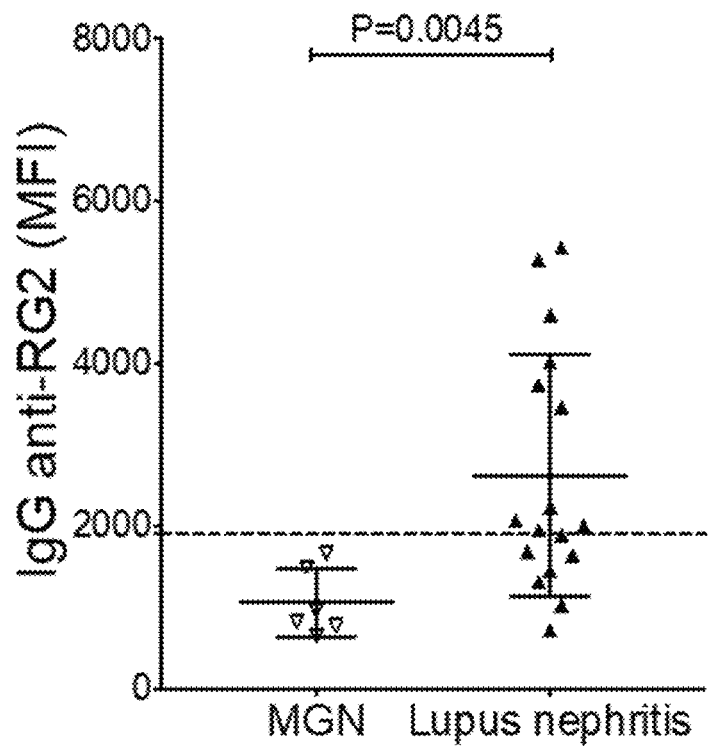
Figure 7A:
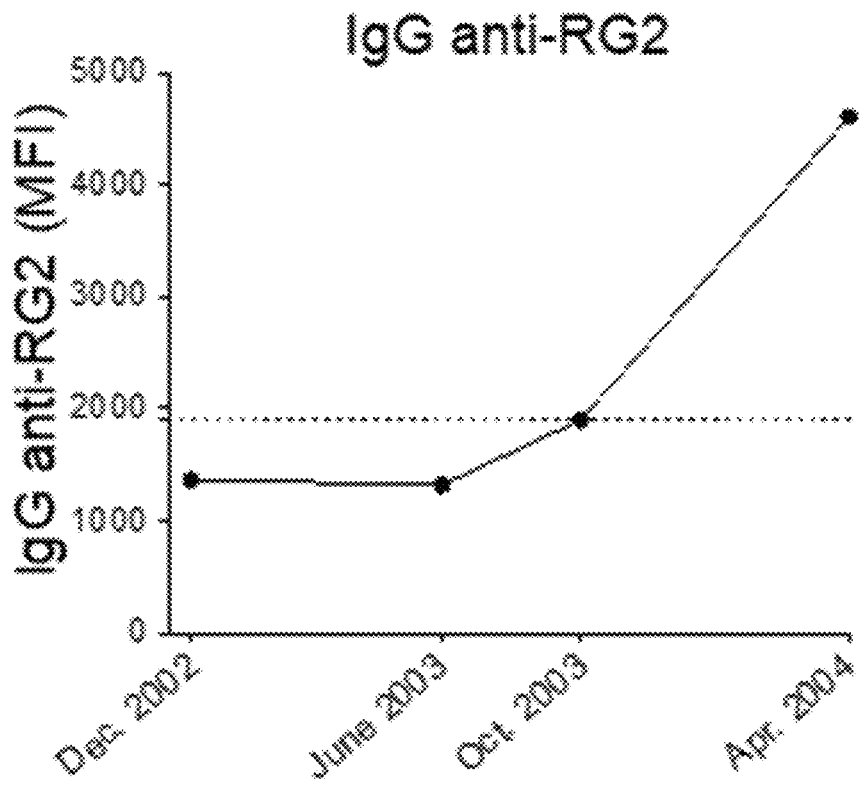
FIGS. 7A-7H. Serum levels overtime in a Lupus patient with worsening disease activity and nephritis. Longitudinal serially serum samples demonstrated that this patient had increasing levels of anti-RG2 strain antibodies (7A)(upper left), concurrent with worsening renal function and increasing proteinuria. IgG antibodies to dsDNA, glomerular extract, chromatin and C1q (7B-7E) increased overtime in parallel (Serum complement (C3 and C4)(7F and 7G), creatinine levels, and 24-hour urinary protein levels were determined by standard clinical assay as part of routine care (7H). Antibody assays were calibrated with dilutions of a pooled standard, and run with control samples from healthy and Lupus-affected individuals.
Figure 7B:
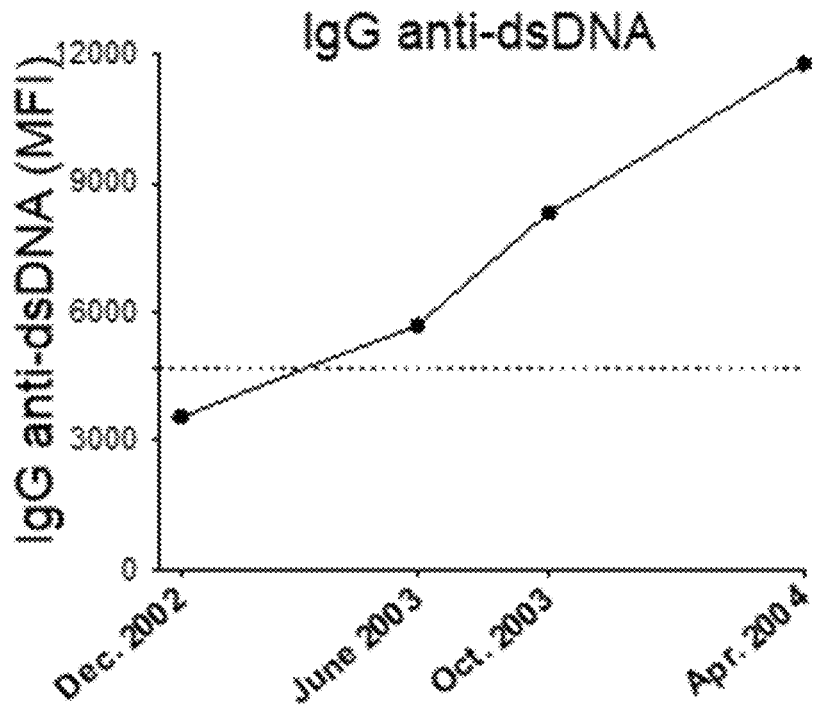
Figure 7C:
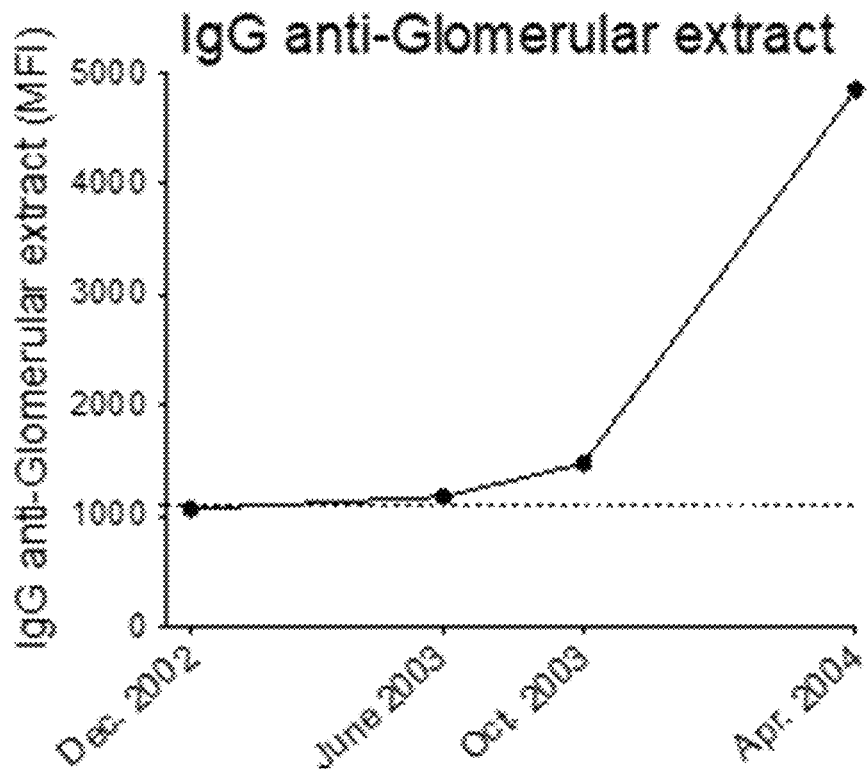
Figure 7D:
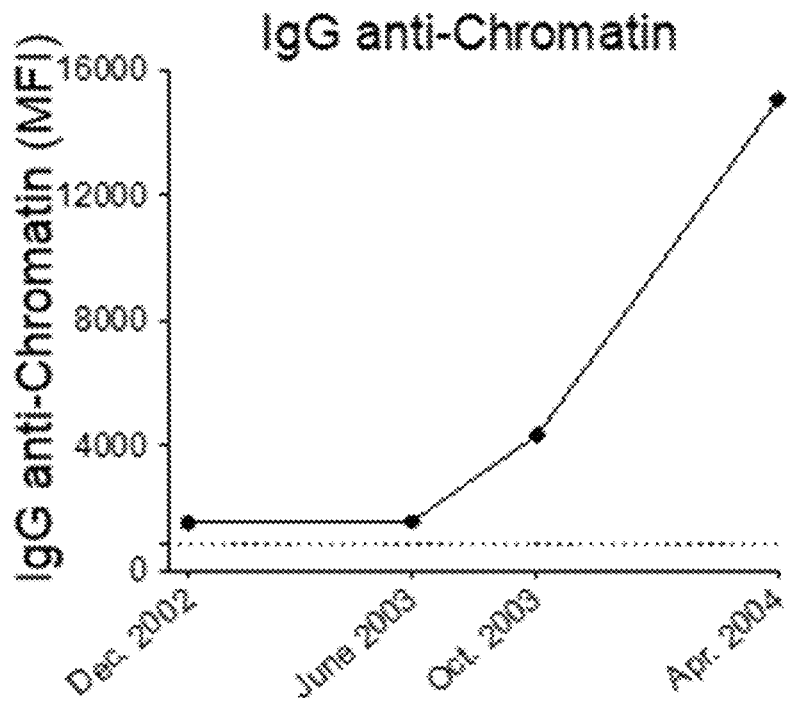
Figure 7E:
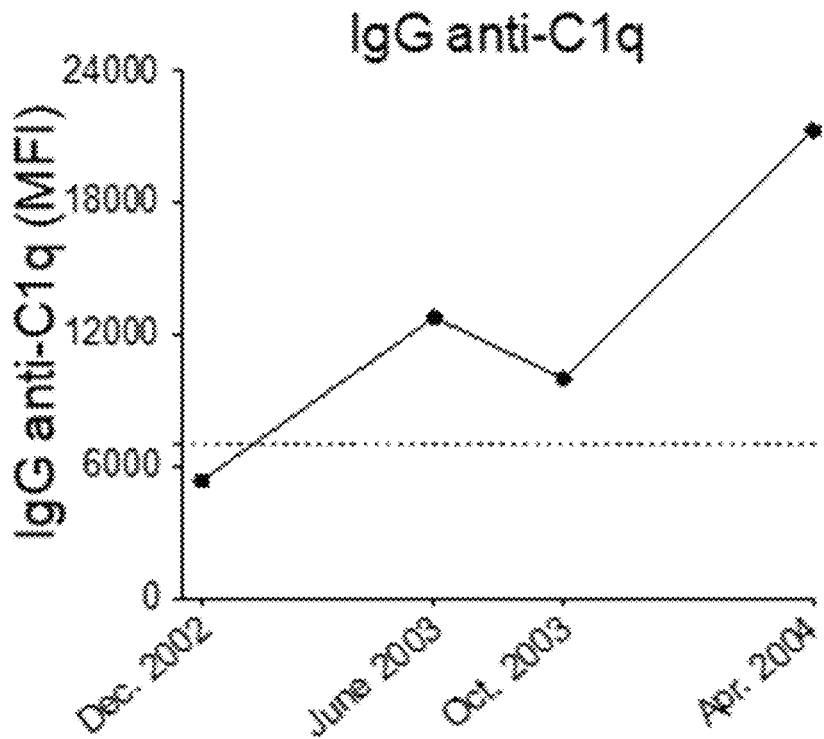
Figure 7F:
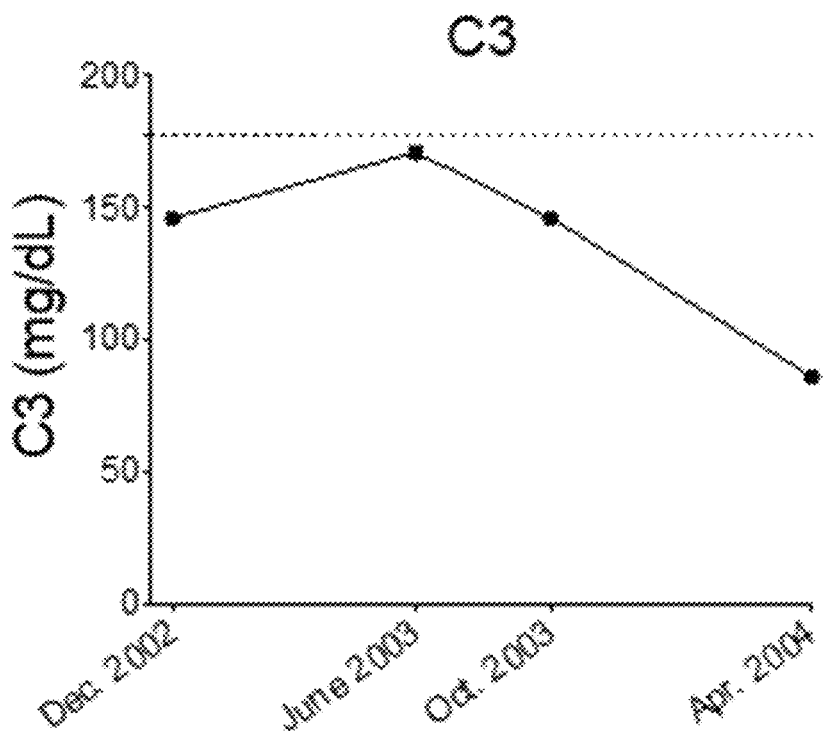
Figure 7G:
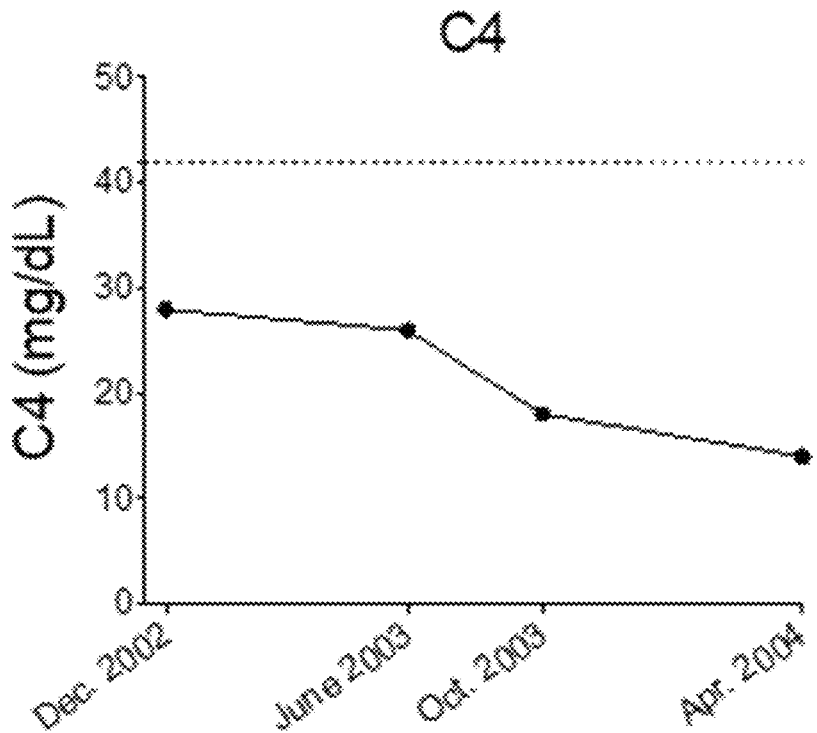
Figure 7H:
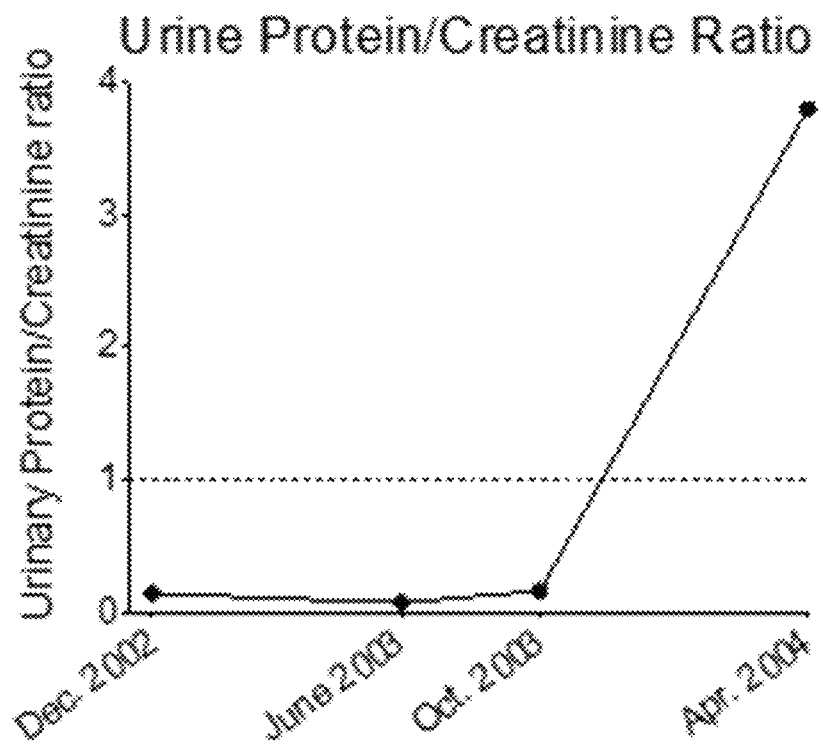

As further confirmation, the inventors also investigated a third cohort from Ohio State University of 17 patients that all had biopsy-based histopathologic characterization of active renal involvement (Table 7). Compared to serum from patients with primary membranous glomerulonephritis, an immune complex mediated condition with otherwise different pathogenesis, the LN patients from the Ohio cohort showed the same elevations of serum IgG anti-RG2 responses (P=0.0025) (FIG. 6C). Notably, renal biopsy data were also available for some patients in the NYU and Temple cohorts (Table 7). Taken together, in three independent cohorts, the inventors documented high IgG anti-RG2 antibody reactivity, with evidence of cross-reactivity with anti-native DNA autoantibodies (FIGS. 9A-9F) in patients with active Lupus glomerular disease due to a range of immunohistopathologic diagnoses; Class III and Class IV proliferative LN, based on ISN/RPS criteria (122) (Table 7). Inhibition studies of pooled sera from each of these three independent geographically separated cohorts were performed. These studies confirmed that in each of these cohorts, Lupus-associated autoimmune IgG anti-native DNA responses are cross-reactive with epitope(s) in the RG2 strain.

SLE is a condition that overwhelmingly affects women, and due to concerns that gut microbiome can vary based on sex alone (123), the inventors initially restricted studies in the discovery cohort to female patients. Yet the confirmatory cohorts included several male patients, including individuals with active Lupus nephritis, which were found to also have elevated levels of serum IgG anti-RG2 antibodies (Table 7, FIG. 6B-6C). With regard to race and ethnicity, raised levels of serum antibody responses to RG2 were found in patients with active LN of diverse race-ethnicity: African-American, Asian, Caucasian, as well as those self-designated as Hispanic-White and Hispanic-Black (Table 7).

Whereas the above-described investigations involved cross-sectional cohorts, to begin to consider the implications for a temporal relationship between immune responses to the RG2 strain and clinical development of LN, the inventors examined longitudinal serum samples from a representative SLE patient. FIGS. 7A-7H XX illustrate disease development in 23-year-old African-American woman with SLE who was first recruited in 2001. In her earliest available serum sample (December 2002), there was no laboratory evidence of LN revealed elevated levels of IgG autoantibodies to chromatin. At follow-up 6 months later (June 2003), the patient's serum showed elevated levels of anti-dsDNA and anti-C1q antibodies, but urine protein to creatinine ratio was <0.5 and therefore LN was deemed not active. Four months later (October 2003), anti-ds DNA and anti-chromatin antibody levels increased further, and the levels of antibodies to glomerular extract and to RG2 increased above that level in unaffected controls, and serum C3 and C4 levels began to decrease. After an additional 6 months (April 2004), the patient's urinary protein to creatinine ratio, a marker of renal function, deteriorated markedly (FIG. 7A-7H). At that time, the IgG anti-RG2, anti-dsDNA, anti-C1q, anti-chromatin antibody levels were greatly increased, and C3 and C4 continued to fall (FIG. 7A-7H). During this period, the patient was treated with advancing regimens of immunosupressive agents (i.e., mycophenolate mofitil and escalating doses of oral prednisone), but the patient did not improve and there were concerns of medical nonadherence. In June 2007, a renal biopsy documented ongoing active diffuse proliferative (Class IV) LN with tubular atrophy and interstitial fibrosis. The patient subsequently progressed to irreversible renal failure that required hemodialysis. This case suggests that, induction of a robust systemic immune response to RG2 can occur much after initial onset of clinical disease, and can be associated with progressive renal disease and clinical deterioration.

Discussion

As Lupus patients display great variation in clinical disease activity and organ system involvement, the inventors hypothesized that if the gut microbiome contributes to pathogenesis, there may be distinctive patterns of altered phylogenetic representation in different patient subsets. The discovery surveys of a cross-sectional urban cohort documented that severity of specific patterns of dysbiosis generally correlated with clinical disease activity. Indeed, higher SLEDAI scores were associated with restrictions in taxonomic diversity. Notably, these studies provide evidence of a possible role of intestinal outgrowths of *Ruminococcus gnavus* (RG), an obligate anaerobic species recently reassigned to the *Blautia* genus within the Lachnospiraceae family in the class Clostridia (42). Whereas RG was a common component with low-level abundance in the gut microbiota of a healthy cohort (HC), Lupus patients had much greater (i.e., >5-fold mean) abundance, and there was a significant direct relationship with Lupus disease severity. There was also a significant direct relationship between Lupus disease severity and the levels of serum IgG antibodies to a cell wall associated non-nucleic acid non-protein lipoglycan-containing antigen of the RG2 strain. In the discovery cohort, and two independent confirmatory Lupus cohorts, the inventors documented that the highest levels of this commensal strain-specific IgG anti-RG2 were in patients with active LN, based on clinical laboratory testing (108) and/or biopsy-proven LN (Table 7), and that Lupus patient IgG-antibody responses to the RG2-associated glycan displayed cross-reactivity with native mammalian DNA. Importantly, in competition ELISA, protease-nuclease-treated RG2 was nearly as efficient of an inhibitor of anti-DNA binding as DNA itself. In preliminary studies, the inventors found that Lupus unaffected siblings can have IgG anti-RG2 responses that are not cross-reactive with DNA, which suggests the RG2 lipoglycan-containing antigen has more than one type of epitope.

In the human gut, members of the Lachnospiraceae family fill a special niche, as they degrade complex polysaccharides into short-chain fatty acids that can be used for energy by the host, and this function cannot be performed by other microrganisms (125). Within this family, the RG species represents an early keystone colonizer of human gut communities in health (126), with common representation in infants (127) and is detectable in up to 90% of adults (128). Yet RG strains are known to vary greatly with regard to their genomic composition, metabolic features, and competitiveness. Indeed, some strains can use the host protective mucous layer as a nutritional source (129) produce Lantibiotic polypeptides that can suppress competing anaerobic species (130). RG colonization can also protect against overgrowths of *C. difficile* responsible for colitis (131) and the development of obesity (132). RG strains have also been ascribed protective anti-inflammatory properties (i.e., induction of regulatory T cells) (133) while murine colonization with other strains reportedly shifts the balance of T cells toward a pro-inflammatory milieu (i.e., IL-17 production) (134, 135).

Herein is the first report of disease-associated colonization that is accompanied by circulating RG-specific antibody responses. The inventors found that RG outgrowths in Lupus were associated with cross-reactive anti-RG2/DNA systemic responses in the absence of signs or symptoms of clinically apparent bowel disease. Without wishing to be bound by theory, it is suggested that the predisposition for the outgrowth of RG pathobiont strains derives from currently poorly understood environmental influences, including perhaps prior antibiotic exposure or perinatal events that disrupt early intestinal colonization. Yet, SLE or IBD involve very different pathophysiologic pathways that are in part likely determined by very different disease-associated genetic profiles that contribute to the very different disease localization and associated innate and adaptive immune responses, and which in fact may also affect taxa representation within their microbiota (140).

In studies such as the ones herein, evidence of an association of disease with specific microbiome patterns predictably raises the question of whether these shifts in microflora truly influence disease activity and specific disease manifestations. Alternatively, it could be that the disease activity is responsible for an altered local intestinal environment that fosters preferential outgrowth of the candidate pathobiont. It should also be acknowledged that the majority of our patients received medication at the time of biosampling, as it is unethical to withhold therapy when clinically indicated. Medication use may affect the balance within the gut microbiome community (141). In fact, as most Lupus patients received hydroxychloroquine, the effect of this medication may be difficult to ascertain, and may need further investigation. It was therefore fortuitous that a number of patients were recruited who were in flare off medications at the time of evaluation, and the same associations for RG abundance and immune responses were generally found. These considerations notwithstanding, there are as yet no known mechanisms by which immunomodulatory medications result in microbial-antigen specific systemic immune responses.

In three independent SLE cohorts, from NYC, Philadelphia and Ohio, the inventors documented immunologic responses to a RG2 strain-specific lipoglycan-containing antigen, and the major features of these antibody responses appear to reiterate themes first identified in a form of post-infection GN that was common in Western societies before the widespread availability of antibiotics, and which continue to plague developing societies with less access to antibiotics. Whereas Ruminococci is a co-colonizer of the bowel, Streptococci are ubiquitous Gram-positive commensals that reside on our cutaneous and mucosal barriers. Pathogenic strains of group A *S. pyogenes*, which are responsible for limited skin and pharyngeal infections, can also be causal for epidemics of pediatric GN. In post-strep GN, although the kidneys are sterile, over-exuberant antimicrobial immune responses are responsible for immune complex deposition at subendothelial and subepithelial sites in the glomeruli of affected individuals, often associated with inflammatory arthritis (142). The lipoglycan-containing antigen of RG2 has not previously been studied.

During the course of clinical disease, LN may be the first manifestation of SLE, but most commonly occurs within a year of diagnosis and almost always within 5 years. However, LN can occur any time throughout the course of the disease, and may be seemingly disconnected from other disease manifestations (144, 145). Herein is discussed a case in which the initial years of modest Lupus disease activity were subsequently followed by development of a progressive IgG response to RG2 and active LN. Disease progression correlated with increasing antibody responses to native DNA, chromatin, glomerular extract, and appearance of IgG anti-C1q responses, as previously described (119, 146, 147). It is currently unknown if this is the only scenario as it is currently uncertain whether patients commonly first develop the autoimmune disease, SLE, and then become colonized with nephritogenic RG strain(s). In fact, active disease and progressive renal impairment may instead provide an intestinal environment more conducive to expansion of some RG strains. Lupus patients are reported to be more susceptible to shifts in their gut microbiome (148), and such instability may be intertwined with the current evidence that many have restricted diversity of their microbiome communities (FIG. 2A-2C). Alternatively, it may be that gut colonization with such nephritogenic strains commonly precedes a diagnosis of SLE, and overt glomerulonephritis may only develop at a later juncture. Without wishing to be bound by theory, the former hypothesis may be favored in part because of mounting evidence that overt Lupus disease is often preceded by a period of preclinical autoimmunity with serum anti-DNA responses (and other types of autoantibodies). This autoantibody response may precede onset of overt disease by many years (149). The pilot studies of unaffected relatives of active LN patients have detected family members with low but significant levels of IgG anti-RG2 antibodies, in the absence of anti-DNA responses, suggesting immune exposure/response to some RG strains may at times occur without progression to overt Lupus disease. Prospective longitudinal investigations are therefore needed to better understand the time course of RG colonization as it relates to onset (and recurrence) of LN.

Lupus nephritis is a major source of early mortality and overall morbidity (reviewed in (150)). The discovery of RG antibodies and their role in detecting LN and SLE may in part aid earlier diagnosis and better prognostic determinations, and a blood test that can substantially increase the level of confidence in the diagnosis of Lupus nephritis could also provide both medical and economic advantages. There are also great potential therapeutic implications, as current standard of care therapies are immunosuppressive or cytotoxic. It is possible that renal injury might then be lessened, or avoided entirely, if the offending pathobiont strain could be eradicated and replaced, or if the offending bacterial components could be bound in the gut by an orally administered agent, for harmless clearance.

The studies presented herein therefore provide a previously unsuspected paradigm for the causation of immune-complex mediated disease wherein pathogenic autoantibodies may be induced by molecular mimicry with a gut pathobiont. Without wishing to be bound by theory, it is suggested that the cell wall component of RG2, which is likely produced at high local levels in the gut as a consequence of high abundance colonization in susceptible individuals, is released into the systemic circulation due to a "leaky gut" that has increasingly been associated with a widening range of inflammatory and autoimmune conditions (151). In SLE patients, RG2 lipoglycan-containing antigen exposure to the peripheral immune system, presumably for long periods of time in the absence of intestinal symptoms, is postulated to induce an immune-complex disease with the classical features of serum sickness. Taken together, these studies may help to solve persistent paradoxes regarding the origins of anti-DNA antibodies and their roles in the pathogenesis of SLE (97).

Methods

Clinical trial design. Patients were consecutively recruited from the NYU Langone Medical Center and Bellevue Hospital. All patients fulfilled at least 4 of the American College of Rheumatology Criteria for the diagnosis of SLE (90). Patients were excluded from further study for the following criteria: 1) Pregnancy or breast-feeding; 2) Recent or current serious confounding medical disorder; 3) Current malignancy other than skin; 4) Cyclophosphamide within 12 months; 5) If on azathioprine, MMF, methotrexate, the dose must be stable for 4 weeks prior to study entry; 6) Serious infection within 3 months with hospitalization; 7) Antibiotic treatment within the preceding four months; 8) IgA deficiency.

Patients and healthy controls were enrolled with informed consent obtained, whereas our initial studies focused on the female subjects, as gender can affect the composition of gut microbiota (123). Patients were scored using the composite SLE disease activity index (SLEDAI), a validated weighted scale for 24 parameters, which was developed to aid clinical decision-making, with higher scores indicating more severe disease activity (153), and used a hybrid SLEDAI tool in which active nephritis is designated for proteinuria of >500 mg/day (108). The inventors characterized patients not on biologic agents as in clinical remission, if SLEDAI scores were "0". Patients were requested to provide blood and fecal samples, and clinical laboratory tests were obtained as part of routine care. Biobanked blood samples were obtained from patients in the Temple University and Ohio State University cohorts who met ACR criteria (90), with renal biopsy based evidence of active nephritis absolutely required from the latter, while fecal samples were unavailable.

Microbiota sampling. Fecal sampling was by a standardized and validated collection protocol using a special media (i.e., chopped meat enriched) for later recovery of viable bacteria. Microbial DNA from fecal samples was isolated by validated standard protocol, with extraction directly or after frozen and stored at −80° C. (as per Human Microbiome Project website www.hmpdacc.org).

16S rDNA gene sequence analysis. For phylogenetic assignments, the inventors analyzed diagnostic 16S ribosomal DNA (rDNA) gene sequences in libraries for each fecal sample (154-156). Briefly, to determine the distribution of operational taxonomic units (OTUs) (157, 158) the diagnostic V4 region of 16S rDNA gene was amplified with flanking oligo primers with embedded 16 bp barcodes, producing a 254 bp read length. From each sample, three replicate libraries were generated with the same bar-coded oligonucleotide primer pair, which were then pooled then purified (154), and stored until sequencing. With the MiSeq instrument (Illumina) in a 96-well format, these amplimers were generated and later characterized based on ~150 bp reads in both directions. Sequence determinations were performed in large batched MiSeq instrument runs, resulting in average of 44,394 (SD 37,503) sequences per sample in each MiSeq run. For these studies, more than 3.4 million assignable 16S rDNA reads from 78 (61 SLE and 17 HC) samples were determined.

Upstream informatics analysis of the 16S sequences. The quality-filtered pre-processed sequences of the community sequence data were analyzed using QIIME pipeline (159). The pipeline consists of the following steps: (i) clustering of the sequences into operational taxonomical units (OTUs) using UCLUST program at 97% similarity level (160); (ii) taxonomical assignment of each OTU by running RDP Classifier (110) at 80% bootstrap confidence on a representative sequence from each OTU; (iii) alignment of representative sequences using PyNAST (159) with the Greengenes core-set alignment template; (iv) building a phylogenetic tree for the OTUs using FASSTTREE program (161); and (v) calculating Unifrac distances between each sample (162). The data was then exported into R phyloseq (163) data structures and analyzed using custom reproducible RMarkdown scripts. Alpha diversity analyses, association, and correlation analyses, as well as most visualizations were performed in R. To decrease the number of features, the inventors focused on major taxa and OTUs, defined as those having mean relative abundance above 1% in all samples. For association with discrete variables, the inventors used Mann-Whitney-Wilcoxon test (in case of 2 categories) and Kruskal Wallis ANOVA test (in case of more than 2 categories) with taxa abundances normalized to relative abundance. Intertaxa correlations were determined using Pearson correlations of the centered log-ratio (CLR) transformed abundances with pseudo-count 1 added to ensure continuity of the normalization. Significance values were adjusted for multiple comparisons using false discovery rate (164), as appropriate. Principal coordinates analysis (PCoA) was calculated on Jensen-Shannon divergence dissimilarities and the significance of the clustering was determined using PERMANOVA (165).

Serum and plasma collection. Blood samples were collected in endotoxin-free vacutainer tubes (BD Biosciences) without anti-coagulant (serum) or with EDTA for plasma, using a standard protocol.

Bacterial culture and lipoglycan-containing antigen isolation. R. gnavus strains were cultured in chopped meat (CM) media (Anaerobe Systems) under anaerobic conditions. The bacterial cells were collected and pelleted then lysed by using the Bugbuster extraction reagent (Novagen, Millipore), after the protein extracts were further treated with Proteinase K (Qiagen) and size excluded to remove protein fragments and enrich for soluble lipoglycan-containing antigen (Amicon ultrafiltration devices with 10 kDa cut-off).

Antibody determinations. To determine IgG antibody levels to Ro (SSA) and dsDNA, the inventors used INOVA kits or in-house methods (166), which included custom multiplex bead-based assays (MagPix, Luminex). Extracts from cultured anerobic bacteria were separately conjugated to individual bead types in a custom multiplex immunoassay system, adapting a previously described approach (167). The cut-off for high IgG anti-RG2 levels was set based on the mean plus 2SD for values for sera from a group of 57 unaffected adult controls.

For DNA inhibition studies, ELISA microwells were coated with methylated BSA (Sigma) 5 ug/ml in PBS overnight then incubated with 50 ug/ml calf thymus DNA (Sigma) for 2 hrs at 37° C. After incubation, 3% BSA 0.1% gelatin in PBS was used to block for 1hr at room temperature (RT). Serial dilutions of calf thymus DNA in PBS 1% BSA were made 2-fold dilution, starting from 100 μg/ml. The sera samples were separately diluted in a 1:800 dilution with 1% BSA-PBS. Equal volume aliquots of calf thymus DNA at different concentrations were, with a constant dilution of a serum, or batched sera samples, incubated for 20 min at RT, then incubated on the coated plates for 1.5 hrs at RT with mild agitation. For detection, the inventors used goat anti-human Fc (gamma) HRP (Jackson ImmunoResearch), and. developed with TMB substrate (Biolegend).

For RG2 inhibition studies, the same protocol was used with aliquots of lipoglycan-containing antigen enriched preps that had lipoglycan functional equivalence based on ELISA using methyl-BSA coated wells, and these bacterial extracts two-fold serially diluted starting from 1:25.

Crithidia assays. An indirect immunofluorescent assay was used for the screening and semi-quantitative determination of anti-double stranded native DNA (dsDNA) IgG antibodies in human serum (INOVA). The manufacturer's protocol was adapted for inhibition studies by addition of aliquots of solutions of either calf thymus DNA or RG2 extract with concentrations as indicated in FIG. 5.

Immunoblotting. Electrophoretic separation used Bis-Tris mini gels (Novex, Thermo Fisher). The bacterial extracts were loaded at the same concentration, then transferred to membranes, which were incubated with sera diluted at 1:100, and incubated overnight at 4° C. For detection, anti-human IgG Biotin conjugated (Jackson ImmunoResearch Labs, USA) was added and developed by IRDye® 800CW Streptavidin (LI-COR®).

Transmission Electron Microscopy. For immunogold labeling of IgG bound to whole-mount bacteria, a fresh culture of bacteria was washed with PBS and fixed in 2% paraformaldehyde in PBS at 4° C. for 5 min, then absorbed on glow discharged formvar-carbon coated copper grids for 10 min. After washing with PBS, the grids were incubated with 50 mM glycine/PBS for 3 min, blocked with 1% cold-water fish skin gelatin (Sigma) for 5 min, and incubated with primary antibody in blocking solution for 1 hr at RT. Following washing with PBS, gold conjugated secondary antibodies (15 nm protein A-gold, Cell Microscopy Center, University Medical Center Utrecht, 35584 CX Utrecht, The Netherlands; or 12 nm colloidal gold-AffiniPure goat anti-human IgG, Jackson ImmunoResearch Labs, Inc., West Grove, Pa.) were applied in the blocking buffer for 30 min. After washing with PBS, the grids were fixed in 1% glutaraldehyde for 5 min. The grids were washed with distilled water, contrasted and embedded in a mixture of 3% uranyl acetate and 2% methylcellulose in a ratio of 1 to 9. Stained grids were examined under Philips CM-12 electron microscope (FEI; Eindhoven, the Netherlands) and photographed with a Gatan (4 k×2.7 k) digital camera (Pleasanton, Calif.).

Statistical analysis. Data are expressed as mean±SD or median (interquartile range). The Student unpaired t test was used in 2-group comparisons of normally distributed data, whereas the Mann-Whitney nonparametric test was used when the normality assumption was not met. Fisher's exact test was performed to evaluate bivariate associations between categorical variables. P values were considered significant at <0.05 for two-tailed tests. Prism software Version 7 (GraphPad) was used for all analyses.

Gut permeability testing. Serum studies can include determination of the levels of Zonulin (a human protein that regulates the gut barrier), LPS, soluble CD14 (sCD14), and/or alpha 1 acid glycoprotein (see, e.g., Sturgeon et al., Tissue Barriers 2016; 4: e1251384; Moreno-Navarrete et al., PLoS One 2012; 7: e37160; Rainone et al., Int J Obes (Lond) 2016; 40: 1026-1033; Fotis et al., L, J Rheumatol 2017; 44: 1624-1631). Fecal tests can include determining the levels of calprotectin and/or albumin (see, e.g., Shulman et al., J Pediatr 2008; 153: 646-650; Gisbert et al., Inflamm Bowel Dis 2009; 15: 1190-1198; Powell-Tuck, Gut 1986; 27 Suppl 1: 67-71.

Example 6. Alternate Method to Purify R. gnavus Antigen

The periplasm of the gram-positive R. gnavus strain R. gnavus strain (NCBI CC55_001C), which is termed herein R. gnavus 2, contains the antigen recognized by sera of Lupus patients who develop Lupus nephritis. This antigen comprises a lipoglycan, which is comprised of polymers with covalently linked lipid anchors (Fischer, 1994). This R. gnavus 2 antigen is antigenically distinct from structurally related molecules in a number of other strains of R. gnavus that have been tested.

An alternate purification method for the antigenic substance in the R. gnavus strain 2 bacteria has used cell disruption with a French press, followed by ultracentrifugation to remove the precipitate. The supernatant is subjected to butanol-water extraction and the lipoglycan-containing antigen distributes into the aqueous phase, and the butanol containing fraction is discarded. The soluble component is then passaged over a hydrophobic interaction chromatography (column (1.25×17 cm) of Octyl-Sepharose CL-4B (Sigma)) to isolate lipoglycan-containing fractions (Fischer, 1993) (Flaherty et al., 1996), both references incorporated herein in their entirety, where the fractions with desired immunologic properties activity are confirmed by ELISA or bead based immunoassay with sera from active SLE patients. The further characterization of the structural features of the antigen is performed by NMR, mass spectroscopy and gas chromatography/mass spectroscopy.

Evidence that Lupus Patients have Defects in the Gut Barrier that May Result in Systemic Immune Exposure to Intestinal Bacterial Antigens In health, there is a functional barrier in the gut that prevents the large-scale escape of bacteria and bacterial components from the gut lumen, as increased gut permeability and bacterial translocation have been associated with gastrointestinal diseases and systemic inflammatory diseases (reviewed in (Nagpal and Yadav, 2017)). The inventors therefore investigated for evidence of increased gut permeability with several commercially available assays. Specifically, faecal calprotectin was measured with Calprotectin ELISA (Cat: CAL35-KO1, Eagle Biosciences), serum sCD14 was measured by ELISA, Cat: DC140, R&D Systems, and serum alpha1 acid glycoprotein was measured by ELISA, Cat: DAGPOO, R&D Systems. Increased gut permeability was identified in a substantial subset of SLE patients.

Figure 13A:
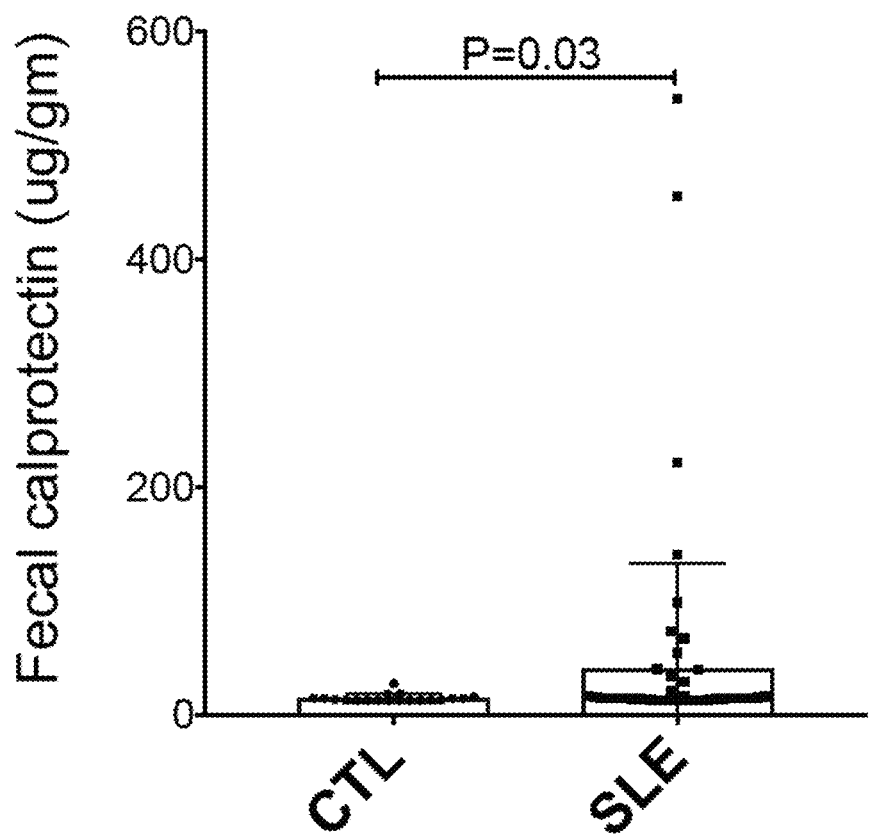
FIGS. 13A-C. SLE patients display faecal and serum biomarkers associated with increased gut permeability. SLE samples were from the NYU cohort of adult female SLE patients, with comparison to adult female controls without inflammatory or autoimmune disease (CTL). For each panel, 13A. Faecal calprotectin was measured with Calprotectin ELISA (Cat: CAL35-K01, Eagle Biosciences). 13B. Serum sCD14 was measured by ELISA, Cat: DC140, R&D Systems. 13C. Serum alphal acid glycoprotein by ELISA, Cat: DAGPOO, R&D Systems. All three tests showed that SLE patients had significantly raised values as compared to the controls. Assays were performed as per manufacturer's protocols. Unpaired t test with Welch's correction, two-tailed, with significance with P<0.05.
Figure 13B:
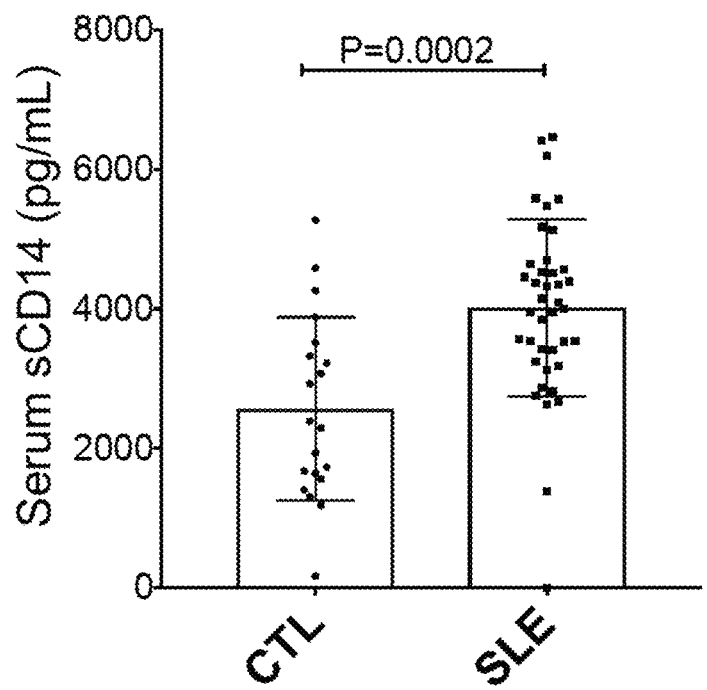
Figure 13C:
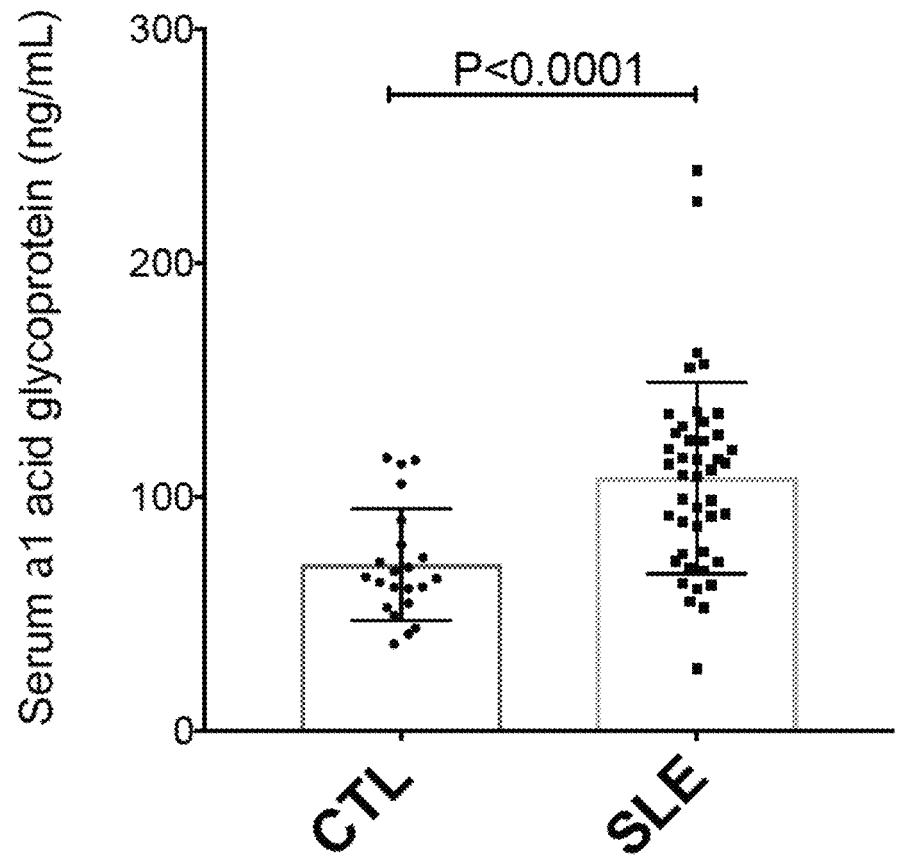

A subset of SLE patients was documented to have raised fecal levels of calprotectin, a 38 kDa protein from neutrophils which is not released into the bowel contents in healthy individuals (Shulman et al., 2008), (Gisbert et al., 2009) (FIG. 13A). In addition, there were significantly raised serum levels of soluble CD14 (sCD14) (FIG. 13B), a co-receptor for innate immune signaling and of alpha 1 acid glycoprotein (FIG. 13C, an acute phase reactant produced in the liver that can also be a sign of increased gut permeability (Fotis et al., 2017).

Immunoassay demonstrates that lipoglycan-containing antigen fraction from a R. gnavus 2 strain (NCBI CC55_001C) is recognized by serum IgG antibodies from Lupus patients, with higher levels of anti-lipoglycan fraction IgG in the Lupus nephritis patients compared to the Lupus patients without renal disease.

A lipoglycan-containing preparation from R. gnavus strain 2 (NCBI CC55_001C), of the family Lachnospiraceae, was purified using hydrophobic interaction chromatography, and evaluated for serum IgG reactivity using a customized antigen array with the MagPix bead-based system (Luminex). Briefly, 5 µg of the lipoglycan pool 2 (the fraction that was taken from the chromatographic separation, which contained lipoglycan) was incubated with 5 million MagPix beads (Luminex) prepared for standard surface chemistry by the manufacturer, followed by washing and blocking of unfilled sites with human serum albumin (HSA). As shown in Table 11, the results show strong IgG reactivity (MFI by Luminex instrument) with the R. gnavus 2 (NCBI CC55_001C) purified lipoglycan-containing preparation, which is more strongly reactive, but shows the same reactivity pattern, as the adjacent results for bacterial extract of the R. gnavus 2 prepared using a commercial kit from Millipore that contains lysozyme and Benzonase containing solutions (Bugbuster kit, Millipore) followed by treating extracts with Proteinase K (20,000 units/ml at 54° C. (Qiagen)), as per manufacturer's instructions, followed by inhibiting Proteinase K with PMSF and dialyzing against PBS. By comparison there was little or no reactivity with the R. gnavus strain 1 (NCBI VPI C7-9) or with a purified E. coli lipopolysaccharide (LPS)(Sigma). There was also little detectable IgG reactivity with extracts of other intestinal bacterial species; Bacteroides, or P. copri (strain K). Beads coated with purified mammalian chromatin were used to detect Lupus-associated IgG autoantibodies. Background levels were shown for beads coated with human serum albumin (HAS). These studies using beads coated with affinity purified anti-human IgG served as a positive control to detect the IgG in the serum samples. Results for the same serum type and dilution were performed in the same well. These results show that SLE sera has the same general selective IgG reactivity pattern, but with stronger IgG reactivity signal for the R. gnavus 2 lipoglycan-containing preparation produced using butanol-water extraction and hydrophobic interaction chromatography as compared to the preparation produced using nuclease and protease from the same bacteria.

TABLE 11

| | Serum dilution | anti-human IgG | R. gnavus 2 purified Lipoglycan Pool 2 | R. gnavus strain 2 extract | R. gnavus strain 1 extract | E. coli LPS | Bacteroides | P. copri K | Chromalin | Human Serum Albumin |
|---|---|---|---|---|---|---|---|---|---|---|
| SLE patient serum pool | 1:200 | 13353 | 26354 | 1822 | 478 | 819 | 395 | 580 | 21528 | 126 |
| | 1:800 | 9745 | 19383 | 727 | 204 | 274 | 93 | 135 | 13874 | 34 |
| | 1:3200 | 9244 | 8201 | 310 | 80 | 79 | 25 | 32 | 8693 | 9 |
| SLE patient(47) with renal disease | 1:200 | 10978 | 24016 | 1449 | 87 | 355 | 178 | 408 | 2284 | 17 |
| | 1:800 | 10384 | 19335 | 727 | 58 | 146 | 63 | 104 | 277 | 7 |
| | 1:3200 | 7923 | 9588 | 327 | 30 | 49 | 20 | 19 | 0 | 2 |
| SLE patient (96) without renal disease | 1:200 | 11349 | 1070 | 514 | 544 | 843 | 345 | 587 | 257 | 88 |
| | 1:800 | 9025 | 305 | 197 | 197 | 345 | 103 | 201 | 298 | 30 |
| | 1:3200 | 8343 | 72 | 57 | 71 | 88 | 29 | 53 | 87 | 3 |
| Control (CS2) adult subject | 1:200 | 8495 | 11180 | 508 | 176 | 308 | 104 | 171 | 454 | 21 |
| | 1:800 | 8241 | 5011 | 242 | 103 | 113 | 34 | 47 | 206 | 7 |
| | 1:3200 | 7828 | 1179 | 94 | 53 | 36 | 11 | 15 | 0 | 4 |

R. gnavus 2 (NCBI CC55_001C) lipoglycan-containing preparation produced using butanol-water extraction and hydrophobic interaction chromatography has the same pattern of IgG reactivity as nuclease-protease-treated extract, with high level of IgG reactivity associated with the pool of SLE sera, which included patients with Lupus nephritis, and a much higher level of IgG reactivity in patient S-47 that has lupus nephritis compared to patient S-96 without renal disease and the healthy control (CS2). Results are form a bead-based assay of human serum IgG reactivity, and were performed of human sera diluted with 1% BSA in phosphate buffered saline. Comparisons were made for reactivity of IgG in a pool made from the sera of 20 SLE patients that included individuals with active Lupus nephritis. Studies were performed with MapPix instrument (Milliplex MAP, Luminex).

REFERENCES

1. Kuo C F, Grainge M J, Valdes A M, See L C, Luo S F, Yu K H, et al. Familial Aggregation of Systemic Lupus Erythematosus and Coaggregation of Autoimmune Diseases in Affected Families. JAMA Intern Med. 2015; 175(9):1518-26.
2. Bentham J, Morris D L, Cunninghame Graham D S, Pinder C L, Tombleson P, Behrens T W, et al. Genetic association analyses implicate aberrant regulation of innate and adaptive immunity genes in the pathogenesis of systemic lupus erythematosus. Nat Genet. 2015; 47(12): 1457-64.
3. Larsen R A, Solheim B G. Family studies in systemic lupus erythematosus. V. Presence of antinuclear factors (ANTFs) in relatives and spouses of selected SLE probands. Acta Med Scand Suppl. 1972; 543:55-64.
4. Bruner B F, Guthridge J M, Lu R, Vidal G, Kelly J A, Robertson J M, et al. Comparison of autoantibody specificities between traditional and bead-based assays in a large, diverse collection of patients with systemic lupus erythematosus and family members. Arthritis Rheum. 2012; 64(11):3677-86.
5. Zarmbinski M A, Messner R P, Mandel J S. Anti-dsDNA antibodies in laboratory workers handling blood from patients with systemic lupus erythematosus. J Rheumatol. 1992; 19(9): 1380-4.
6. Song S J, Lauber C, Costello E K, Lozupone C A, Humphrey G, Berg-Lyons D, et al. Cohabiting family members share microbiota with one another and with their dogs. Elife. 2013; 2:e00458.
7. Schloss P D, Iverson K D, Petrosino J F, Schloss S J. The dynamics of a family's gut microbiota reveal variations on a theme. Microbiome. 2014; 2:25.
8. Botto M, WalportMJ. C1q, autoimmunity and apoptosis. Immunobiology. 2002; 205(4-5):395-406.
9. Silverman G J, Barbas S, Roben P, Burton D R. Repertoire cloning of human lupus autoantibodies. Ann N Y Acad Sci. 1995; 764:565-6.
10. Silverman G J, Srikrishnan R, Germar K, Goodyear C S, Andrews K A, Ginzler E M, et al. Genetic imprinting of autoantibody repertoires in systemic lupus erythematosus patients. Clinical and experimental immunology. 2008; 153(1):102-16.
11. Honda K, Littman D R. The microbiota in adaptive immune homeostasis and disease. Nature. 2016; 535 (7610):75-84.
12. Wesemann D R, Portuguese A J, Meyers R M, Gallagher M P, Cluff-Jones K, Magee J M, et al. Microbial colonization influences early B-lineage development in the gut lamina propria. Nature. 2013; 501(7465):112-5.
13. Wu H J, Ivanov, II, Darce J, Hattori K, Shima T, Umesaki Y, et al. Gut-residing segmented filamentous bacteria drive autoimmune arthritis via T helper 17 cells. Immunity. 2010; 32(6):815-27.
14. Chung H, Pamp S J, Hill J A, Surana N K, Edelman S M, Troy E B, et al. Gut immune maturation depends on colonization with a host-specific microbiota. Cell. 2012; 149(7):1578-93.
15. Malnick S D, Melzer E, Attali M, Duek G, Yahav J. *Helicobacter pylori*: friend or foe? World J Gastroenterol. 2014; 20(27):8979-85.
16. Montalban C, Manzanal A, Boixeda D, Redondo C, Bellas C. Treatment of low-grade gastric MALT lymphoma with *Helicobacter pylori* eradication. Lancet. 1995; 345(8952):798-9.
17. Soergel D A, Dey N, Knight R, Brenner S E. Selection of primers for optimal taxonomic classification of environmental 16S rRNA gene sequences. ISME J. 2012; 6(7):1440-4.
18. Langille M G, Zaneveld J, Caporaso J G, McDonald D, Knights D, Reyes J A, et al. Predictive functional profiling of microbial communities using 16S rRNA marker gene sequences. Nat Biotechnol. 2013; 31(9): 814-21.
19. Scanlan P D, Shanahan F, O'Mahony C, Marchesi J R. Culture-independent analyses of temporal variation of the dominant fecal microbiota and targeted bacterial subgroups in Crohn's disease. J Clin Microbiol. 2006; 44(11): 3980-8.
20. Frank D N, St Amand A L, Feldman R A, Boedeker E C, Harpaz N, Pace N R. Molecular-phylogenetic characterization of microbial community imbalances in human inflammatory bowel diseases. Proc Natl Acad Sci USA. 2007; 104(34):13780-5.
21. Scher J U, Sczesnak A, Longman R S, Segata N, Ubeda C, Bielski C, et al. Expansion of intestinal *Prevotella copri* correlates with enhanced susceptibility to arthritis. Elife. 2013; 2:e01202.
22. Hevia A, Milani C, Lopez P, Cuervo A, Arboleya S, Duranti S, et al. Intestinal dysbiosis associated with systemic lupus erythematosus. MBio. 2014; 5(5):e01548-14.
23. Silverman G J, Getu, L., Niu, H., El Bannodi, H., Heguy, A., Alekseyenko, A., Buyon, J. P., Azzouz, D. Does dysbiosis with in the intestinal microbiome contribute to SLE pathogeensis? Arthritis Rheumatology. 2015; Suppl (Abstract 2077).
24. Azzouz D F, Getu, L., Anquetil, C., Buyon, J. B. and Silverman, G. J. Intestinal Microbial Dysbiosis in SLE Is Linked to Elevated IgA and Induction of Autoimmunity. Arthritis Rheum. 2016(suppl.).
25. Human Microbiome Jumpstart Reference Strains C, Nelson K E, Weinstock G M, Highlander S K, Worley K C, Creasy H H, et al. A catalog of reference genomes from the human microbiome. Science. 2010; 328(5981):994-9.
26. Atarashi K, Tanoue T, Oshima K, Suda W, Nagano Y, Nishikawa H, et al. Treg induction by a rationally selected mixture of Clostridia strains from the human microbiota. Nature. 2013; 500(7461):232-6.
27. Eun C S, Mishima Y, Wohlgemuth S, Liu B, Bower M, Carroll I M, et al. Induction of bacterial antigen-specific colitis by a simplified human microbiota consortium in gnotobiotic interleukin-10−/− mice. Infect Immun. 2014; 82(6):2239-46.
28. Crost E H, Tailford L E, Le Gall G, Fons M, Henrissat B, Juge N. Utilisation of mucin glycans by the human gut symbiont *Ruminococcus gnavus* is strain-dependent. PLoS One. 2013; 8(10):e76341.
29. Dabard J, Bridonneau C, Phillipe C, Anglade P, Molle D, Nardi M, et al. Ruminococcin A, a new lantibiotic produced by a *Ruminococcus gnavus* strain isolated from human feces. Appl Environ Microbiol. 2001; 67(9):4111-8.
30. Crost E H, Ajandouz E H, Villard C, Geraert P A, Puigserver A, Fons M. Ruminococcin C, a new anti-*Clostridium perfringens* bacteriocin produced in the gut by the commensal bacterium *Ruminococcus gnavus* E1. Biochimie. 2011; 93(9):1487-94.
31. Martin R, Chain F, Miguel S, Lu J, Gratadoux J J, Sokol H, et al. The commensal bacterium *Faecalibacterium prausnitzii* is protective in DNBS-induced chronic moderate and severe colitis models. Inflamm Bowel Dis. 2014; 20(3):417-30.
32. Ginsburg I. Role of lipoteichoic acid in infection and inflammation. Lancet Infect Dis. 2002; 2(3): 171-9.

33. Josephson S L, Stinson M W, Millar S J, Cohen R E. Purification of lipoteichoic acid by chromatography in water-organic solvent systems. Infect Immun. 1986; 51(2):378-84.

34. Tang C H, Hsu C J, Yang W H, Fong Y C. Lipoteichoic acid enhances IL-6 production in human synovial fibroblasts via TLR2 receptor, PKCdelta and c-Src dependent pathways. Biochem Pharmacol. 2010; 79(11):1648-57.

35. Chen J, Fujino Y, Takahashi T. Experimental uveitis induced by intravitreal or intravenous lipoteichoic acid in rabbits. Jpn J Ophthalmol. 1999; 43(5):368-74.

36. Sriskandan S, Cohen J. Gram-positive sepsis. Mechanisms and differences from gram-negative sepsis. Infect Dis Clin North Am. 1999; 13(2):397-412.

37. Goilav B, Putterman C. The Role of Anti-DNA Antibodies in the Development of Lupus Nephritis: A Complementary, or Alternative, Viewpoint? Semin Nephrol. 2015; 35(5):439-43.

38. VanDeVoorde RG, 3rd. Acute poststreptococcal glomerulonephritis: the most common acute glomerulonephritis. Pediatr Rev. 2015; 36(1):3-12; quiz 3.

39. Rekvig O P, Van der Vlag J. The pathogenesis and diagnosis of systemic lupus erythematosus: still not resolved. Semin Immunopathol. 2014; 36(3):301-11.

40. Kuczynski J, Stombaugh J, Walters W A, Gonzalez A, Caporaso J G, Knight R. Using QIIME to analyze 16S rRNA gene sequences from microbial communities. Curr Protoc Bioinformatics. 2011; Chapter 10:Unit 10 7.

41. Okada H, Kuhn C, Feillet H, Bach J F. The 'hygiene hypothesis' for autoimmune and allergic diseases: an update. Clinical and experimental immunology. 2010; 160(1):1-9.

42. Joossens M, Huys G, Cnockaert M, De Preter V, Verbeke K, Rutgeerts P, et al. Dysbiosis of the faecal microbiota in patients with Crohn's disease and their unaffected relatives. Gut. 2011; 60(5):631-7.

43. Willing B P, Dicksved J, Halfvarson J, Andersson A F, Lucio M, Zheng Z, et al. A pyrosequencing study in twins shows that gastrointestinal microbial profiles vary with inflammatory bowel disease phenotypes. Gastroenterology. 2010; 139(6):1844-54 e1.

44. Buyon J P, Petri M A, Kim M Y, Kalunian K C, Grossman J, Hahn B H, et al. The effect of combined estrogen and progesterone hormone replacement therapy on disease activity in systemic lupus erythematosus: a randomized trial. Ann Intern Med. 2005; 142(12 Pt 1):953-62.

45. Gladman D D, Ibanez D, Urowitz M B. Systemic lupus erythematosus disease activity index 2000. J Rheumatol. 2002; 29(2):288-91.

46. Abrahamowicz M, Fortin P R, du Berger R, Nayak V, Neville C, Liang M R. The relationship between disease activity and expert physician's decision to start major treatment in active systemic lupus erythematosus: a decision aid for development of entry criteria for clinical trials. J Rheumatol. 1998; 25(2):277-84.

47. Gladman D D, Urowitz M B, Kagal A, Hallett D. Accurately describing changes in disease activity in Systemic Lupus Erythematosus. J Rheumatol. 2000; 27(2): 377-9.

48. Hornef M W, Pabst O. Real friends: *Faecalibacterium prausnitzii* supports mucosal immune homeostasis. Gut. 2016; 65(3):365-7.

49. Crost E H, Pujol A, Ladire M, Dabard J, Raibaud P, Carlier J P, et al. Production of an antibacterial substance in the digestive tract involved in colonization-resistance against *Clostridium perfringens*. Anaerobe. 2010; 16(6): 597-603.

50. Pujol A, Crost E H, Simon G, Barbe V, Vallenet D, Gomez A, et al. Characterization and distribution of the gene cluster encoding RumC, an anti-*Clostridium perfringens* bacteriocin produced in the gut. FEMS Microbiol Ecol. 2011; 78(2):405-15.

51. Schnupf P, Gaboriau-Routhiau V, Cerf-Bensussan N. Host interactions with Segmented Filamentous Bacteria: an unusual trade-off that drives the post-natal maturation of the gut immune system. Semin Immunol. 2013; 25(5): 342-51.

52. Ivanov, II, Atarashi K, Manel N, Brodie E L, Shima T, Karaoz U, et al. Induction of intestinal Th17 cells by segmented filamentous bacteria. Cell. 2009; 139(3):485-98.

53. Gaboriau-Routhiau V, Rakotobe S, Lecuyer E, Mulder I, Lan A, Bridonneau C, et al. The key role of segmented filamentous bacteria in the coordinated maturation of gut helper T cell responses. Immunity. 2009; 31(4):677-89.

54. Umesaki Y, Setoyama H, Matsumoto S, Imaoka A, Itoh K. Differential roles of segmented filamentous bacteria and clostridia in development of the intestinal immune system. Infect Immun. 1999; 67(7):3504-11.

55. Harlow E, Lane D. Using antibodies: a laboratory manual. Cold Spring Harbor, N.Y.: Cold Spring Harbor Laboratory Press; 1999.

56. Datta S K, Patel H, Berry D. Induction of a cationic shift in IgG anti-DNA autoantibodies. Role of T helper cells with classical and novel phenotypes in three murine models of lupus nephritis. J Exp Med. 1987; 165(5):1252-68.

57. Gronwall C, Akhter E, Oh C, Burlingame R W, Petri M, Silverman G J. IgM autoantibodies to distinct apoptosis-associated antigens correlate with protection from cardiovascular events and renal disease in patients with SLE. Clin Immunol. 2012; 142(3):390-8.

58. Gronwall C, Clancy R M, Getu L, Lloyd K A, Siegel D L, Reed J H, et al. Modulation of natural IgM autoantibodies to oxidative stress-related neo-epitopes on apoptotic cells in newborns of mothers with anti-Ro autoimmunity. J Autoimmun. 2016; 73:30-41.

59. Pelzek A J, Gronwall C, Rosenthal P, Greenberg J D, McGeachy M, Moreland L, et al. Disease associated anti-citrullinated protein memory B cells in rheumatoid arthritis persist in clinical remission. Arthritis Rheumatol. 2017.

60. Atarashi K, Tanoue T, Shima T, Imaoka A, Kuwahara T, Momose Y, et al. Induction of colonic regulatory T cells by indigenous *Clostridium* species. Science. 2011; 331 (6015):337-41.

61. Kwinn L A, Nizet V. How group A *Streptococcus* circumvents host phagocyte defenses. Future Microbiol. 2007; 2(1):75-84.

62. Holm S E. Hypothesis on the pathogenesis of post-streptococcal glomerulonephritis based on recent clinical and experimental research. Zentralbl Bakteriol. 1990; 274(3):325-32.

63. Sizova M V, Muller P, Panikov N, Mandalakis M, Hohmann T, Hazen A, et al. *Stomatobaculum longum* gen. nov., sp. nov., an obligately anaerobic bacterium from the human oral cavity. Int J Syst Evol Microbiol. 2013; 63(Pt 4):1450-6.

64. Marcille F, Gomez A, Joubert P, Ladire M, Veau G, Clara A, et al. Distribution of genes encoding the trypsin-dependent lantibiotic ruminococcin A among bacteria isolated from human fecal microbiota. Appl Environ Microbiol. 2002; 68(7):3424-31.
65. Gomez A, Ladire M, Marcille F, Fons M. Trypsin mediates growth phase-dependent transcriptional tegulation of genes involved in biosynthesis of ruminococcin A, a lantibiotic produced by a *Ruminococcus gnavus* strain from a human intestinal microbiota. J Bakteriol. 2002; 184(1): 18-28.
66. Gomez A, Ladire M, Marcille F, Nardi M, Fons M. Characterization of ISRgn1, a novel insertion sequence of the IS3 family isolated from a bacteriocin-negative mutant of *Ruminococcus gnavus* E1. Appl Environ Microbiol. 2002; 68(8):4136-9.
67. Hoffmann T W, Pham H P, Bridonneau C, Aubry C, Lamas B, Martin-Gallausiaux C, et al. Microorganisms linked to inflammatory bowel disease-associated dysbiosis differentially impact host physiology in gnotobiotic mice. ISME J. 2015.
68. Carroll I M, Maharshak N. Enteric bacterial proteases in inflammatory bowel disease-pathophysiology and clinical implications. World J Gastroenterol. 2013; 19(43):7531-43.
69. Maharshak N, Huh E Y, Paiboonrungruang C, Shanahan M, Thurlow L, Herzog J, et al. *Enterococcus faecalis* Gelatinase Mediates Intestinal Permeability via Protease-Activated Receptor 2. Infect Immun. 2015; 83(7):2762-70.
70. Roseth A G, Aadland E, Jahnsen J, Raknerud N. Assessment of disease activity in ulcerative colitis by faecal calprotectin, a novel granulocyte marker protein. Digestion. 1997; 58(2): 176-80.
71. Hang L M, Izui S, Dixon F J. (NZW×BXSB)F1 hybrid. A model of acute lupus and coronary vascular disease with myocardial infarction. J Exp Med. 1981; 154(1):216-21.
72. Bubier J A, Bennett S M, Sproule T J, Lyons B L, Olland S, Young D A, et al. Treatment of BXSB-Yaa mice with IL-21R-Fc fusion protein minimally attenuates systemic lupus erythematosus. Ann N Y Acad Sci. 2007; 1110:590-601.
73. Merino R, Shibata T, De Kossodo S, Izui S. Differential effect of the autoimmune Yaa and lpr genes on the acceleration of lupus-like syndrome in MRL/MpJ mice. Eur J Immunol. 1989; 19(11):2131-7.
74. Hudgins C C, Steinberg R T, Klinman D M, Reeves M J, Steinberg A D. Studies of consomic mice bearing the Y chromosome of the BXSB mouse. J Immunol. 1985; 134(6):3849-54.
75. Boneparth A, Huang W, Bethunaickan R, Woods M, Sahu R, Arora S, et al. TLR7 influences germinal center selection in murine SLE. PLoS One. 2015; 10(3): e0119925.
76. Wang Y, Zhang L, Wei P, Zhang H, Liu C. Inhibition of PI3Kdelta improves systemic lupus in mice. Inflammation. 2014; 37(3):978-83.
77. Jain S, Park G, Sproule T J, Christianson G J, Leeth C M, Wang H, et al. Interleukin 6 Accelerates Mortality by Promoting the Progression of the Systemic Lupus Erythematosus-Like Disease of BXSB.Yaa Mice. PLoS One. 2016; 11(4):e0153059.
78. Champely S. pwr: Basic Functions for Power Analysis. R package version 1.2-0. 2016.
79. el Bannoudi H, Han W G, Stoop J N, Louis-Plence P, Huizinga T W, Toes R E. DX5+CD4+ T cells modulate CD4+ T-cell response via inhibition of IL-12 production by DCs. Eur J Immunol. 2013; 43(2):439-46.
80. Lawrence R C, Felson D T, Helmick C G, Arnold L M, Choi H, Deyo R A, Gabriel S, Hirsch R, Hochberg M C, Hunder G G, Jordan J M, Katz J N, Kremers H M, Wolfe F, National Arthritis Data W. Estimates of the prevalence of arthritis and other rheumatic conditions in the United States. Part II. Arthritis Rheum. 2008; 58(1):26-35.
81. Duarte C C M, Ines L, Liang M H. Epidemiology of Systemic Lupus Erythematosus. In: Lahita R, Buyon, J., Koike, T., editor. Systemic Lupus Erythematosus. 5th ed. London, England: Elsevier; 2011. p. 36-52.
82. Skerman V B D, McGowan V, Sneath P H A. 1980. Approved lists of bacterial names. Int. J. Syst. Bacteriol. 30:225-420.
83. Tsokos G C. Systemic lupus erythematosus. *N Engl J Med.* 2011; 365(22):2110-21.
84. Menzel A. E. O.; Heidelberger M. Cell protein fractions of bovine and avian tubercle *bacillus* strains and of the timothygrass *bacillus*. *J Biol Chem.* 1938; 124(301-3-7.
85. Winkenwerder W L, Buell M V, and Howard J E. The Sensitizing Properties of the Nucleic Acids and Their Derivatives. *Science.* 1939; 90(2337):356.
86. Sevag M G L, D. B.; Smolen, J. The isolation of the components of streptococcal nucleoproteins in serologically active form. *J Biol Chem.* 1938; 124(425-36.
87. Ceppellini R, Polli E, and Celada F. A DNA-reacting factor in serum of a patient with lupus erythematosus diffusus. *Proc Soc Exp Biol Med.* 1957; 96(3):572-4.
88. Friou G J. Identification of the nuclear component of the interaction of lupus erythematosus globulin and nuclei. *J Immunol.* 1958; 80(6):476-81.
89. Robbins W C, Holman H R, Deicher H, and Kunkel H G. Complement fixation with cell nuclei and DNA in lupus erythematosus. *Proc Soc Exp Biol Med.* 1957; 96(3):575-9.
90. Hochberg M C. Updating the American College of Rheumatology revised criteria for the classification of systemic lupus erythematosus. *Arthritis Rheum.* 1997; 40(9):1725.
91. Pisetsky D S. Anti-DNA antibodies—quintessential biomarkers of SLE. *Nat Rev Rheumatol.* 2016; 12(2): 102-10.
92. Borchers A T, Leibushor N, Naguwa S M, Cheema G S, Shoenfeld Y, and Gershwin M E. Lupus nephritis: a critical review. *Autoimmun Rev.* 2012; 12(2):174-94.
93. Goilav B, and Putterman C. The Role of Anti-DNA Antibodies in the Development of Lupus Nephritis: A Complementary, or Alternative, Viewpoint? *Semin Nephrol.* 2015; 35(5):439-43.
94. Agnello V, Koffler D, and Kunkel H G. Immune complex systems in the nephritis of systemic lupus erythematosus. *Kidney Int.* 1973; 3 (2): 90-9.
95. Reichlin M, and Wolfson-Reichlin M. Evidence for the participation of anti-ribosomal P antibodies in lupus nephritis. *Arthritis Rheum.* 1999; 42(12):2728-9.
96. Mannik M, Merrill C E, Stamps L D, and Wener M H. Multiple autoantibodies form the glomerular immune deposits in patients with systemic lupus erythematosus. *J Rheumatol.* 2003; 30(7): 1495-504.
97. Pedersen H L, Horvei K D, Thiyagarajan D, Seredkina N, and Rekvig O P. Murine and Human Lupus Nephritis: Pathogenic Mechanisms and Theoretical Strategies for Therapy. *Semin Nephrol.* 2015; 35(5):427-38.
98. Silverman G J, Srikrishnan R, Germar K, Goodyear C S, Andrews K A, Ginzler E M, and Tsao B P. Genetic imprinting of autoantibody repertoires in systemic lupus erythematosus patients. *Clinical and experimental immunology.* 2008; 153 (1): 102-16.

99. Roben P, Barbas S M, Sandoval L, Lecerf J M, Stollar B D, Solomon A, and Silverman G J. Repertoire cloning of lupus anti-DNA autoantibodies. *J Clin Invest.* 1996; 98(12):2827-37.

100. Bengmark S. Ecological control of the gastrointestinal tract. The role of probiotic flora. *Gut.* 1998; 42(1):2-7.

101. Gill S R, Pop M, Deboy R T, Eckburg P B, Turnbaugh P J, Samuel B S, Gordon J I, Relman D A, Fraser-Liggett C M, and Nelson K E. Metagenomic analysis of the human distal gut microbiome. *Science.* 2006; 312(5778): 1355-9.

102. Honda K, and Littman D R. The microbiota in adaptive immune homeostasis and disease. *Nature.* 2016; 535 (7610):75-84.

103. Wesemann D R, Portuguese A J, Meyers R M, Gallagher M P, Cluff-Jones K, Magee J M, Panchakshari R A, Rodig S J, Kepler T B, and Alt F W. Microbial colonization influences early B-lineage development in the gut lamina propria. *Nature.* 2013; 501(7465):112-5.

104. Sender R, Fuchs S, and Milo R. Revised Estimates for the Number of Human and Bacteria Cells in the Body. *PLoS Biol.* 2016; 14(8):e1002533.

105. Arnolds K L, and Lozupone C A. Striking a Balance with Help from our Little Friends—How the Gut Microbiota Contributes to Immune Homeostasis. *Yale J Biol Med.* 2016; 89(3):389-95.

106. Rosser E C, and Mauri C. A clinical update on the significance of the gut microbiota in systemic autoimmunity. *J Autoimmun.* 2016; 74(85-93.

107. Hevia A, Milani C, Lopez P, Cuervo A, Arboleya S, Duranti S, Turroni F, Gonzalez S, Suarez A, Gueimonde M, et al. Intestinal dysbiosis associated with systemic lupus erythematosus. *MBio.* 2014; 5(5):e01548-14.

108. Petri M, Kim M Y, Kalunian K C, Grossman J, Hahn B H, Sammaritano L R, Lockshin M, Merrill J T, Belmont H M, Askanase A D, et al. Combined oral contraceptives in women with systemic lupus erythematosus. *N Engl J Med.* 2005; 353(24):2550-8.

109. Cole J R, Wang Q, Fish J A, Chai B, McGarrell D M, Sun Y, Brown C T, Porras-Alfaro A, Kuske C R, and Tiedje J M. Ribosomal Database Project: data and tools for high throughput rRNA analysis. *Nucleic Acids Res.* 2014; 42(Database issue):D633-42.

110. Wang Q, Garrity G M, Tiedje J M, and Cole J R. Naive Bayesian classifier for rapid assignment of rRNA sequences into the new bacterial taxonomy. *Appl Environ Microbiol.* 2007; 73(16): 5261-7.

111. Scher J U, Sczesnak A, Longman R S, Segata N, Ubeda C, Bielski C, Rostron T, Cerundolo V, Pamer E G, Abramson S B, et al. Expansion of intestinal *Prevotella copri* correlates with enhanced susceptibility to arthritis. *Elife.* 2013; 2(e01202.

112. Fernandez-Murga M L, and Sanz Y. Safety Assessment of *Bacteroides uniformis* CECT 7771 Isolated from Stools of Healthy Breast-Fed Infants. *PLoS One.* 2016; 11(1): e0145503.

113. Gauffin Cano P, Santacruz A, Moya A, and Sanz Y. *Bacteroides uniformis* CECT 7771 ameliorates metabolic and immunological dysfunction in mice with high-fat-diet induced obesity. *PLoS One.* 2012; 7(7):e41079.

114. Hornef M W, and Pabst O. Real friends: *Faecalibacterium prausnitzii* supports mucosal immune homeostasis. *Gut.* 2016; 65(3):365-7.

115. Martin R, Chain F, Miguel S, Lu J, Gratadoux J J, Sokol H, Verdu E F, Bercik P, Bermudez-Humaran L G, and Langella P. The commensal bacterium *Faecalibacterium prausnitzii* is protective in DNBS-induced chronic moderate and severe colitis models. *Inflamm Bowel Dis.* 2014; 20(3):417-30.

116. Ryc M, Wagner B, Wagner M, and Bicova R. Electron microscopic localization of lipoteichoic acid on group *A. streptococci.* *Zentralbl Bakteriol Mikrobiol Hyg A.* 1988; 269(2): 168-78.

117. Davis P, Cumming R H, and Verrier-Jones J. Relationship between anti-DNA antibodies complement consumption and circulating immune complexes in systemic lupus erythematosus. *Clinical and experimental immunology.* 1977; 28(2):226-32.

118. Lefkowith J B, Kiehl M, Rubenstein J, DiValerio R, Bernstein K, Kahl L, Rubin R L, and Gourley M. Heterogeneity and clinical significance of glomerular-binding antibodies in systemic lupus erythematosus. *J Clin Invest.* 1996; 98(6): 1373-80.

119. Pioltelli P, Procaccio F, Invernizzi F, Ponticelli C, and Tarantino A. Correlations between anti-dsDNA antibodies, complement levels and clinical course in SLE patients treated with steroid pulse therapy. *Boll Ist Sieroter Milan.* 1978; 57(4):485-9.

120. Ho A, Barr S G, Magder L S, and Petri M. A decrease in complement is associated with increased renal and hematologic activity in patients with systemic lupus erythematosus. *Arthritis Rheum.* 2001; 44(10):2350-7.

121. Tozzoli R, Bizzaro N, Tonutti E, Villalta D, Bassetti D, Manoni F, Piazza A, Pradella M, Rizzotti P, and Italian Society of Laboratory Medicine Study Group on the Diagnosis of Autoimmune D. Guidelines for the laboratory use of autoantibody tests in the diagnosis and monitoring of autoimmune rheumatic diseases. *Am J Clin Pathol.* 2002; 117(2):316-24.

122. Weening J J, D'Agati V D, Schwartz M M, Seshan S V, Alpers C E, Appel G B, Balow J E, Bruijn J A, Cook T, Ferrario F, et al. The classification of glomerulonephritis in systemic lupus erythematosus revisited. *J Am Soc Nephrol.* 2004; 15(2): 241-50.

123. Yurkovetskiy L, Burrows M, Khan A A, Graham L, Volchkov P, Becker L, Antonopoulos D, Umesaki Y, and Chervonsky A V. Gender bias in autoimmunity is influenced by microbiota. *Immunity.* 2013; 39(2):400-12.

124. Liu C, Finegold S M, Song Y, and Lawson P A. Reclassification of *Clostridium coccoides, Ruminococcus hansenii, Ruminococcus hydrogenotrophicus, Ruminococcus luti, Ruminococcus productus* and *Ruminococcus schinkii* as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces. *Int J Syst Evol Microbiol.* 2008; 58(Pt 8):1896-902.

125. Flint H J, Bayer E A, Rincon M T, Lamed R, and White B A. Polysaccharide utilization by gut bacteria: potential for new insights from genomic analysis. *Nat Rev Microbiol.* 2008; 6(2): 121-31.

126. Faith J J, Guruge J L, Charbonneau M, Subramanian S, Seedorf H, Goodman A L, Clemente J C, Knight R, Heath A C, Leibel R L, et al. The long-term stability of the human gut microbiota. *Science.* 2013; 341(6141): 1237439.

127. Sagheddu V, Patrone V, Miragoli F, Puglisi E, and Morelli L. Infant Early Gut Colonization by Lachnospiraceae: High Frequency of *Ruminococcus gnavus.* *Front Pediatr.* 2016; 4(57.

128. Human Microbiome Jumpstart Reference Strains C, Nelson K E, Weinstock G M, Highlander S K, Worley K C, Creasy H H, Wortman J R, Rusch D B, Mitreva M, Sodergren E, et al. A catalog of reference genomes from the human microbiome. *Science.* 2010; 328(5981):994-9.
129. Crost E H, Tailford L E, Le Gall G, Fons M, Henrissat B, and Juge N. Utilisation of mucin glycans by the human gut symbiont *Ruminococcus gnavus* is strain-dependent. *PLoS One.* 2013; 8(10):e76341.
130. Dabard J, Bridonneau C, Phillipe C, Anglade P, Molle D, Nardi M, Ladire M, Girardin H, Marcille F, Gomez A, et al. Ruminococcin A, a new lantibiotic produced by a *Ruminococcus gnavus* strain isolated from human feces. *Appl Environ Microbiol.* 2001; 67(9):4111-8.
131. Petrof E O, Gloor G B, Vanner S J, Weese S J, Carter D, Daigneault M C, Brown E M, Schroeter K, and Allen-Vercoe E. Stool substitute transplant therapy for the eradication of *Clostridium difficile* infection: 'RePOOPulating' the gut. *Microbiome.* 2013; 1(1):3.
132. Bondia-Pons I, Maukonen J, Mattila I, Rissanen A, Saarela M, Kaprio J, Hakkarainen A, Lundbom J, Lundbom N, Hyotylainen T, et al. Metabolome and fecal microbiota in monozygotic twin pairs discordant for weight: a Big Mac challenge. *FASEB J.* 2014; 28(9):4169-79.
133. Atarashi K, Tanoue T, Oshima K, Suda W, Nagano Y, Nishikawa H, Fukuda S, Saito T, Narushima S, Hase K, et al. Treg induction by a rationally selected mixture of Clostridia strains from the human microbiota. *Nature.* 2013; 500(7461):232-6.
134. Eun C S, Mishima Y, Wohlgemuth S, Liu B, Bower M, Carroll I M, and Sartor R B. Induction of bacterial antigen-specific colitis by a simplified human microbiota consortium in gnotobiotic interleukin-10−/− mice. *Infect Immun.* 2014; 82(6): 2239-46.
135. Hoffmann T W, Pham H P, Bridonneau C, Aubry C, Lamas B, Martin-Gallausiaux C, Moroldo M, Rainteau D, Lapaque N, Six A, et al. Microorganisms linked to inflammatory bowel disease-associated dysbiosis differentially impact host physiology in gnotobiotic mice. *ISMS J.* 2015.
136. Joossens M, Huys G, Cnockaert M, De Preter V, Verbeke K, Rutgeerts P, Vandamme P, and Vermeire S. Dysbiosis of the faecal microbiota in patients with Crohn's disease and their unaffected relatives. *Gut.* 2011; 60(5): 631-7.
137. Willing B P, Dicksved J, Halfvarson J, Andersson A F, Lucio M, Zheng Z, Jarnerot G, Tysk C, Jansson J K, and Engstrand L. A pyrosequencing study in twins shows that gastrointestinal microbial profiles vary with inflammatory bowel disease phenotypes. *Gastroenterology.* 2010; 139 (6): 1844-54 el.
138. Breban M, Tap J, Leboime A, Said-Nahal R, Langella P, Chiocchia G, Furet J P, and Sokol H. Faecal microbiota study reveals specific dysbiosis in spondyloarthritis. *Ann Rheum Dis.* 2017.
139. Takahashi K, Nishida A, Fujimoto T, Fujii M, Shioya M, Imaeda H, Inatomi O, Bamba S, Sugimoto M, and Andoh A. Reduced Abundance of Butyrate-Producing Bacteria Species in the Fecal Microbial Community in Crohn's Disease. *Digestion.* 2016; 93(1):59-65.
140. Sanchez E, De Palma G, Capilla A, Nova E, Pozo T, Castillejo G, Varea V, Marcos A, Garrote J A, Polanco I, et al. Influence of environmental and genetic factors linked to celiac disease risk on infant gut colonization by *Bacteroides* species. *Appl Environ Microbiol.* 2011; 77(15): 5316-23.
141. Gul'neva M, and Shilkina N P. [Intestinal microbial biocenosis in patients with systemic lupus erythematosus treated with prednisolone]. *Klin Med (Mosk).* 2009; 87(6): 42-5.
142. Rodriguez-Iturbe B, and Haas M. In: Ferretti J J, Stevens D L, and Fischetti V A eds. *Streptococcus pyogenes: Basic Biology to Clinical Manifestations.* Oklahoma City (Okla.); 2016.
143. Ginsburg I. Role of lipoteichoic acid in infection and inflammation. *Lancet Infect Dis.* 2002; 2(3): 171-9.
144. Jacobsen S, Petersen J, Ullman S, Junker P, Voss A, Rasmussen J M, Tarp U, Poulsen L H, van Overeem Hansen G, Skaarup B, et al. A multicentre study of 513 Danish patients with systemic lupus erythematosus. II. Disease mortality and clinical factors of prognostic value. *Clin Rheumatol.* 1998; 17(6):478-84.
145. Seligman V A, Lum R F, Olson J L, Li H, and Criswell L A. Demographic differences in the development of lupus nephritis: a retrospective analysis. *Am J Med.* 2002; 112(9):726-9.
146. Ng K P, Manson J J, Rahman A, and Isenberg D A. Association of antinucleosome antibodies with disease flare in serologically active clinically quiescent patients with systemic lupus erythematosus. *Arthritis Rheum.* 2006; 55(6):900-4.
147. Oelzner P, Deliyska B, Funfstuck R, Hein G, Herrmann D, and Stein G. Anti-C1q antibodies and antiendothelial cell antibodies in systemic lupus erythematosus—relationship with disease activity and renal involvement. *Clin Rheumatol.* 2003; 22(4-5):271-8.
148. Apperloo-Renkema H Z, Bootsma H, Mulder B I, Kallenberg C G, and van der Waaij D. Host-microflora interaction in systemic lupus erythematosus (SLE): colonization resistance of the indigenous bacteria of the intestinal tract. *Epidemiol Infect.* 1994; 112(2):367-73.
149. Arbuckle M R, McClain M T, Rubertone M V, Scofield R H, Dennis G J, James J A, and Harley J B. Development of autoantibodies before the clinical onset of systemic lupus erythematosus. *N Engl J Med.* 2003; 349(16): 1526-33.
150. Almaani S, Meara A, and Rovin B H. Update on Lupus Nephritis. *Clin J Am Soc Nephrol.* 2017; 12(5): 825-35.
151. Fasano A. Leaky gut and autoimmune diseases. *Clin Rev Allergy Immunol.* 2012; 42(1):71-8.
152. Damian R T. Molecular Mimicry in Biological Adaptation. *Science.* 1965; 147(3660): 824.
153. Gladman D D, Ibanez D, and Urowitz M B. Systemic lupus erythematosus disease activity index 2000. *J Rheumatol.* 2002; 29(2):288-91.
154. Caporaso J G, Lauber C L, Walters W A, Berg-Lyons D, Huntley J, Fierer N, Owens S M, Betley J, Fraser L, Bauer M, et al. Ultra-high-throughput microbial community analysis on the Illumina HiSeq and MiSeq platforms. *ISMS J.* 2012; 6(8):1621-4.
155. Determinants of warfarin use and international normalized ratio levels in atrial fibrillation patients in Japan.—Subanalysis of the J-RHYTHM Registry. *Circ J.* 2011; 75(10):2357-62.
156. Vaughan E E, Schut F, Heilig H G, Zoetendal E G, de Vos W M, and Akkermans A D. A molecular view of the intestinal ecosystem. *Curr Issues Intest Microbiol.* 2000; 1(1):1-12.
157. Qin J, Li R, Raes J, Arumugam M, Burgdorf K S, Manichanh C, Nielsen T, Pons N, Levenez F, Yamada T, et al. A human gut microbial gene catalogue established by metagenomic sequencing. *Nature.* 2010; 464(7285): 59-65.

158. Kuczynski J, Stombaugh J, Walters W A, Gonzalez A, Caporaso J G, and Knight R. Using QIIME to analyze 16S rRNA gene sequences from microbial communities. *Curr Protoc Bioinformatics.* 2011; Chapter 10(Unit 10 7.
159. Caporaso J G, Kuczynski J, Stombaugh J, Bittinger K, Bushman F D, Costello E K, Fierer N, Pena A G, Goodrich J K, Gordon J I, et al. QIIME allows analysis of high-throughput community sequencing data. *Nat Methods.* 2010; 7(5):335-6.
160. Edgar R C. Search and clustering orders of magnitude faster than BLAST. *Bioinformatics.* 2010; 26(19):2460-1.
161. Price M N, Dehal P S, and Arkin A P. FastTree 2—approximately maximum-likelihood trees for large alignments. *PLoS One.* 2010; 5(3):e9490.
162. Lozupone C, Lladser M E, Knights D, Stombaugh J, and Knight R. UniFrac: an effective distance metric for microbial community comparison. *ISME J* 2011; 5(2): 169-72.
163. McMurdie P J, and Holmes S. phyloseq: an R package for reproducible interactive analysis and graphics of microbiome census data. *PLoS One.* 2013; 8(4):e61217.
164. Benjamini Y. Controlling the false discovery rate: a proactical and useful approach to multiple testing. *J Royal Stat Soc Ser.* 199557):289-300.
165. Amos C I, Chen W V, Seldin M F, Remmers E F, Taylor K E, Criswell L A, Lee A T, Plenge R M, Kastner D L, and Gregersen P K. Data for Genetic Analysis Workshop 16 Problem 1, association analysis of rheumatoid arthritis data. *BMC Proc.* 2009; 3 Suppl 7(S2.
166. Gronwall C, Akhter E, Oh C, Burlingame R W, Petri M, and Silverman G J. IgM autoantibodies to distinct apoptosis-associated antigens correlate with protection from cardiovascular events and renal disease in patients with SLE. *Clin Immunol.* 2012; 142(3):390-8.
167. Pelzek A J, Gronwall C, Rosenthal P, Greenberg J D, McGeachy M, Moreland L, Rigby W F C, and Silverman G J. Persistence of Disease-Associated Anti-Citrullinated Protein Antibody-Expressing Memory B Cells in Rheumatoid Arthritis in Clinical Remission. *Arthritis Rheumatol.* 2017; 69(6): 1176-86.
168. Fischer, W. 1993. Molecular analysis of lipid macroamphiphiles by hydrophobic interaction chromatography, exemplified with lipoteichoic acids. *Anal Biochem* 208: 49-56.
169. Fischer, W. 1994. Lipoteichoic acids and lipoglycans. In Bacterial cell wall. J. M. a. H. Ghuysen, R., editor Elsevier Science, Amsterdam, The Netherlands. 119-215.
170. Flaherty, C., D. E. Minnikin, and I. C. Sutcliffe. 1996. A chemotaxonomic study of the lipoglycans of *Rhodococcus rhodnii* N445 (NCIMB 11279). *Zentralbl Bakteriol* 285:11-19.
171. Fotis, L., N. Shaikh, K. W. Baszis, C. M. Samson, R. Lev-Tzion, A. R. French, and P. I. Tarr. 2017. Serologic Evidence of Gut-driven Systemic Inflammation in Juvenile Idiopathic Arthritis. *J Rheumatol* 44:1624-1631.
172. Gisbert, J. P., F. Bermejo, J. L. Perez-Calle, C. Taxonera, I. Vera, A. G. McNicholl, A. Algaba, P. Lopez, N. Lopez-Palacios, M. Calvo, Y. Gonzalez-Lama, J. A. Carneros, M. Velasco, and J. Mate. 2009. Fecal calprotectin and lactoferrin for the prediction of inflammatory bowel disease relapse. *Inflamm Bowel Dis* 15:1190-1198.
173. Nagpal, R., and H. Yaday. 2017. Bacterial Translocation from the Gut to the Distant Organs: An Overview. *Ann Nutr Metab* 71 Suppl 1:11-16.
174. Shulman, R. J., M. N. Eakin, D. I. Czyzewski, M. Jarrett, and C. N. Ou. 2008. Increased gastrointestinal permeability and gut inflammation in children with functional abdominal pain and irritable bowel syndrome. *J Pediatr* 153:646-650.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A method for determining (i) whether a subject has systemic lupus erythematosus (SLE) and/or lupus nephritis or (ii) whether a subject diagnosed with SLE or incomplete lupus (ILE) is at an increased risk for developing lupus nephritis, progression of SLE, and/or complications of lupus, said method comprising:
    (a) determining in a bodily fluid sample collected from the subject a level of antibodies which recognize a bacterial lipoglycan-containing antigen,
    (b) comparing the level of the antibodies determined in step (a) to a control level of said antibodies, and
    (c) determining that the subject has SLE and/or lupus nephritis or is at an increased risk for developing lupus nephritis, progression of SLE, and/or complications of lupus if the level of the antibodies determined in step (a) is statistically significantly higher than the control level,
    wherein the lipoglycan-containing antigen is associated with *Ruminococcus gnavus* strain CC55 001C, HM-1056, and
    wherein the lipoglycan-containing antigen is the same as the lipoglycan-containing antigen obtained using a method selected from:
    (i) Method 1 comprising the steps:
    a. culturing *Ruminococcus gnavus* strain CC55 001C, HM-1056 at 37° C. under anaerobic conditions for 2-7 days, and
    b. producing bacterial extract in the presence of a lysozyme, *Serratia marcescens* endonuclease, Proteinase K, and a detergent under non-denaturing conditions;
    (ii) Method 2 comprising the steps:
    a. culturing *Ruminococcus gnavus* strain CC55 001C, HM-1056 in rich nutrient media at 37° C. under anaerobic conditions (75% $N_2$, 20% $CO_2$, and 5% $H_2$) for 2-7 days,
    b. pelleting bacteria by centrifugation,
    c. producing a bacterial extract in a protein extraction buffer in the presence of lysozyme, *Serratia marcescens* endonuclease, and a detergent under non-denaturing conditions,
    d. treating the extract obtained in step (c) with Proteinase K,
    e. incubating the treated extract obtained in step (d) at 55° C. for about 10 minutes,
    f. removing cell debris by centrifugation, and
    g. using the supernatant as an antigen preparation; or
    (iii) Method 3 comprising the steps:
    a. disrupting *Ruminococcus gnavus* strain CC55 001C, HM-1056 cells with a French press,
    b. ultracentrifugating to obtain a precipitate and produce an ultracentrifugation supernatant, c. subjecting the ultracentrifugation supernatant obtained in step (b) to butanol-water extraction and isolating an aqueous phase,
d. applying the aqueous phase from step (c) to a hydrophobic interaction chromatography matrix, and
e. isolating lipoglycan-containing fractions.

2. The method of claim 1, wherein the bodily fluid is selected from whole blood, plasma, serum, urine, and saliva.

3. The method of claim 1, wherein the control level of antibodies is selected from (i) a predetermined standard, (ii) a level in a similarly prepared sample obtained from the same subject in the past, and (iii) a level in a similarly prepared sample obtained from a healthy unaffected subject or a mean value of several unaffected healthy subjects.

4. The method of claim 1, wherein in step (c), the level of the antibodies is determined to be statistically significantly higher than the control level if said level is higher than a mean value calculated for unaffected healthy subjects plus two standard deviations.

5. The method of claim 1, wherein the lupus nephritis is proliferative lupus nephritis, membranous lupus nephritis, membranoproliferative lupus nephritis, or mesangial glomerulonephritis.

6. The method of claim 1, wherein the method further comprises (i) determining in a bodily fluid sample collected from the subject a level of antibodies which recognize an antigen selected from double-stranded DNA (dsDNA), C1q, glomerular extract, nucleosomes, Smith Antibody (Sm), U1RNP, Ro/SSA, La/SSB, and histone(s), and/or (ii) determining serum level(s) of one or more complement components, and/or (iii) determining erythrocyte sedimentation rate (ESR), and/or (iv) performing a kidney assessment.

7. The method of claim 1, further comprising recruiting the subject in a clinical trial for the treatment of SLE and/or lupus nephritis.

8. The method of claim 1, further comprising administering a therapeutic or preventive treatment to the subject.

9. The method of claim 8, wherein the treatment (i) results in a decrease in the level of the antibodies which recognize said lipoglycan-containing antigen or (ii) results in a decrease in GI microbiota of the subject of an abundance of bacteria from *Ruminococcus gnavus* strain CC55_001C, HM-1056.

* * * * *